(12) United States Patent
Tisi et al.

(10) Patent No.: US 9,410,190 B2
(45) Date of Patent: Aug. 9, 2016

(54) STEM ACCELERATED ISOTHERMAL NUCLEIC ACID AMPLIFICATION TECHNOLOGY

(75) Inventors: Laurence Carlo Tisi, Cambridge (GB); Olga Gandelman, Cambridge (GB); Guy Kiddle, Cambridge (GB); Cathal Joseph McElgunn, Cambridge (GB)

(73) Assignee: LUMORA LTD., Cambridge (GB)

( * ) Notice: Subject to any disclaimer, the term of this patent is extended or adjusted under 35 U.S.C. 154(b) by 1183 days.

(21) Appl. No.: 13/377,704

(22) PCT Filed: Jun. 15, 2010

(86) PCT No.: PCT/GB2010/001169
§ 371 (c)(1),
(2), (4) Date: Mar. 5, 2012

(87) PCT Pub. No.: WO2010/146349
PCT Pub. Date: Dec. 23, 2010

(65) Prior Publication Data
US 2012/0157326 A1 Jun. 21, 2012

(30) Foreign Application Priority Data
Jun. 15, 2009 (GB) .................................. 0910302.9

(51) Int. Cl.
*C12P 19/34* (2006.01)
*C12Q 1/68* (2006.01)

(52) U.S. Cl.
CPC .................................. *C12Q 1/6844* (2013.01)

(58) Field of Classification Search
USPC ................................................ 435/6.12, 91.2
See application file for complete search history.

(56) References Cited

U.S. PATENT DOCUMENTS

| 5,866,336 | A | * | 2/1999 | Nazarenko et al. | 435/6.12 |
| 7,374,913 | B2 | * | 5/2008 | Nagamine | 435/91.2 |
| 7,803,544 | B2 | * | 9/2010 | Nakamura et al. | 435/6.11 |
| 2009/0061425 | A1 | | 3/2009 | Lo et al. | |
| 2009/0061433 | A1 | | 3/2009 | Nakamura et al. | |

FOREIGN PATENT DOCUMENTS

| EP | 1 876 246 | 1/2008 |
| EP | 1 988 178 | 11/2008 |
| WO | WO 02/090538 | 11/2002 |
| WO | WO 2004/013354 | 2/2004 |
| WO | WO 2007/025281 | 3/2007 |
| WO | WO 2008/043987 | 4/2008 |

OTHER PUBLICATIONS

International Search Report for PCT/GB2010/001169, mailed Aug. 24, 2010.
Written Opinion of the International Searching Authority for PCT/GB2010/001169, mailed Aug. 24, 2010.
International Preliminary Report on Patentability with 5 Amended Sheets, mailed Sep. 13, 2011.
Database WPI Week 200311, Accession No. 2003-120547, (Nov. 14, 2002), Abstract.

(Continued)

*Primary Examiner* — Kenneth Horlick
(74) *Attorney, Agent, or Firm* — Nixon & Vanderhye P.C.

(57) ABSTRACT

The invention is in the field of nucleic acid amplification, hi particular, methods are described which utilize stem primers that improve the rapid and specific amplification of a test sample.

39 Claims, 47 Drawing Sheets

(56) References Cited

OTHER PUBLICATIONS

Misawa, Y. et al., "Application of loop-mediated isothermal amplification technique to rapid and direct detection of methicillin-resistant *Staphylococcus aureus* (MRSA) in blood cultures", Journal of Infection and Chemotherapy, vol. 13, No. 3, (Jun. 2007), pp. 134-140.
GB Search Report dated Sep. 29, 2009, issued in connection with GB 0910302.9.

* cited by examiner

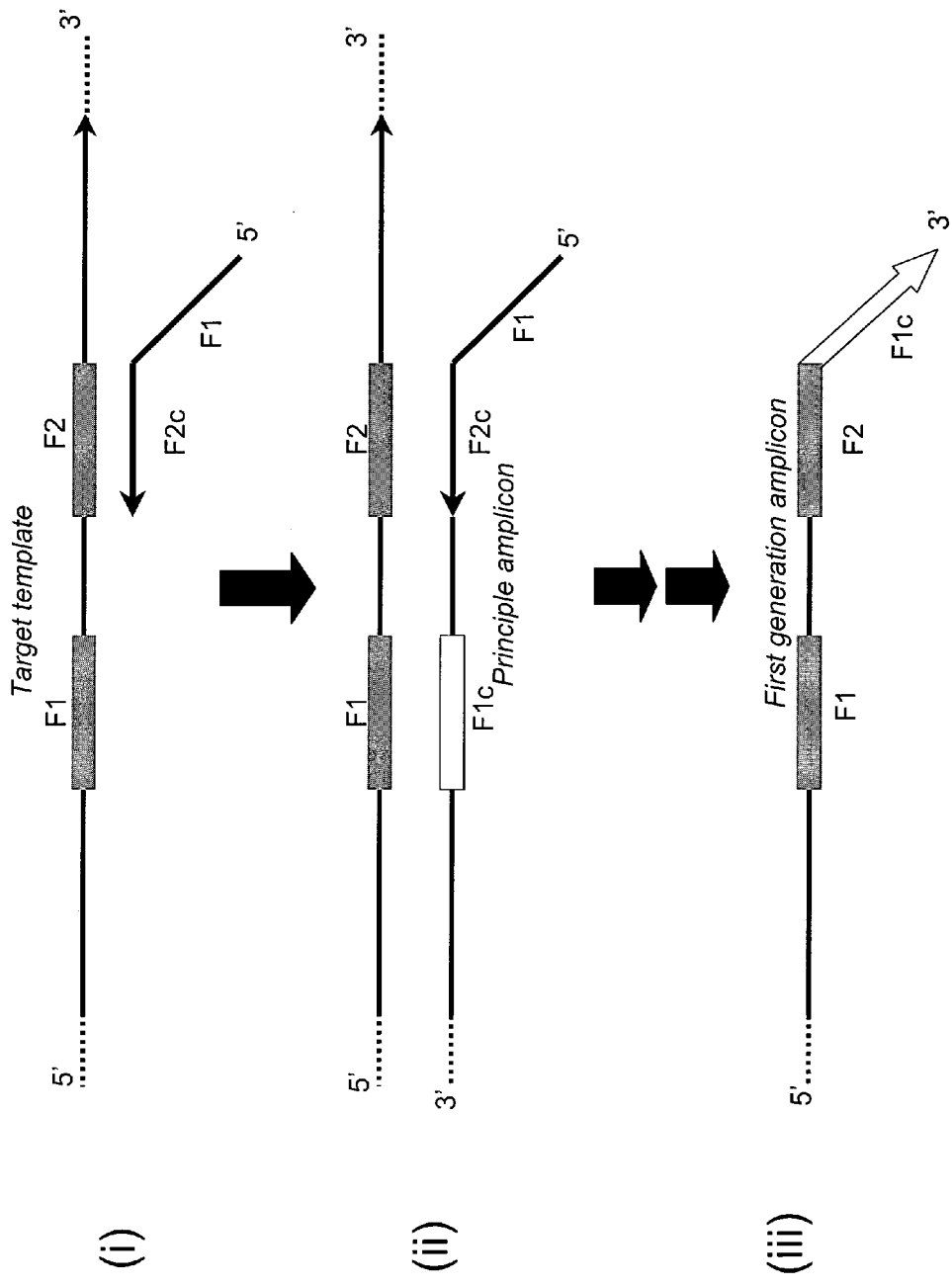

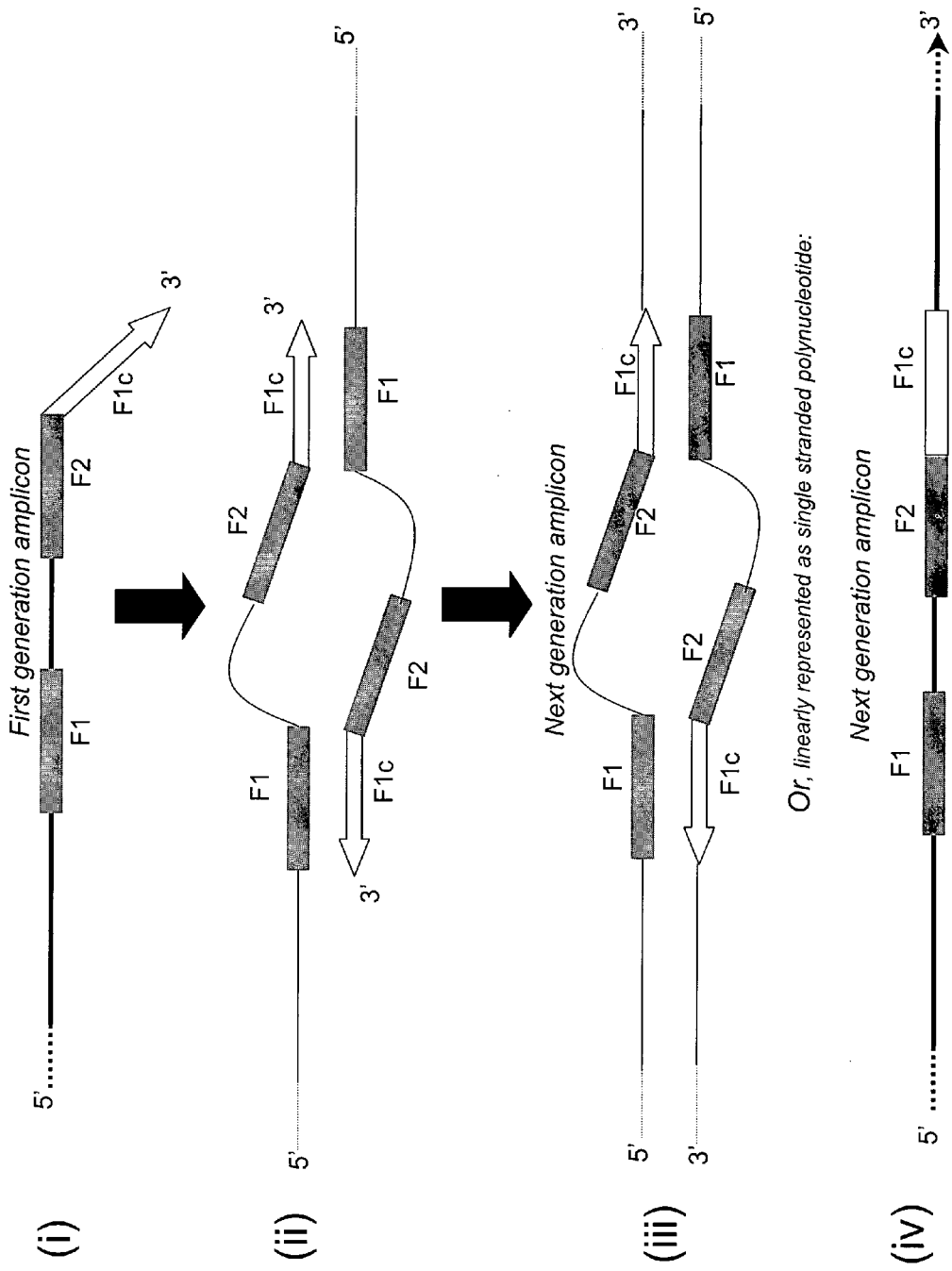

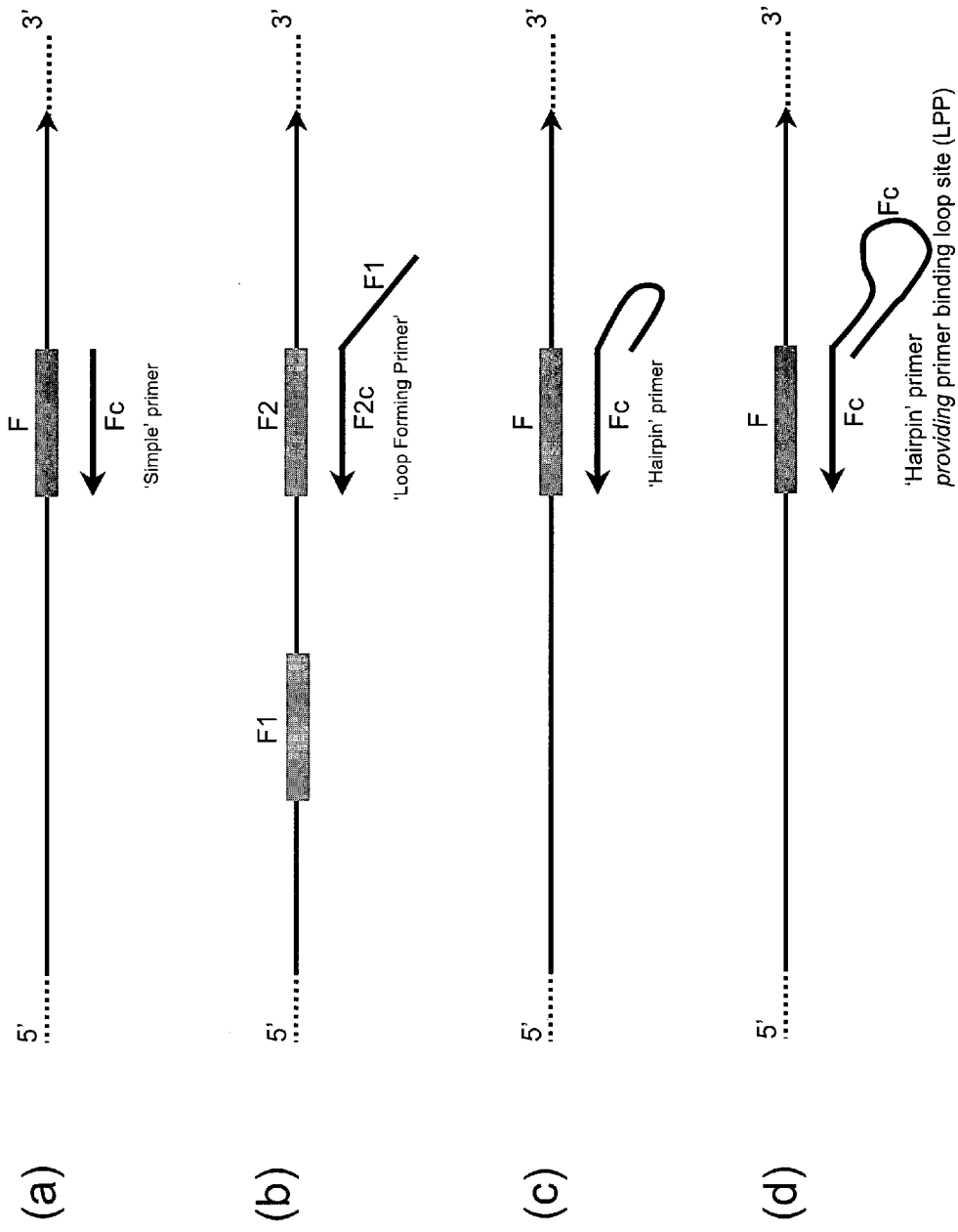

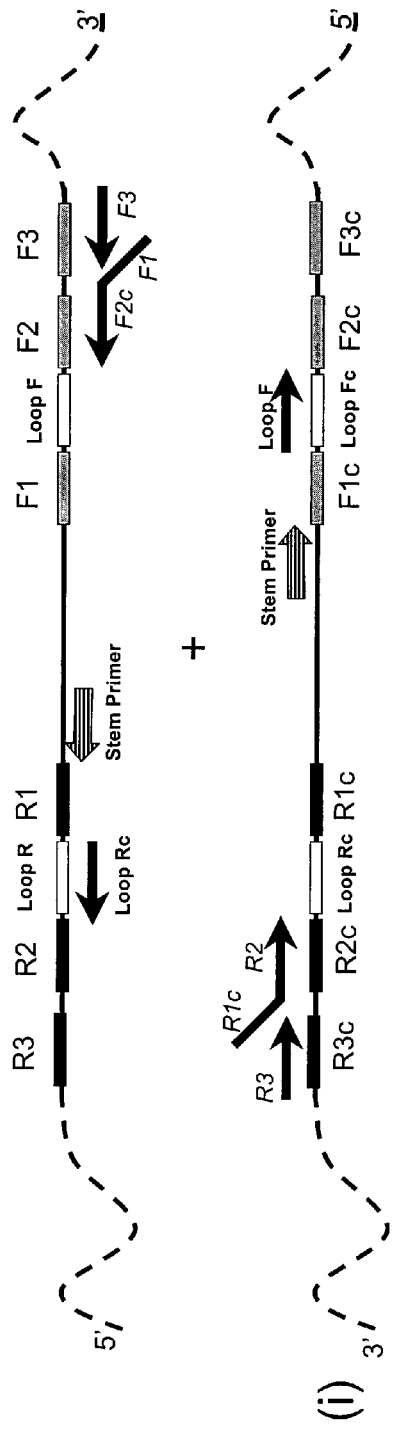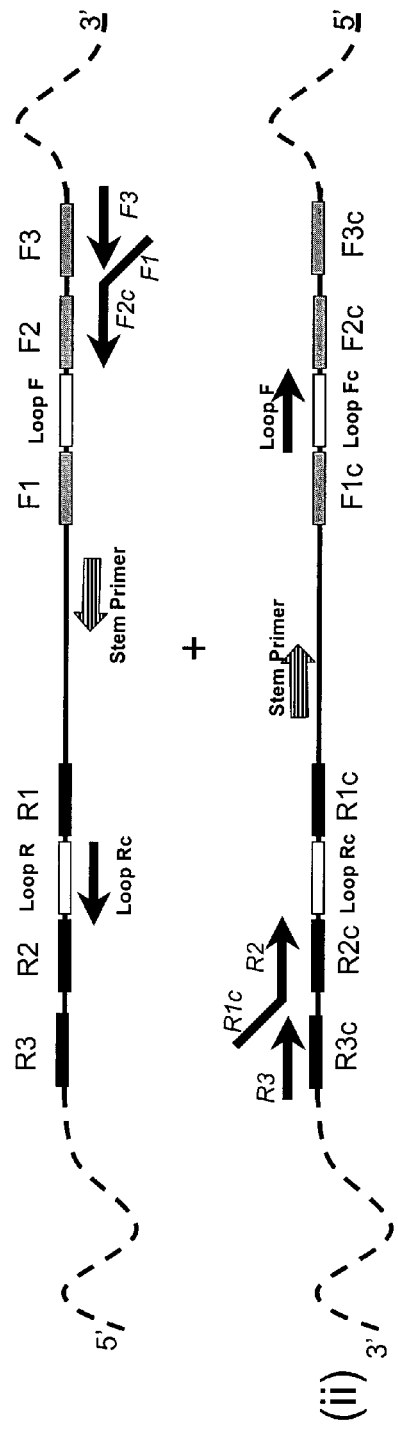
FIGURE 18

STEM ACCELERATED ISOTHERMAL NUCLEIC ACID AMPLIFICATION TECHNOLOGY

This application is the U.S. national phase of International Application No. PCT/GB2010/001169, filed 15 Jun. 2010, which designated the U.S. and claims priority to GB Application No. 0910302.9, filed 15 Jun. 2009, the entire contents of each of which are hereby incorporated by reference.

This patent application claims priority from United Kingdom patent application no GB0910302.9, filed 15 Jun. 2009, the complete contents of which are incorporated herein by reference.

FIELD OF THE INVENTION

The present invention relates to the field of nucleic acid amplification. In particular, it relates to a method which improves the rapid and specific amplification and detection of a test sample.

BACKGROUND

Nucleic acid amplification technology (NAAT) is an invaluable and powerful tool in many areas of research and diagnosis. NAAT techniques allow detection and quantification of a nucleic acid in a sample with high sensitivity and specificity as well as quantitative analysis of nucleic acids in a sample.

Nucleic acid amplification may be used to determine the presence of a particular template nucleic acid in a sample, as indicated by the presence of an amplification product following the implementation of a particular NAAT. Conversely, the absence of any amplification product indicates the absence of template nucleic acid in the sample. Such techniques are of great importance in diagnostic applications, for example, for determining whether a pathogen is present in a sample.

The prior art has described a variety of thermocycling and isothermal techniques for amplification of nucleic acids. Thermocycling techniques, such as the polymerase chain reaction (PCR), use temperature cycling to drive repeated cycles of DNA synthesis leading to large amounts of new DNA being synthesised in proportion to the original amount of template DNA. A number of isothermal techniques have also been developed that do not rely on thermocycling to drive the amplification reaction. Isothermal techniques, which utilise DNA polymerases with strand-displacement activity, have been developed for amplification reactions that do not involve an RNA-synthesis step. Similarly, for amplification reactions that do involve an RNA-synthesis step, isothermal techniques have been developed that may use reverse transcriptase, RNase H and/or a DNA-dependent RNA polymerase (see for example, Nucleic Acid Isothermal Amplification Technologies—A Review. Nucleosides, Nucleotides and Nucleic Acids, Volume 27, Issue 3 Mar. 2008, pages 224-243).

The polynucleic acid produced by the amplification technology employed is generically referred to as amplicon. The nature of amplicon produced varies significantly depending on the NAAT being practised. For example, NAATs such as PCR may produce amplicon which is substantially of identical size and sequence. Other NAATs produce amplicon of very varied size wherein the amplicon is composed of different numbers of repeated sequences such that the amplicon is a collection of concatamers of different length. The repeating sequence from such concatamers will reflect the sequence of the polynucleic acid which is the subject of the assay being performed.

Given that NAATs are of paramount importance in many areas, for example diagnostic applications, there is a continued need in the art to provide NAATs which have improved speed, sensitivity and specificity. The present invention provides simple and cost-effective methods for achieving this goal. Furthermore, the present invention has the advantage that the rate increases achieved by the method of the present invention can counteract amplification rate decreases caused by sequence dependent issues that cause primer designs for a particular NAAT to be sub-optimal. Such rate increases can further lower the cost of an assay based on a particular NAAT as costly alternative means to increase amplification rates can be avoided.

DETAILED DESCRIPTION OF THE PREFERRED EMBODIMENTS

The present invention provides an improved method of amplifying polynucleic acids. Thus, in one embodiment, the present invention provides a method of synthesizing a polynucleic acid wherein said method comprises the steps of a) providing a target template which comprises at least a first and a second reciprocal primer binding region;

b) providing a first primer comprising a first and a second segment, wherein the first segment is substantially complementary to the first reciprocal primer binding region on the template and the second segment comprises a sequence that is substantially complementary to another region in the first primer or a region in the amplicon generated from the first segment of the first primer such that the second segment is able to form a loop;

c) providing a second primer comprising a first and optionally a second segment, wherein the first segment is substantially complementary to the second primer binding region on the template and the optional second segment comprises a sequence that is substantially complementary to another region in the second primer or a region in the amplicon generated from the first segment of the second primer such that the second region is able to form a loop;

d) providing at least one primer which is capable of binding to the region between the first and second reciprocal primer binding regions;

e) providing the necessary reagents and conditions to perform synthesis of the polynucleic acid;

f) performing synthesis of the polynucleic acid.

The underlying principle of the present invention is that it has been surprisingly discovered that the provision of one or more "stem primer(s)", i.e. primers that bind to the region between the forward and the reverse reciprocal primer binding regions, significantly enhances the speed and sensitivity of certain NAATs.

"Forward reciprocal primer binding site" and "reverse reciprocal primer binding site" refers to the regions on the template DNA and/or the amplicon to which the forward and reverse reciprocal primers bind. The term "reciprocal primer" or "reciprocal primers" as used herein relates to two or more primers which act to delimit the region of the original template polynucleotide which is exponentially amplified during amplification (FIGS. 1a and 1b). In some embodiments, additional primers may bind to the region 5' of the forward reciprocal primer and/or reverse reciprocal primers. Where such additional primers are used, the forward reciprocal primer binding site and/or the reverse reciprocal primer binding site may encompass the binding regions of these additional primers as well as the binding regions of the reciprocal primers themselves. For example, in some embodiments, the method may use one or more additional primers which bind to a region that lies 5' of the forward and/or reverse reciprocal primer binding region. Such a method was disclosed, for example, in WO0028082 which discloses the use of "displacement primers" or "outer primers".

WO0028082 describes the use of loop-forming primers (LFPs), where a LFP is understood to comprise a first and second segment, wherein the first segment is substantially complementary to a primer binding region on the template and the second segment comprises a sequence that is substantially complementary to a region in the amplicon generated from the first segment of the first primer such that the second segment is able to form a loop, and mentions that the NAAT uses two "outer primers" in addition to the LFPs. These primers are characterised in that the "first outer primer" binds 3' to the "F2" site in the template (i.e. the first outer primer binds the "F3" site, FIG. 14b) and the "second outer primer" binds 3' to the binding region of the second LFP, the "R2c" site (i.e. the second outer primer binds the "R3c" site, FIG. 14b). Thus, these primers do not bind in the stem-region of the amplicon, which lies 5' of the primer binding sites of the LFPs.

The region between the forward and reverse reciprocal primer binding regions represents a region which is guaranteed to form part of the amplicon but does not itself conventionally provide for any primer binding sites. This region is referred to herein as the "stem region" of the amplicon. Primers which bind to the stem region are referred to herein as "stem primers" (FIG. 1c; FIG. 2a-2e). Stem primers can be defined as primers which bind to the stem region. They may further be defined as primers that bind the region 3' of the forward reciprocal primer binding region on the forward strand and 3' of the reverse reciprocal primer binding site on the reverse strand. It is understood that the reciprocal primer binding sites and the binding sites of the stem primers do not significantly overlap. It is preferred that the reciprocal primer binding sites and the binding sites of the stem primers do not overlap at all.

"Significantly" in the context of overlapping primer binding regions means that the primer binding sites overlap by less than 10 nucleotides, less than 9 nucleotides, less than 8 nucleotides, less than 7 nucleotides, less than 6 nucleotides, less than 5 nucleotides, less than 4 nucleotides, less than 3 nucleotides, less than 2 nucleotides or less than 1 nucleotide. It is preferred that they do not overlap at all. Stem primers may further still be defined as primers that bind the region 3' of the forward reciprocal primer binding region on the forward strand and 3' of the reverse reciprocal primer binding site on the reverse strand but where the primer binding regions do not substantially overlap with any intra-molecular secondary structure generated as a direct consequence of the primers employed by a particular NAAT, especially a LFP (FIG. 1d).

It has been surprisingly discovered that the use of stem primers significantly increases the rate of amplification. This has the distinct advantage that diagnostic tests, for example, can deliver test results in a shorter period of time, something of common value amongst users of diagnostic tests. An additional benefit of faster amplification is that it can decrease the possibility of false positive results and hence increase the specificity of a test. It has been the inventors' experience that NAATs employing strand displacing polymerases become increasingly prone to non-specific amplification as the length of time required for amplification increases. As such, faster amplification can also lead to more accurate results.

Stem primers not only provide for more rapid amplification but provide at least two further key benefits. Firstly, the use of stem primers to increase the rate of amplification of NAATs such as Loop-mediated Isothermal Amplification (LAMP), Template Re-priming Amplification (TRA), Self Extending Amplification (SEA) and SMart Amplification Process (SMAP), which will be discussed in more detail below, avoids costly alternatives for achieving more rapid amplification, such as the use of more polymerase or more dNTPs. For example, at 2009 prices, doubling the amount of Bst DNA Polymerase in a LAMP reaction increases the cost of an assay by 60%, doubling dNTPs increases the cost of an assay by 20% but adding two stem primers increases the cost of an assay by only 4%, as primers are generally not very expensive.

Secondly, stem primers provide greater flexibility in primer selection for a given target template. For example, in order to detect a particular family of pathogens which have significant variations in their nucleic acid sequences, primers will be designed to regions of the pathogen family genome which show the least sequence variation. However, this may require that one or more primers are positioned in a non-optimal site. This can be a particular problem with NAATs such as LAMP, which will be discussed below, where the position of up to six different primers needs to be accommodated in a certain fashion. Since stem primers can be positioned very differently to the other primers used in NAATs, one can make use of binding sites of stem primers in a particular target template which would otherwise be difficult to use.

In fact, generally, the employment of stem primers may allow for the omission of other primers used in the LAMP (or SMAP) method. For example, for a particular target template, it may prove difficult to find optimal binding sites for one of the so-called 'displacement primers' (i.e. primers occupying positions R3 and F3 in FIG. 14b, c and e) with the result that test performance is adversely affected. However, should there be suitable stem primer binding sites available on the target template, the addition of stem primers can act to rescue the performance loss from the lack of the displacement primer (FIG. 19). This principle can be similarly applied to certain other primers employed in LAMP, or SMAP.

The method of the invention may be practised with any NAAT provided that said NAAT results in the formation of concatamers. The term "concatamer" as used herein refers to a polynucleic acid having substantially similar nucleotide sequences linked alternately in a single-stranded chain. These arrayed sequences may be simple repeats of each other, inverted repeats or combinations thereof.

NAATs which are suitable for the generation of concatamers are well known in the art and generally include "isothermal" amplification techniques. This means that the amplification of the polynucleic acid does not require a change in the incubation temperature, contrary to known thermocycling techniques, such as polymerase chain reaction.

Some isothermal amplification techniques are dependent on transcription as part of the amplification process, for example Nucleic Acid Sequence Based Amplification (NASBA; U.S. Pat. No. 5,409,818) and Transcription Mediated Amplification (TMA; U.S. Pat. No. 5,399,491) while others are dependent on the action of a Helicase or Recombinase for example Helicase Dependent Amplification (HDA; WO2004027025) and Recombinase polymerase amplification (RPA; WO03072805) respectively, others still are dependent on the strand displacement activity of certain DNA polymerases, for example Strand Displacement Amplification (SDA; U.S. Pat. No. 5,455,166), Loop-mediated Isothermal Amplification (LAMP; WO0028082, WO0134790, WO0224902), Chimera Displacement Reaction (RDC; WO9794126), Rolling Circle Amplification (RCA; Lizardi, P. M. et al. Nature Genetics, (1998) 19.225-231), Isothermal Chimeric Amplification of Nucleic Acids (ICAN; WO0216639), SMart Amplification Process (SMAP; WO2005063977), Linear Isothermal Multimerization Amplification (LIMA; Isothermal amplification and multimerization of DNA by Bst DNA polymerase, Hafner G. J., Yang I. C., Wolter L. C., Stafford M. R., Giffard P. M, BioTechniques, 2001, vol. 30, no4, pp. 852-867) also methods as described in U.S. Pat. No. 6,743,605 (herein referred to as 'Template Re-priming Amplification' or TRA) and WO9601327 (herein referred to as 'Self Extending Amplification' or SEA).

A characteristic of these NAATs is that they provide for both copying of a polynucleic acid via the action of a primer or set of primers and for re-copying of said copy by a reciprocal primer or set of primers. This enables the generation of copies of the original polynucleic acid at an exponential rate.

With reference to NAATs in general it is helpful to differentiate between the physical piece of nucleic acid being detected by the method, from the first copy made of this original nucleic acid, from the first copy of the copy made from this original nucleic acid, from further copies of this copy of a copy. For the sake of clarity the following definitions will be adhered to herein: the nucleic acid whose provenance is from the sample being analysed itself will be referred to as the 'Target Template' (FIG. 3a); the first primer dependent copy of the target template by the NAAT being practised will be referred to as a 'Principal Amplicon' (FIG. 3a); the first copy of the Principal Amplicon by the NAAT being practised will be referred to as 'First Generation Amplicon' (FIG. 3b); further copies of the First Generation Amplicon (and copies of these copies) will be referred to collectively as 'Next Generation Amplicon' (FIG. 3c). Principal Amplicon, First Generation Amplicon and Next Generation Amplicon are all subsets of amplicon in general. It is possible for double stranded amplicon to be comprised of combinations of the aforementioned sub-sets or with the Target Template itself Further it is possible that Next Generation Amplicon is identical to First Generation Amplicon. Further still, it is possible to generate polynucleic acid molecules identical to First Generation Amplicon from Next Generation Amplicon.

The subject of the present invention is with particular reference to Next Generation Amplicon, in that it provides for further mechanisms by which it can be propagated in a manner which provides for further re-copying of the resultant copy.

The subsets of amplicon described above commonly have different characteristics. Principal Amplicon may be of very variable length as the target template can be copied from the first priming site beyond the region of nucleic acid delineated by the primers employed in a particular NAAT. In general, a key feature of the NAAT will be to provide a method by which this Principal Amplicon can be made available to another reciprocal primer employed by the NAAT in question so as to generate First Generation Amplicon. The First Generation Amplicon resulting from the primer dependent priming of the Principal Amplicon will be of a discrete length delineated by the primers used. Again, a key feature of the NAAT will be to provide a method by which this First Generation Amplicon can be made available for further priming by a reciprocal primer in order to generate Next Generation Amplicon. Again, a key feature of the NAAT in question will be to provide for a method for the further recopying of Next Generation Amplicon. For some NAATs, Next Generation Amplicon may be substantially different from the First Generation Amplicon, in particular, the Next Generation Amplicon may be a concatamer of the First Generation Amplicon.

Methods which produce amplicons in the form of concatamers directly from linear target templates include LAMP, TRA, SEA and SMAP (the latter is a hybrid of LAMP and SEA). In each case the concatamers arise from processes involving the first generation amplicon (FIG. 3b). Thus, it is preferred that synthesis of the polynucleic acid is performed using a NAAT selected from the group consisting of LAMP, TRA, SEA and SMAP. In each case therefore, the invention is associated with a NAAT which provides one or more primers with the capability of producing a concatamer directly from a linear target template.

RCA also produces concatamers. However, in this case, the target template specific ligation of a probe to form a covalently closed circular DNA molecule is required. As such amplicon will be concatameric in nature without the aid of any reciprocal primers or without the requirement of any primer comprising a first and a second segment, wherein the first segment is substantially complementary to the first reciprocal primer binding region on the template and the second segment comprises a sequence that is substantially complementary to another region in the first primer or a region in the amplicon generated from the first segment of the first primer such that the second segment is able to form a loop. As such, RCA per se, is not a subject of the present invention A common feature of LAMP, TRA, SMAP and SEA is therefore that of first generation amplicon dependent priming, i.e. where the first generation amplicon acts as a primer itself, whether by an intra-molecular event or inter-molecular event, leading to next generation amplicon (this term is used herein to refer to further copies of the first generation amplicon ((and copies of these copies); FIG. 3c) that is larger in size than the first generation amplicon and which is concatameric in nature. In fact, it is a characteristic of these NAATs that longer and longer amplicon is generated from shorter amplicon such that the number of binding sites for stem primers increases exponentially during the amplification process and hence the ability for stem primers to accelerate amplification. Appreciation of the mechanism of action of the primers generating the concatamers in these NAATs is helpful in understanding how stem primers have their effect. Furthermore, the skilled person aware of the mechanisms which lead to generation of a concatamer will readily be able to identify other suitable NAATs which can be used in the methods of the present invention.

The details of the process by which LAMP forms concatameric structures is depicted in FIG. 4. It is anticipated that the TRA method forms concatameric amplicon via an identical mechanism. FIGS. 4b and 4c show that, in fact, there are at least two mechanisms by which concatamers can form, one is via an intra-molecular mechanism (FIG. 4b) and one is via an inter-molecular mechanism (FIG. 4c). In fact, as shown herein, either mechanism gives identical results in terms of the structure of the first generation and next generation amplicon (compare FIG. 4b(iv) and FIG. 4c(iv)). It is to be understood that the process outlined in FIG. 4, which is only with reference to the forward reciprocal primer binding region, applies equally to the reverse reciprocal primer binding region. Further, the process is understood to be repeated by the next generation amplicons such that longer and longer concatamers can be formed.

Concatamer generation via SEA is essentially identical to that of LAMP and TRA except that the necessary inverted repeat is immediately inherent in the primer itself rather than requiring the extension of the primer on a polynucleotide to form the inverted repeat as in LAMP & TRA. FIG. 5*a-c* shows a corresponding mechanism for SEA as for LAMP/TRA.

Many NAATs make use of what is referred to herein as "simple primers" (FIG. 6*a*). "Simple primer" as used herein refers to a primer that is substantially complementary to a primer binding site on a polynucleic acid and wherein the primer does not contain a substantive number of additional nucleotides, i.e. nucleotides 3' or 5' of the primer region which is substantially complementary to the primer binding site. The term "substantive" in this context means that the simple primer contains fewer than about 20, fewer than about 15, fewer than about 10 or fewer than about 5 additional nucleotides.

A primer employed in LAMP and TRA (and by reference SMAP) generates single stranded loops in the amplicon and is hence referred to herein as "loop forming primer" (LFP). LFPs, as used herein, refers to primers which comprise a first and a second segment, wherein the first segment is substantially complementary to the primer binding region on the template and the second segment comprises a sequence that is substantially complementary to a region in the amplicon generated from the first segment of the first primer such that the second segment is able to form a loop. The general structure of LFPs is shown in FIG. 6*b*. The first (and next) generation amplicon resulting from the priming of the target template by a LFP contains a loop of single stranded polynucleotide flanked by double-stranded polynucleotide formed from Watson-Crick base-pairing of the inverted repeat sequence. The single-stranded loop of polynucleotide is understood to be available for binding by a further primer employed by the NAAT in question but specifically not by a stem primer.

The primers employed in SEA (and by reference SMAP, being a hybrid of SEA and LAMP) are shown in FIG. 6*c*. It can be seen that these primers contain an arbitrary inverted repeat at their 5' end. As a consequence, first generation amplicon resultant from the priming of a target template by said primers will form a tight hairpin loop that will cause the first generation amplicon to potentially self-prime (or prime off similar amplicon). Such primers are referred to herein as "hairpin primers". The term "hairpin primer" as used herein refers to a primer comprising a first and a second segment, wherein the first segment is substantially complementary to the primer binding region on the template and the second segment comprises a sequence that is substantially complementary to another region in the first primer. Hairpin primers do not usually provide for a single-stranded loop of polynucleotides in the first or next generation amplicon available for binding by a further polynucleotide employed by the NAAT in question. However, the inventors have recgonised that it is possible to provide hairpin primers wherein the inverted repeats in the second segment of the primer are separated by a linker region. The linker may be at least 10 nucleotides, at least 15 nucleotides, at least 20 nucleotides or at least 30, at least 40 nucleotides, at least 50 nucleotides or at least 60 nucleotides in length. Such a primer can form a single stranded loop and allow binding of additional primers during amplification (see also FIG. 6*d* and also FIG. 8*c*). Hairpin primers which contain such a linker sequence between the inverted repeats are referred to herein as "loop-providing primers" (LPPs). Such primers have not been described in the prior art and form a preferred aspect of the present invention.

LAMP, SMAP and SEA are explicit about the use of primers which generate an inverted repeat in the first generation amplicon which allows intra-molecular priming of the first generation amplicon. As a result, the first generation amplicon copies a section of itself and so generates a concatamer. The mechanism described for TRA is not explicit about the aforementioned mechanism. Nonetheless, TRA does produce concatamers and is likely to do so via the same mechanism as LAMP (See Example 1 and associated FIG. 7). The aforementioned intra-molecular priming is not the only mechanism available to the primers employed in these methods to generate concatamers, but regardless of the precise mechanism a rational for the beneficial effect of stem primers is apparent.

As discussed for the LFPs used in LAMP, TRA and SMAP for either intra- (FIG. 8*a*) or inter- (FIG. 8*b*) molecular self-priming of the first generation amplicon, the resulting next generation amplicon makes available single-stranded regions capable of binding the original primers used to generate the amplicon from the target template. It should be noted that the reciprocal strand of the single stranded loops formed are capable of binding the "loop primers" referred to below. The hairpin primers as described in SEA and SMAP do not generate such single stranded loops in amplicon. However, as discussed earlier, the inventors have realised that by using a variant of the SEA primer that contains a linker region between the inverted repeats (the LPPs shown in FIG. 6*d*), the hairpin primer may generate single stranded loops, as illustrated in FIG. 8*c*.

The ability of LFPs and LPPs to generate stable, single stranded regions of amplicon is critical to rapidly propagating further amplicon and represents a key aspect of technologies employing these primers. It means that concatameric amplicon can contain many new priming sites for the primers employed by the NAAT in question. In LAMP and TRA (and hence SMAP), the LFPs which generate inverted repeats in amplicon also provide for single stranded regions of amplicon which they can themselves bind to and so initiate further re-copy of amplicon and hence further propagate amplification. In LAMP and SMAP further additional primers may be used in addition to LFPs, which also bind to these single-stranded regions of amplicon to help further propagate amplification (known as loop primers). A facet of the present invention is that the stem primers do not bind to said stable single stranded loops generated by LFPs and/or LPPs but accelerate amplification via a distinct mechanism.

For LAMP, TRA & SEA (and by reference SMAP), it can be shown that the process of copying the next generation amplicon, whether via self-priming (irrespective of whether this is achieved intra- or inter-molecularly), binding and extension of a further primer from a single stranded region of amplicon or the actions of other primers binding either the forward or reverse reciprocal primer binding regions, makes the stem region of the next generation amplicon transiently single stranded. The suggested mechanisms of LAMP, TRA & SEA (and SMAP) anticipate that said single stranded stem region will be rapidly converted to double stranded polynucleotide either via the action of further amplicon self-priming and re-copying, or the action of primers binding to exposed binding sites for primers directed at either the forward or reverse reciprocal primer binding regions. The stem region is only ever expected to be transiently single stranded and not stably single stranded. Thus it was not expected that the stem region provides useful primer binding sites for amplification. However, it has now been surprisingly shown that primers directed at the stem region actually greatly increase the rate of amplification. The mechanism through which stem primers can bind to the amplicon is illustrated in FIGS. 9 and 10.

Whilst the action of stem primers is anticipated to be on transiently exposed single stranded polynucleotide resulting from amplicon re-copying, it is possible that other mechanisms could also account for the increased rate of amplification seen using stem primers. For example, it is possible that in a concatameric structure, one strand of polynucleotide can 'loop out' as in replication slippage, this is especially possible as concatameric polynucleotide structures, by their very nature, are capable of forming secondary structures between repeated sequences. The single stranded polynucleotide loops generated, could provide for binding sites for the stem primers, for example. Other mechanisms could also potentially explain the effect of stem primers but it is the principle of stem primers acting on concatameric polynucleotide sequences which is anticipated to be a common aspect of the present invention.

As discussed earlier, suitable reciprocal primers may comprise a first and a second segment wherein the first segment is substantially complementary to the reciprocal primer binding regions on the template. While this aspect of the invention is explained here in further detail with reference to the first primer, it is to be understood that the same principle applies mutatis mutandis to the second primer.

The term "substantially complementary" means that the first segment has sufficient complementarity to bind to the reciprocal primer binding region on the template and/or amplicon under conditions which are commonly used during NAATs. This requires that the first segment of the reciprocal primer has at least 70%, 80%, 90%, 95%, 99% or 100% complementarity to the reciprocal primer binding region on the template. The first segment of the reciprocal primer may be at least 5 nucleotides, at least 10 nucleotides, at least 20 nucleotides, at least 30 nucleotides, at least 40 nucleotides, at least 50 nucleotides, at least 60 nucleotides, or even at least 70 nucleotides in length.

Where the reciprocal primers further contain a second segment, the second segment comprises a sequence that is substantially complementary to another segment in the first primer or a region in the amplicon generated from the first segment of the first primer such that the second region is able to form a loop. "An amplicon generated from the first segment of the first primer" refers to the first copy of the template which is generated when the first primer is extended by a polymerase. Said amplicon includes the sequence of the first primer at its 5' end.

In some embodiments, the second segment is substantially identical to a region on the target template and/or the amplicon to which the primer binds. Such primers were referred to earlier as LFPs. "Substantially identical" means that the second segment has at least 70%, 80%, 90%, 95%, 99% or 100% identity to the region on the target template and/or the amplicon. It is also envisioned that only part of the second region shows substantial identity with a region on the target template. Regardless of whether the whole or only part of the second segment of the reciprocal primer shows substantial identity with a region on the target template, the region of the second segment which is substantially identical to a region on the target template and/or amplicon is at least 5 nucleotides, at least 10 nucleotides, at least 20 nucleotides, at least 30 nucleotides, at least 40 nucleotides, at least 50 nucleotides, at least 60 nucleotides, or even at least 70 nucleotides in length. In this aspect of the invention, once the first segment of the reciprocal primer has been extended to form a first amplicon, the second segment is able to bind to a complementary region within the same strand and thereby form a loop.

The second segment may also comprise a region which is substantially complementary to another region in the second segment. Such primers were referred to earlier as hairpin primers or loop-providing primers. "Substantially complementary" means that the two regions in the second segment have at least 70%, 80%, 90%, 95%, 99% or 100% complementarity to each other. Preferably, the region of complementarity will be at least 5 nucleotides, at least 10 nucleotides, at least 20 nucleotides, at least 30 nucleotides, at least 40 nucleotides, at least 50 nucleotides, at least 60 nucleotides, or at least 70 nucleotides in length. Where the primer is a hairpin primer, it is preferred that the two regions of complementarity in the second segment are separated by a short (i.e. less than 10 nucleotides) linker region in order to facilitate binding of the two regions to each other. The length of the linker region allows the skilled person to distinguish between LPPs with a linker region that is at least 10 nucleotides in length and hairpin primers whose linker region is less than 10 nucleotides in length. The first and the second segment of the primer may be connected via a linker region. In some embodiments the linker region is substantially identical to the first segment of said primer in order to allow the binding of further primers to the complement of the linker region once it is copied (FIG. 6d). "Substantially identical" means that the first segment has at least 70%, 80%, 90%, 95%, 99% or 100% identity to the linker region that connects the first and second segment of the primer.

The methods of the invention may be practised using forward and reverse reciprocal primers of the same kind, e.g. LFPs or hairpin primers. When referring to "the same kind of primers", it is meant that the primers are all simple primers, LFPs, LPPs or hairpin primers. The term "different kind of primers" accordingly relates to a combination of two or more primers wherein at least one of the primers is not of the same kind as the other primer(s). For example, where a method uses four reciprocal primers of which three are LFPs and one is a LPP, the primers would be considered to be of a different kind. Thus, it is also envisioned to use forward and reverse reciprocal primers which are not of the same kind. For example, a forward reciprocal primer may be used that is a LFP in combination with a reverse reciprocal primer that is a LPP or a hairpin primer. It is also possible to combine LFPs or hairpin primers with simple primers provided that the combination of primers results in the formation of a concatamer. Where the NAAT used for amplification employs more than one (i.e. two or more) forward and/or reverse reciprocal primer, it is also possible to combine the same or different kinds of primers on the same reciprocal primer binding site. In one aspect of the present invention, the two or more forward and/or reverse reciprocal primers are all LFPs. Suitable combinations of primers will be evident to those of skill in the art. For example, it will be evident to the skilled person that the combination of forward and reverse reciprocal primers that are all simple primers may not provide a mechanism to provide for the formation of a concatamer and therefore such a combination is not suitable for use in the present invention.

It is to be understood that, in general, the reciprocal primers, or sets of primers, act on different strands of the target template. Furthermore, the reciprocal primers (or one of each set of reciprocal primers) will act to delimit the region of the original polynucleotide copied and recopied. Thus exponential amplification requires the coupling of activities between at least two primer binding regions, a forward reciprocal primer binding region and a reverse reciprocal primer binding region (FIG. 1a). The forward and reverse primer binding regions may each comprise a single binding site for a primer whereby the reciprocal sites are on opposite sense strands i.e. one primer binding site is on the "forward strand", one on the "reverse strand" (as shown in FIG. 1a). The forward and reverse reciprocal primer regions may also comprise binding sites for two or more primers each, where more than two primers are employed by a particular NAAT. In this case, it is possible that the two or more primer binding sites in the forward and/or reverse reciprocal primer binding regions are all situated on the same strand of the target template and/or amplicon or on different strands of the target template and/or amplicon ((or copies thereof), FIG. 1b).

The stem primers of the invention may be positioned anywhere between the forward and reverse reciprocal primer binding regions provided that the binding site(s) of the stem primer(s) do(es) not significantly overlap with the forward or reverse reciprocal binding site. It is to be understood that in the case where a LFP is employed, where the LFP is a forward primer, the forward reciprocal primer binding region encompasses not only the F2 site (i.e. the forward reciprocal primer binding region) but also the F1 site (i.e. the region on the forward strand which is substantially identical to the second segment of the LFP), and where the LFP is a reverse primer, the reverse reciprocal primer binding region encompasses not only the R2c site (i.e. the reverse reciprocal primer binding region but also the R1c site (i.e. the region on the reverse strand which is substantially identical to the second segment of the LFP; FIG. 1e and FIG. 14). In this way the stem primers may be positioned anywhere between the R1(c) and F1(c) sites where two LFPs are employed (as in LAMP and TRA); where a single LFP is employed in a particular NAAT, the stem primers may bind between either a R1(c) or F1(c) site and another reciprocal primer binding region occupied by a non-LFP.

It is possible to employ only one stem primer which binds either the forward or reverse polynucleotide strand as shown in FIG. 2a. Alternatively, two or more stem primers may be used which can bind either to reciprocal strands of the amplicon (FIG. 2b) or to the same strand (FIG. 2d). The methods of the present invention may be practised with one, two, three, four or more stem primers which can be used in any spatial combination and which may bind either the reverse or forward strand provided that the binding sites for the stem primers do not significantly overlap with the forward or reverse reciprocal primer binding regions or do not overlap at all (FIG. 2e). The stem primers may further bind to any part within the stem region. Thus, the stem primer(s) may have a binding site which is in close proximity to the forward or reverse reciprocal primer binding region (FIG. 2c). "Close proximity" means that the binding region of the stem primer and the reciprocal primer binding region are no more than 10 bp, 50 bp, 100 bp, 200 bp, 300 bp, 400 bp, 500 bp, 600 bp, 700 bp, 800 bp, 900 bp or 1000 bp apart.

The stem primers according to the present invention may be at least 5 nucleotides, at least 10 nucleotides, at least 20 nucleotides, at least 30 nucleotides, at least 40 nucleotides, at least 50 nucleotides, at least 60 nucleotides, at least 70 nucleotides, at least 80 nucleotides or at least 90 nucleotides in length.

The stem primers may be simple primers. However, it is also envisioned to use stem primers that are LFPs, hairpin primers, LPPs, chimeric primers, or other derivatives. Where more than one stem primer is used, the stem primers may be of the same kind or may be a combination of different kinds of primers. When referring to "the same kind of primers", it is meant that the primers are all simple primers, LFPs, LPPs or hairpin primers. The term "different kind of primers" accordingly relates to a combination of two or more primers wherein at least one of the primers is not of the same kind as the other primer(s). For example, the stem primers used may all be simple primers or they may be a combination of simple primers, LFPs and/or hairpin primers. In fact it is envisaged that stem primers can be usefully employed in derivatives of LAMP, TRA, SMAP or SEA which make use of a variety of primer variations to those presently employed, as exemplified in FIG. 20.

As outlined in the literature associated with TRA & SMAP, as well as several other sources, there is a great variety of possible combinations of "simple primers", LFPs, hairpin primers, RNA containing primers, nickase site containing primers and other novel primers which could be used in novel combinations to generate derivatives of the methods outlined in respective NAAT methods. Where said combinations result in methods which generate concatameric amplicon capable of self-copying to generate longer concatamers, stem primers are anticipated to be applicable.

For example, the inventors have noted that a major drawback of the displacement primers used in LAMP (which are designed to operate on the target template and the principal amplicon but not first generation amplicon or next generation amplicon) is that, should a displacement primer bind and extend from its site before the associated LFP has bound and extended on the target template, the principal amplicon generated from the displacement primer will occlude and block the binding of the LFP essential for exponential amplification and hence inhibit amplification. The inventors have shown that this effect can be, to some degree, mitigated if instead of using a 'simple primer' structure for the displacement primer, an LFP is used as the displacement primer (Example 5, FIGS. 15a and b). This is believed to be because LFPs can allow to some extent, for re-priming of the primer site (as described in the patent associated with the TRA technology) but mainly because an LFP would be capable of acting on first and next generation amplicon, as well as target template and principal amplicon, whereas the 'simple' displacement primers is principally expected to act on target template and principal amplicon only. Such a method as described in Example 5 is therefore entirely consistent with the use of stem primers. Similarly, a chimeric primer as described in ICAN and RDC could be used as a displacement primer (instead of a simple primer) to allow for re-priming of the displacement primer site so reducing the possibility of occluding the LFP binding site.

Further, since stem primers act to increase the rate of amplification of methods employing LFPs via the coupling of processes occurring at the forward and reverse reciprocal binding regions and since it has been taught in the literature that the LAMP method has an upper limit to the number of nucleotides separating the forward and reverse reciprocal binding sites for the LFPs employed (Notomi et al. Loop-mediated isothermal amplification of DNA, Nucleic Acids Research, (2000) Vol 28., No. 12, e63), the use of stem primers can clearly allow the forward and reverse reciprocal binding sites to be located further apart in the sequence than previously practicable (especially if several stem primers are employed). This can have great benefit when it is desirable to demonstrate that two regions of sequence occur together on a polynucleotide but where the distance between the two regions is too far to allow each respective region to be effectively used as a forward and reverse reciprocal binding region in the NAATs described herein.

Since use of stem primers can allow for the forward and reverse reciprocal binding regions to be much further apart than in their absence and still allow for effective amplification, the presence of two distinct sites on a polynucleotide can be established. Thus the invention provides a method for amplification of a polynucleic acid wherein the forward and reverse reciprocal primer binding regions are located at a distance such that synthesis of a polynucleic acid can occur only in the presence of the stem primer(s). This distance can be defined experimentally by performing two separate NAATs in parallel wherein the NAATs, the reagents and the amplification conditions used are identical except that stem primer(s) are added to one reaction but not the other. Where synthesis of the polynucleic acid occurs only in the presence of the stem primer(s), the reciprocal primer binding sites are considered to be located at a distance such that synthesis of a polynucleic acid can occur only in the presence of the stem primer(s).

For example, the mecA gene present in Methicillin-resistant Staphylococcus aureus (MRSA) may be situated a significant distance from the conserved orfX sequence associated with the insertion site for the SCCMec genetic mobile element associated with MRSA (see WO02/099034). The use of stem primers can help to detect MRSA by allowing the mecA gene and the orfX sequence to act as reciprocal binding sites for amplification, even if they are too distant in sequence to use methods such as LAMP. Thus, in one aspect, the present invention provides a method for the detection of MRSA in a sample.

The stem primers may contain exclusively naturally occurring nucleic acids. However, it is also envisioned to utilise primers that contain modified bases. Examples of such modified bases include, but are not limited to, N4-methylcytosine, inosine, ribocleotides, fluorescent bases, photolysable bases or universal bases. It is also envisioned to use nucleic acids that have been labelled with a moiety that allows the stem primer and/or the amplicon to which the labelled stem primer binds to be detected. For example, the nucleic acid may be fluorescently labelled. The stem primers may alternatively be labelled with capture moieties (e.g. biotin).

Importantly, the stem primers are not directly responsible for exponential amplification of the amplicon, which is mediated by the primers binding to the forward and reverse reciprocal primer binding sites, but merely increase the rate of amplification. This is because the stem primers are considered to function on the amplification products of the other primers employed by a particular NAAT. Hence, stem primers function by increasing the amplification rate of the reaction mediated by the forward and reverse reciprocal primers. This is shown in FIG. 1c, where it can be seen that were the stem primer to prime and extend from the target template, the partial copy of the target template would contain only either the forward reciprocal primer binding region or the reverse reciprocal primer region, but not both. Therefore, the principal amplicon generated from a stem primer would not allow for reciprocal copying and hence would not contribute to exponential amplification of the target template (this is shown in detail in FIG. 21). The same argument applies to stem primers copying a principal amplicon generated by other primers employed by a particular NAAT and similarly for first generation amplicons.

Stem primers are only anticipated to significantly increase the rate of amplification of a target template if the next generation amplicon (i.e. further copies of the first generation amplicon (and copies of these copies)) is concatameric in nature. The requirement for stem primers to work on concatamers follows from the requirement that for a particular polynucleic acid to contribute to exponential amplification it must contain regions capable of acting as the forward and reverse reciprocal primer binding regions. It can be clearly seen from FIG. 21 that copying of a concatameric structure via a stem primer, can produce a polynucleotide copy which has both forward and reverse reciprocal primer binding sites, whereas copying a non-concatameric structure does not. Thus, the inventors expect that the use of stem primers will be beneficial for amplification methods that result in the formation of concatamers.

It has been found that the stem primer(s) work(s) in a coupled fashion with the other primers used in the NAAT and this interaction is critical for obtaining the observed large increases in amplification rate. The increased rates of amplification seen using stem primers cannot be explained by virtue of the stem primers participating in an additional but distinct amplification process whereby the amplicon produced via one stem primer does not act as a template for all the other primers being employed by a particular NAAT to recopy amplicon. The inventors have experimentally and theoretically demonstrated that the observed increased rates of amplification must result from a single, coupled amplification process rather than two or more distinct amplification processes whereby amplicon produced from one process cannot act as a template for amplicon produced from another process. Examples of the type of very substantially increased rates of amplification for the amplification technology TRA are demonstrated in Example 2 for a variety of primer sets with different amplification kinetics. In each case, the stem primers significantly increase the rate of amplification and, in so doing, increase the sensitivity of the test within the timeframe that the tests are performed (FIG. 11). Thus, the stem primers may decrease the time required to detect a particular type and amount of target template by at least 1 minute, at least 2 minutes, at least 3 minutes, at least 5 minutes, at least 10 minutes, at least 20 minutes, at least 30 minutes or at least 60 minutes compared to a control reaction to which no stem primer(s) has/have been added.

A manifestation of TRA has been described, for example, that uses a simple primer in conjunction with a LFP where it is understood that each primer, reciprocally, binds either the forward or reverse reciprocal primer binding regions (U.S. Pat. No. 6,743,605). This combination is referred to herein as Asymmetric TRA, or ATRA. As such, when stem primers are added to TRA, one could argue that there are now three separate amplification processes combined in the one assay, one being TRA and then two separate ATRA amplifications (FIG. 12a). It could therefore be tempting to suggest that stem primers do not increase the rate of amplification of TRA per se but simply add two additional ATRA amplifications to the same assay. However, if this was the case, then the observed overall rate of amplification would be the sum of the rate of amplification of the TRA system plus that of both the ATRA systems. However, the inventors have shown that the use of stem primers causes an increase in amplification rate far greater than would be expected from the sum of substantially independent amplification systems. In Example 3, the rate of amplification is measured with different combinations of stem primers and LFPs. The manifestations using a single stem primer and a single LFP are equivalent to ATRA. It can be seen that the rate of amplification using the two possible combinations of stem primer and LFPs (i.e. the two manifestation of ATRA) give extremely slow kinetics (FIG. 12b (i and ii)). The kinetics when the two LFPs are used together (i.e. a TRA system) are faster than the two ATRA systems (FIG. 12b(iii)). When the stem primers and LFPs are combined together, the rate of amplification is substantially faster than any of the previous manifestations of TRA or ATRA (FIG. 12b(iv)). Given how slow the ATRA kinetics are shown to be (and remembering the exponential nature of amplification), it is not reasonable to surmise that the increased rate of amplification shown in FIG. 12b(iv) is simply a sum of the rate of reactions for the two ATRA and TRA systems combined. This underlines the fact that stem primers are acting in a coupled fashion with the other primers involved in exponential amplification and, again, this can be rationalised by the action of stem primers on concatamers which produces copies of amplicon that retains a forward and reverse reciprocal primer binding region.

The empirical example above can also be modelled. In Example 4, three separate amplification processes are modelled with mathematically defined amplification rates. The model gives the output as BART curves (see below). The parameters used reflected the range of results the Inventors had obtained for the rates of different manifestations of isothermal NAATs. It can be seen that if, e.g. two very slow amplification processes are summed with a much faster amplification process, one does not observe the type of significantly faster amplification that is observed when stem primers are added to either LAMP, LAMP+loop primers or TRA (compare the results of the model in FIG. 13a with the empirical results shown in FIGS. 11, 12b, 15, 16 and 17 from Examples 2, 3, 5, 6 and 7 respectively). Further, FIG. 13b, showing the result of summing a fast amplification process with two moderately fast amplification processes, demonstrates that even under such conditions, the type of substantially increased rates of overall amplification seen using stem primers are not observed in the model. In fact, as evident in FIG. 13c, even where three fast amplification processes are summed, the overall amplification rate is only very slightly faster than any of the individual processes: this reflects the exponential nature of amplification (compare to FIGS. 11, 12b, 15, 16 & 17 from Examples 2, 3, 5, 6 & 7 respectively).

The increased rate of amplification that stem primers can provide has been demonstrated with, or anticipated to work with, several isothermal NAATs. Examples of where stem primers can be deployed relative to the other primers employed in a particular NAAT are shown in FIG. 14a-g. Examples 5, 6, & 7 demonstrate empirical data for several of the NAAT manifestations shown in FIG. 14. In each case significant increases in amplification rate can be seen (FIGS. 15-17).

A further utility of stem primers in concatamer forming NAATs could be as probe for use in a fluorescent, chemiluminescent, electrochemical or other reporter system as a means to follow the extent of amplification in 'real-time'. Stem primers could have benefit as probe containing primers over e.g. LFP or hairpin primers since they are not required to generate inverted repeats in amplicon which could affect certain types of probes.

The target template used in the present invention may be any polynucleic acid that comprises suitable reciprocal primer binding regions that allow for amplification of a polynucleic acid of interest. The skilled person will understand that the forward and reverse reciprocal primer binding sites need to be positioned in such a manner on the target template that the forward reciprocal primer binding region and the reverse reciprocal primer binding region are positioned 5' of the sequence which is to be amplified on the sense and antisense strand, respectively.

The target template may be single or double stranded. Where the target template is a single stranded polynucleic acid, the skilled person will understand that the target template will initially comprise only one reciprocal primer binding region. However, the binding of the first primer will result in synthesis of a complementary strand which will then contain the second reciprocal primer binding region.

The target template may be derived from an RNA molecule, in which case the RNA needs to be transcribed into DNA before practising the method of the invention. Suitable reagents for transcribing the RNA are well known in the art and include, but are not limited to, reverse transcriptase.

In addition to the forward and reverse reciprocal primer binding regions, the target template needs to comprise a stem region that needs to have a sufficient length to allow binding of the one or more stem primers of the invention. Thus it is preferred that the stem region has a length of at least 5 nucleotides, at least 10 nucleotides, at least 15 nucleotides, at least 20 nucleotides, at least 30 nucleotides, at least 50 nucleotides, at least 100 nucleotides at least 200 nucleotides, at least 300 nucleotides or at least 500 nucleotides.

The skilled person will be aware that, in addition to the primers needed for amplification, the NAATs will require further reagents in order to synthesize a polynucleic acid. The required reagents will be evident to the person skilled in the art but will generally include a suitable buffer, dNTPs, a polymerase, etc.

As the skilled person will appreciate, following addition of all the necessary components for performing the NAAT in question, it is necessary to provide suitable conditions for the synthesis of the polynucleic acid. This can be achieved by providing a suitable incubation temperature, for example. It is preferred that amplification occurs under isothermal conditions. This means that during amplification the temperature is kept constant. "Constant" means that the temperature varies by no more than ±10° C. However, methods that encompass a single temperature change of greater than 10° C., two temperature changes of greater than 10° C., three temperature changes greater than 10° C., four temperature changes greater than 10° C. or five temperature changes greater than 10° C. during the amplification process are also within the scope of the present invention.

The amplification of the polynucleic acid according to the invention may be detected by methods known to those of skill in the art. Suitable methods include but are not limited to the use of fluorescent intercalating dyes, fluorescent primers or probes, measuring turbidity, electrochemical probes, bioluminescent signals and chemiluminescent probes.

The amplification of the polynucleic acid may be detected using real-time methods, i.e. methods that can detect the polynucleic acid as it is amplified. Examples of such detection systems include, but are not limited to, fluorescence (e.g. fluorescent probes that are added during the amplification), bioluminescent signals and electrochemical probes. In one aspect, the stem primers themselves are labelled with a detectable moiety, e.g. a fluorescent label, a chemiluminescent label or an electrochemical label, that allows detection of the amplicon to which the stem primer(s) bind(s). Thus, a further utility of stem primers in concatamer forming NAATs could be as probe for use in a fluorescent, chemiluminescent or electrochemical reporter system as a means to follow the extent of amplification in 'real-time'. Other suitable reporter systems will be evident to those of skill in the art. Stem primers could have benefit as probe containing primers over e.g. LFP or hairpin primers since they are not required to generate inverted repeats in amplicon which could affect certain types of probes. Alternatively, the amplification product may be detected using end-point measurements, i.e. measurements which take place after the amplification of the polynucleic acid has been completed.

The amplification of the polynucleic acid can also be detected by other detection methods employed in NAAT detection. Suitable examples include, but are not limited to, gene arrays, lateral flow strips, electrophoresis, mass spectroscopy and acoustic detection.

In one embodiment the Bioluminescent Assay in Real-Time (BART) reporter system is used to detect the synthesis of the polynucleic acid. This system has been explained in detail in WO2004/062338 and WO2006/010948, which are hereby incorporated by reference. BART is an example of a reporter system designed for isothermal NAATs which gives a single type of signal from a sample: a bioluminescent signal. BART utilises the firefly luciferase-dependent detection of inorganic pyrophosphate: this is produced in large quantifies when 'target' sequences are amplified using a NAAT. As such, molecular diagnostics can be achieved with BART simply by measuring the light emitted from closed tubes, in a homogeneous phase assay. BART is proven with several different NAATs, operating between 50-63° C. The BART reporter is a particularly effective means to follow the rate of amplification of a NAAT since the light output represents a measure of the instantaneous rate of amplification (whereas, e.g. fluorescent outputs show the accumulation of a signal and hence the measurements have to be differentiated to obtain the amplification rates). By way of example, FIG. 22 shows BART being used in conjunction with LAMP to detect a dilution series of a particular target DNA molecule. Note that as the amount of target DNA in the sample decreases, the lag-phase to reach the time of maximal light increase (which is proportional to the lag-phase to reach maximal amplification) increases. Put differently, the time to reach the characteristic light peak associated with positive samples in BART increases in inverse proportion to the amount of target polynucleic acid in the sample. It is stressed that whilst the examples make use of the BART reporter system, the present invention is not limited to the use of BART and is equally applicable to methods such as fluorescence, turbidity, other spectroscopic techniques or electrochemical measurement methods irrespective of whether these are employed in real-time measurement of amplification or as end-point measurements.

Preferably, the method of the invention is performed in a sealed vessel. This is of great utility since it reduces or even prevents the possibility of the sample becoming contaminated. Moreover, it reduces or even prevents the possibility of the laboratory becoming contaminated. This is particularly important as if even one copy of the template polynucleic acid or amplicon were to escape into the laboratory, this could potentially contaminate other samples to be tested and give false-positive results. Thus, the ability to prevent contamination is of particular importance where a method of the invention is used in a diagnostic application.

A further application of a method according to the invention is for determining whether a particular polynucleic acid sequence is present in an organism's genetic code. For example, it could be used for determining whether the nucleic acid to which the template nucleic acid originates has been genetically modified, for detection of DNA associated with a particular non-genetically modified breed of plant or a genetically modified plant, for detection of DNA associated with pedigree breeds of animal or for medical or veterinary diagnostic applications such as genetic testing or forensic. The methods of the present invention are also suitable for the detection of single-nucleotide polymorphisms (SNPs).

A method according to the invention may be used in diagnostic applications. In particular the method allows identification and quantification of organisms in a patient and other samples. The organism may be any micro-organisms, such as viruses, bacteria, mycoplasma and fungi. The micro-organism can be pathogenic but it may also be a non-pathogenic micro-organism. The microorganism may also be a genetically modified organism (GMO). Furthermore, the methods of the present invention can be used to identify genetically modified crops and animals, for the detection of a disease state; for the prediction of an adverse reaction from a therapy and also for the prediction of a disease state susceptibility.

"Patient sample" refers to any sample taken from a patient and can include blood, stool, swabs, sputum, Broncho Alveolar Lavage Fluid, tissue samples, urine or spinal fluids. Other suitable patient samples and methods of extracting them are well known to those of skill in the art. A "patient" or "subject" from whom the sample is taken may be a human or a non-human animal. When a sample is not specifically referred to as a patient sample, the term also comprises samples taken from other sources. Examples include swabs from surfaces, water samples (for example waste water, marine water, lake water, drinking water), food samples, cosmetic products, pharmaceutical products, fermentation products, cell and micro-organism cultures and other samples in which the detection of a micro-organism is desirable.

In a further aspect, there is provided a kit for use in a method according to the invention. Preferably such a kit comprises all the components necessary to practise the method of the invention, except the target polynucleic acid which is to be tested, unless the target polynucleic acid forms part of a supplied positive control.

A kit for use in a method according to the invention preferably comprises a polynucleic acid polymerase, the substrates for the nucleic acid polymerase and primers suitable for isothermal amplification of the target polynucleic acid, as described earlier. More preferably, the kit further comprises buffer reagents, such as a source of magnesium ions, or additives known in the art to improve the performance of a NAAT such as Betaine or additives known to improve the shelf-life of kit reagents such as trehelose or additives known to help preserve reagents such as sodium azide. Alternatively, a kit for use in a method according to the invention may comprise only some of these components and/or additional components. The sample and any other components that have been omitted from the kit may then be added to the kit during use.

When BART is used for detection of the polynucleic acids, a thermostable luciferase, luciferin and an enzyme that converts inorganic pyrophosphate (PPi) to ATP, such as ATP sulphurylase, and any other required substrates or cofactors of the enzyme that converts PPi to ATP, such as adenosine 5' phosphosulphate, may be included in the kit. Thus in one embodiment a kit for use with BART comprises nucleic acid polymerase, b) at least one stem primer, c) at least two reciprocal primers suitable for isothermal amplification of the test sample, d) a thermostable luciferase, e) luciferin, f) ATP sulphurylase, and g) adenosine 5' phosphosulphate.

Preferably, at least one of the components of the kit is lyophilised or is in another form which is suitable for storage in the kit. More preferably, all of the components of the kit are lyophilised or in one or more other forms suitable for storage. Such other forms include components to which stabilising factors have been added and/or a refrigerated or frozen mastermix that contains the components of the kit.

General

The term "about" in relation to a numerical value x is optional and means, for example, x±10%.

The term "comprising" encompasses "including" as well as "consisting" e.g. a composition "comprising" X may consist exclusively of X or may include something additional e.g. X+Y.

BART refers to a method for determining the amount of template polynucleic acid present in a sample wherein the presence of inorganic phosphate which is derived from the amplification reaction is detected and is indicative of the amount of template polynucleic acid in the sample.

Various aspects and embodiments of the present invention will now be described in more detail by way of example. It will be appreciated that modification of detail may be made without departing from the scope of the invention.

DESCRIPTION OF FIGURES

Depicts the two regions on a polynucleotide generally required for exponential amplification whether using just two primers (FIG. 1a) or several primers (FIG. 1b). With reference to these regions, the stem region of the polynucleotide, the subject of the present invention, is defined in FIG. 1c.

Depicts various means by which one, two or more stem primers can be positioned in the stem region.

FIG. 3

Figure 1A:
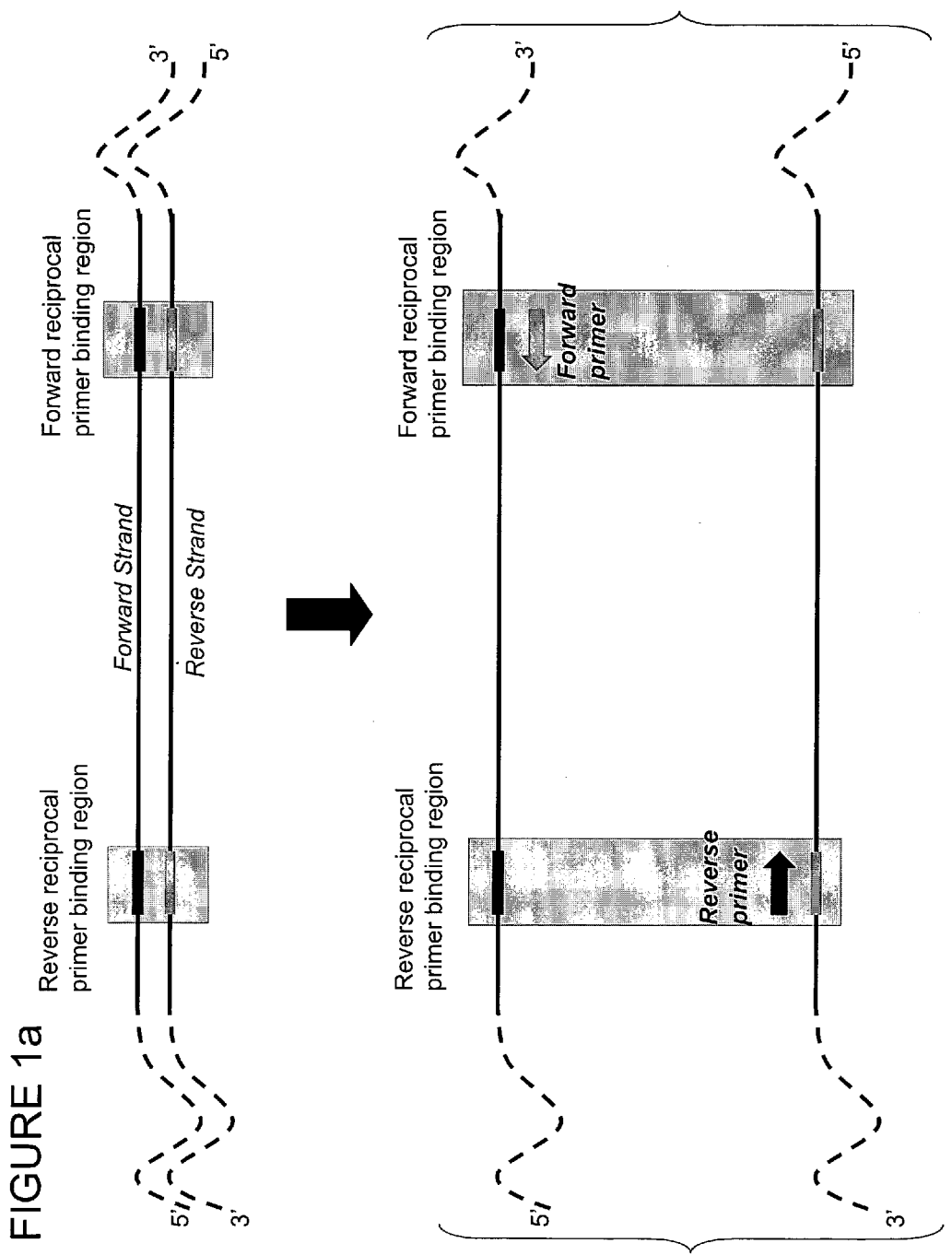
FIG. 1
FIG. 1d explicitly shows the stem region for the NAATs referred to herein as LAMP and TRA in expected first generation amplicon formed by these methods; this shows that the stem region lies between the regions of the amplicon involved in forming intra-molecular loops. Note that, in fact, whilst LAMP and TRA represent their first generation differently (in their associated patent applications) the structures are in fact identical.
FIG. 1e explicitly shows the stem region for the NAATs referred to herein as LAMP and TRA on the target template.
Figure 1B:
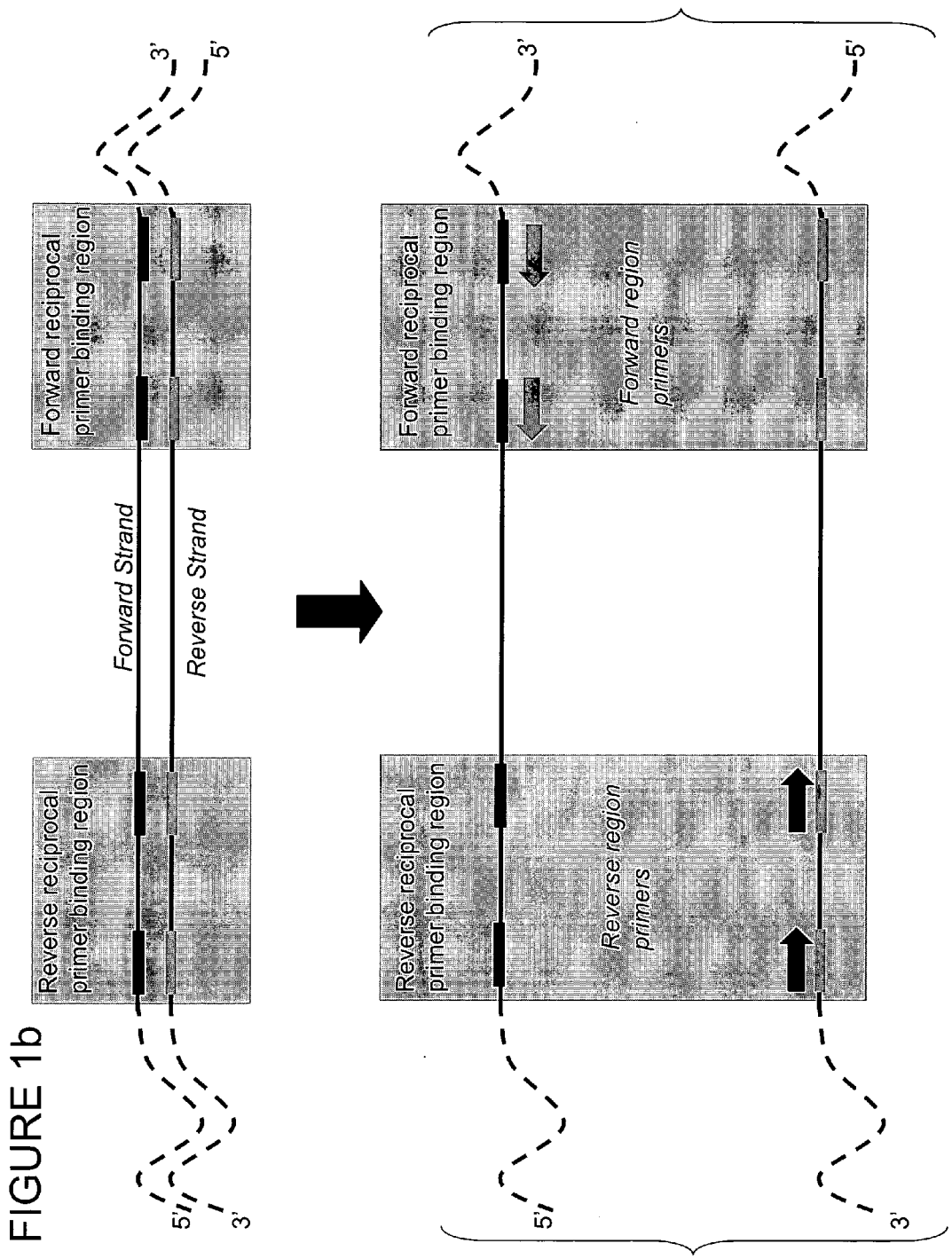
Figure 1C:
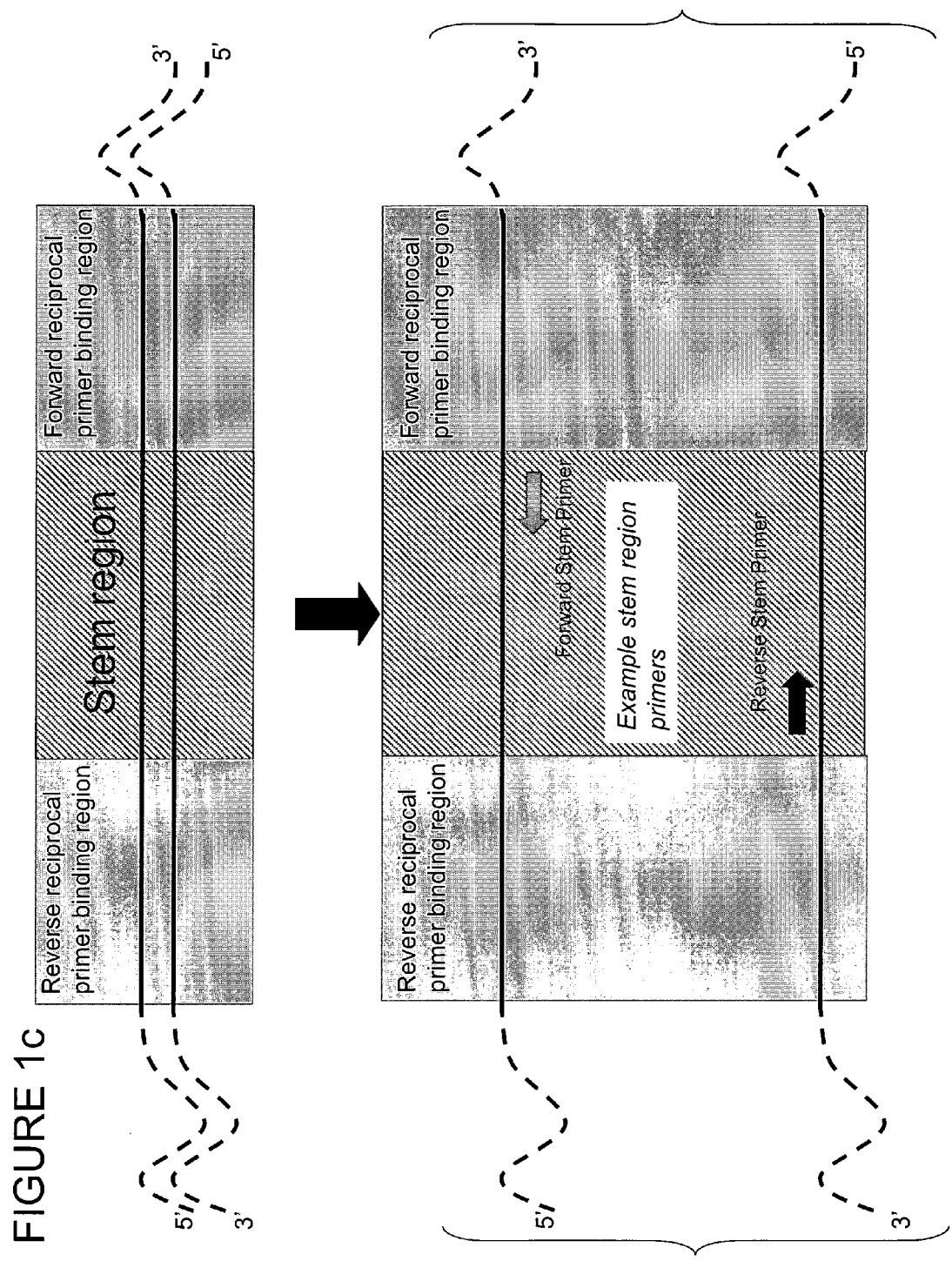
Figure 1D:
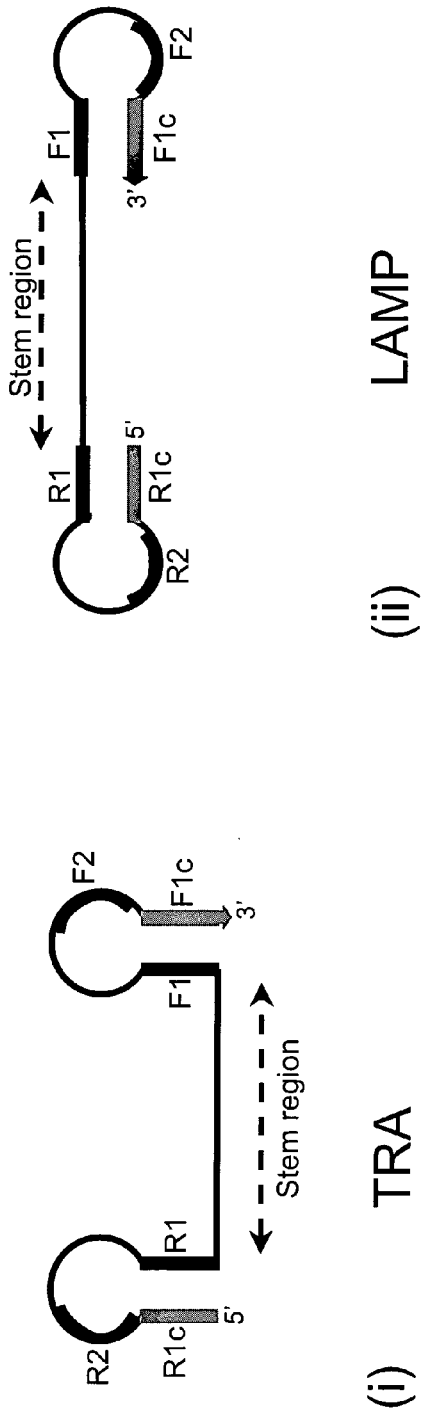
Figure 1E:
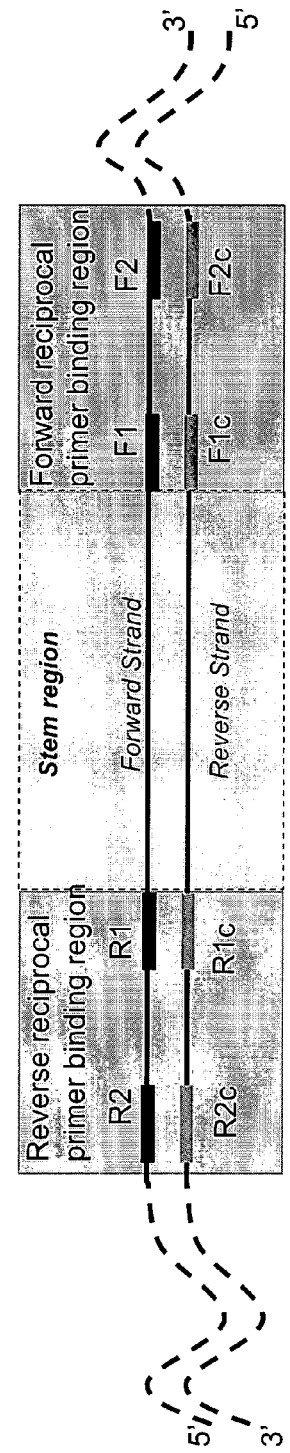
Figure 2A:
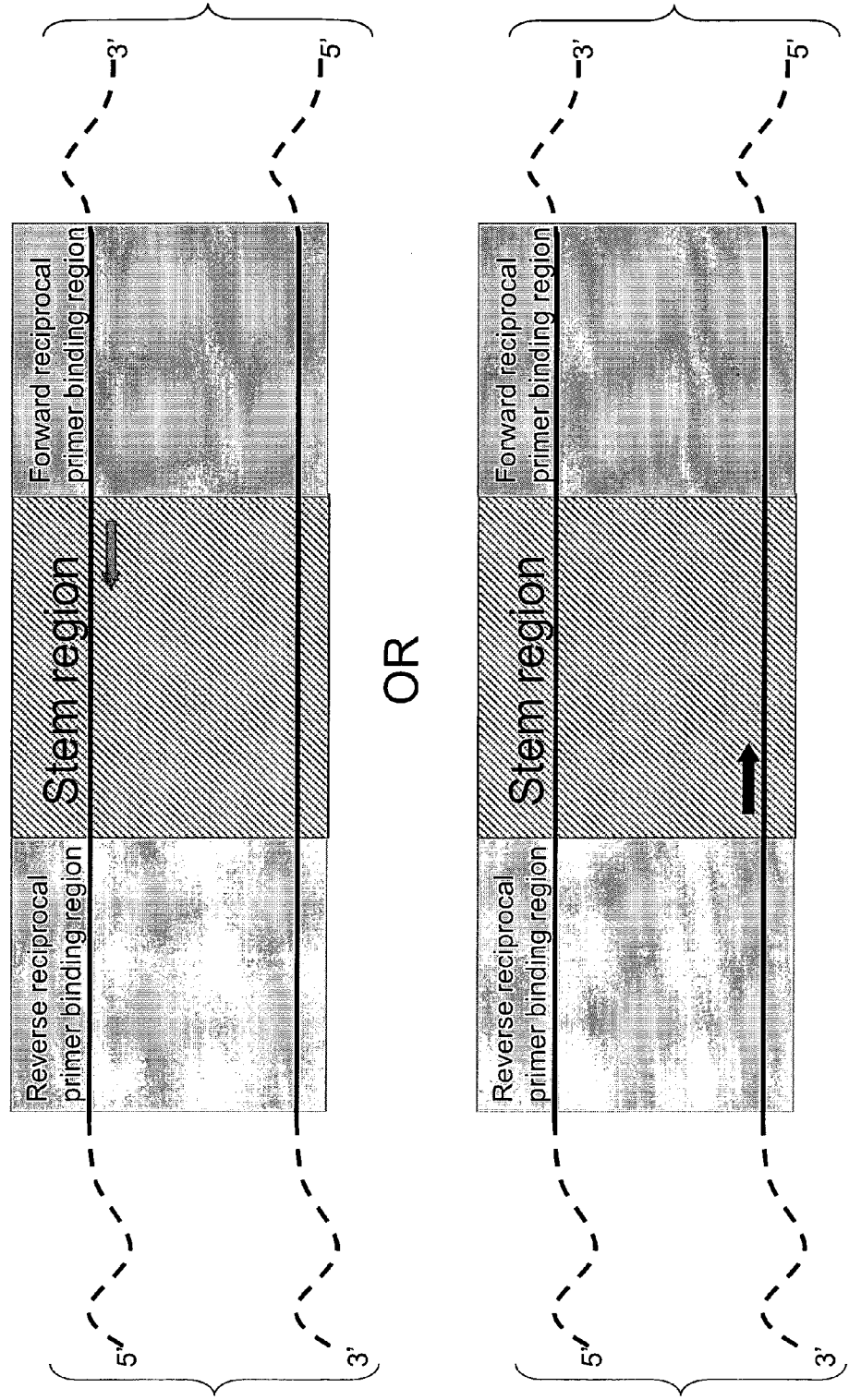
FIG. 2
Figure 2B:
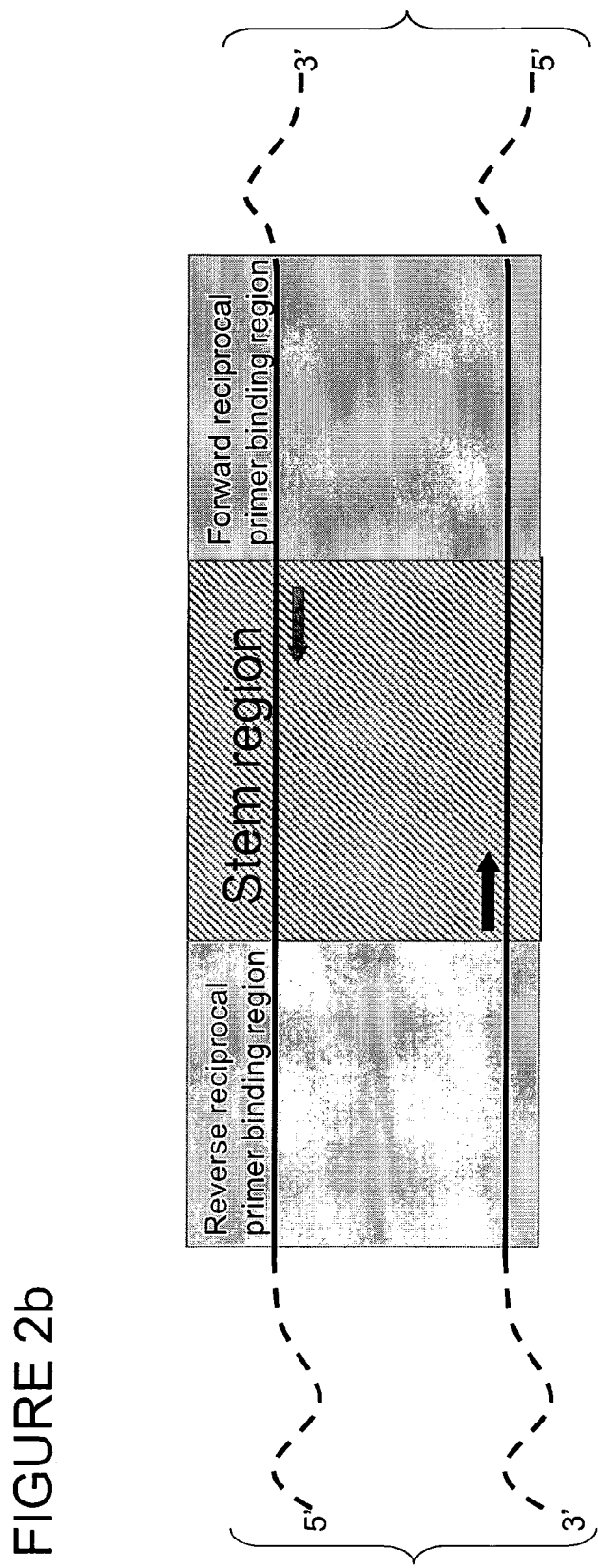
Figure 2C:
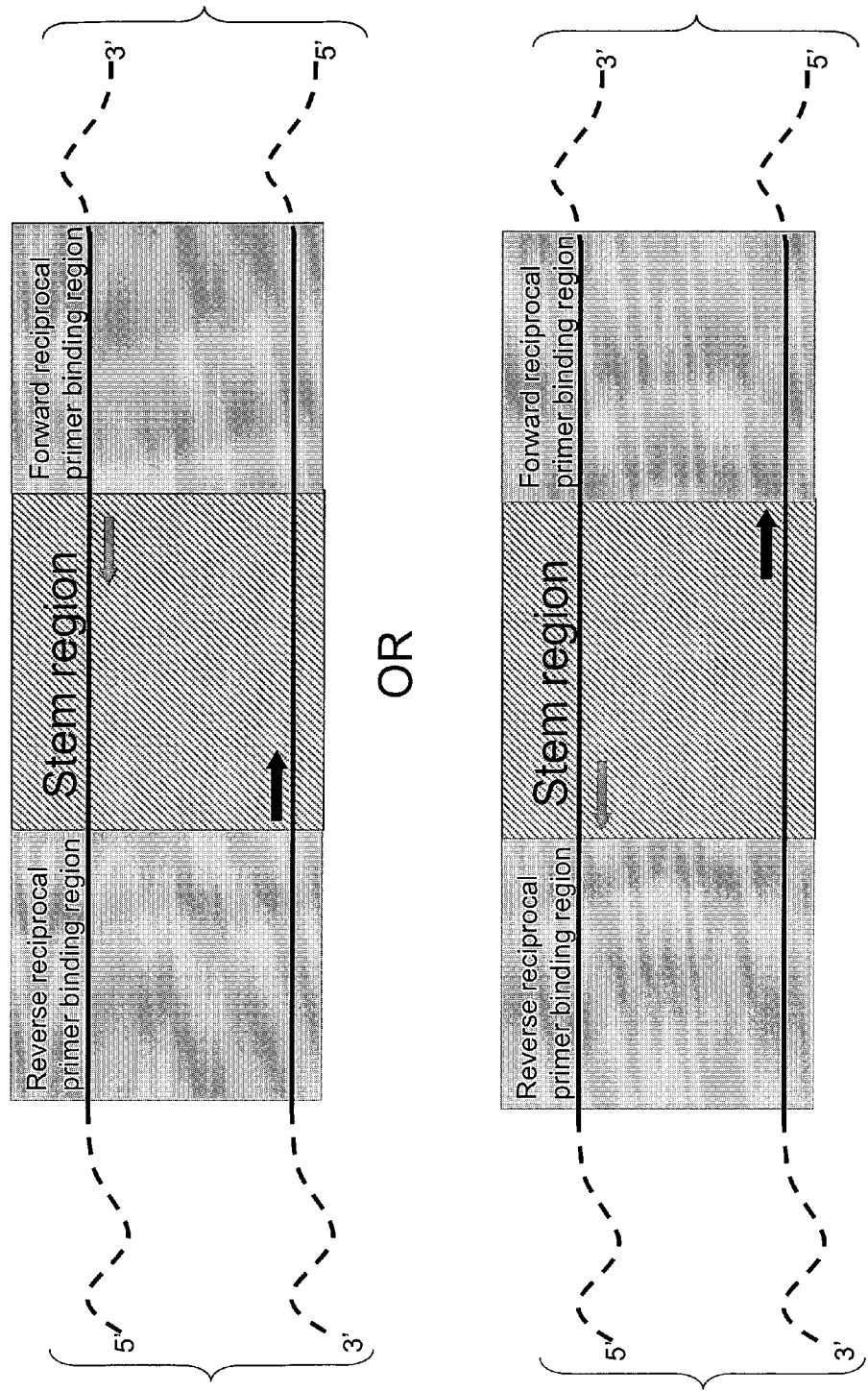
Figure 2D:
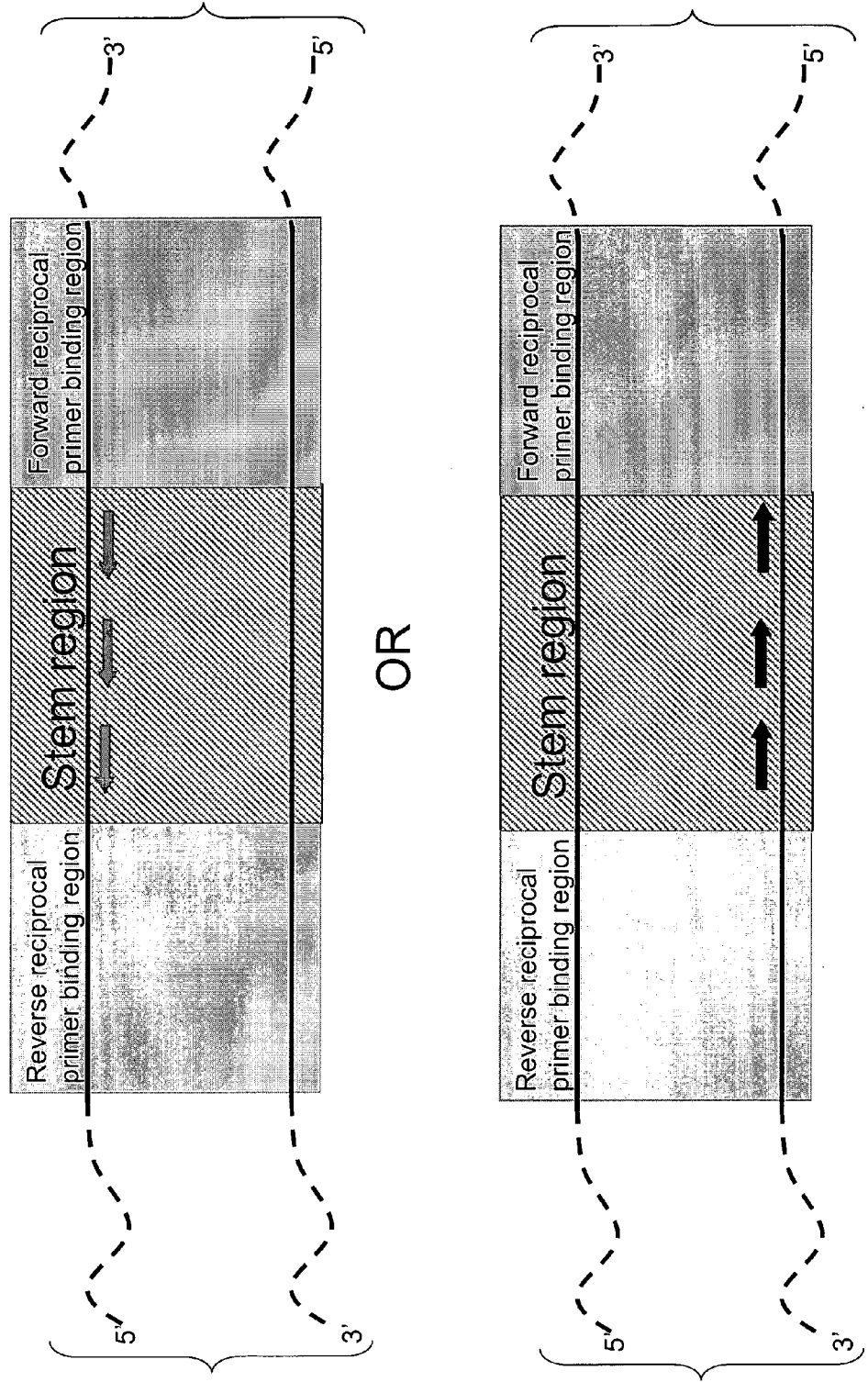
Figure 2E:
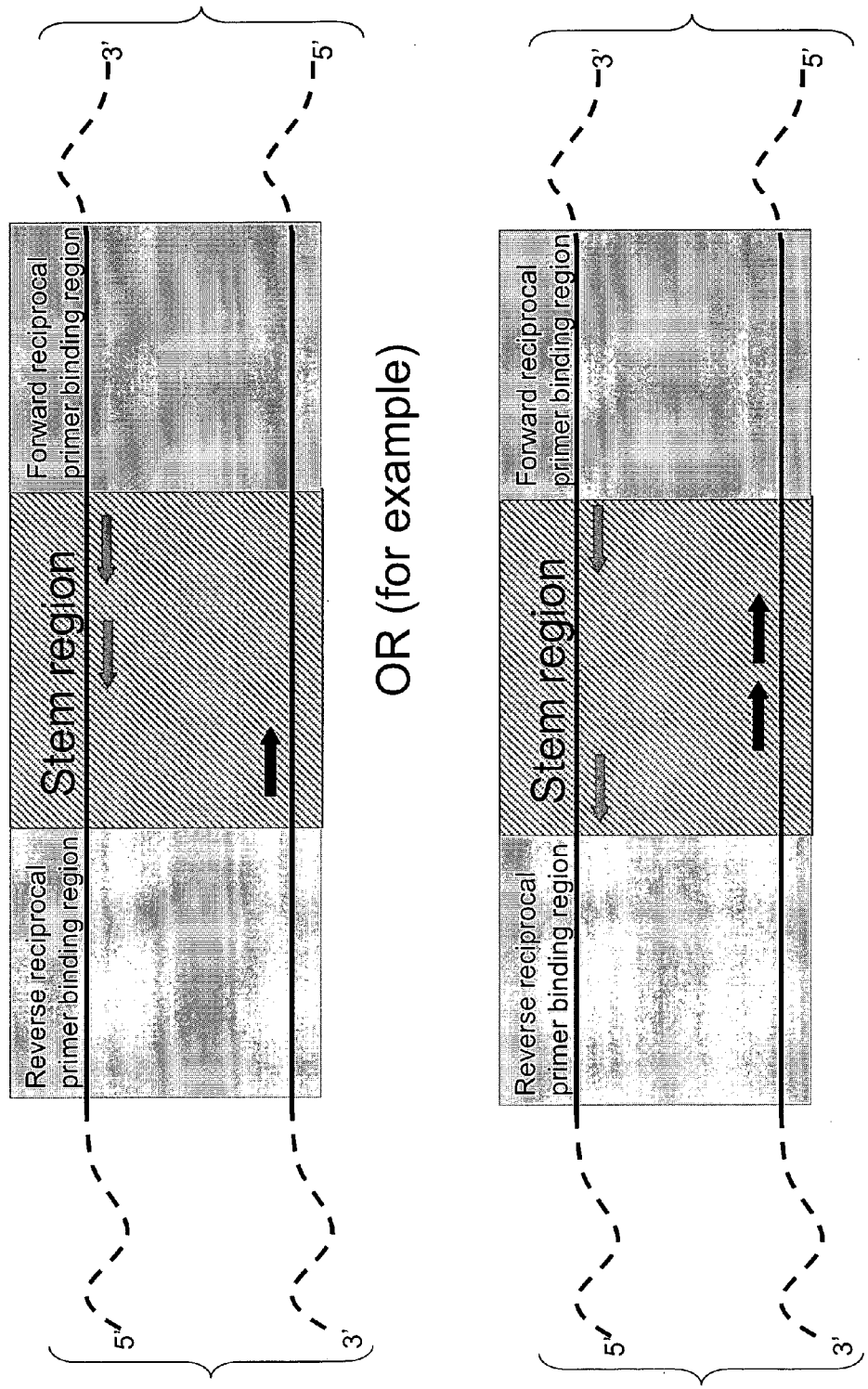
Figure 3A:
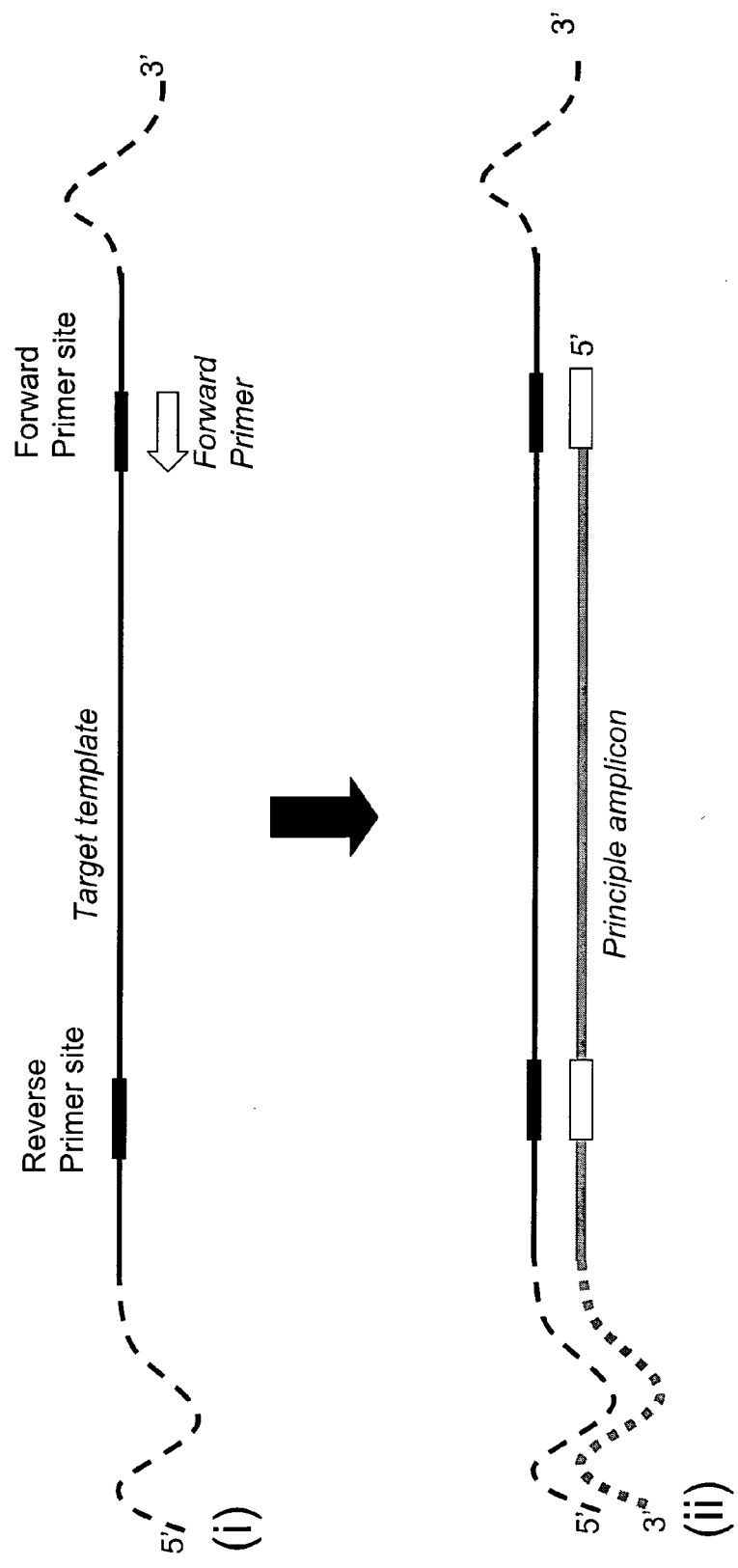
Figure 3B:
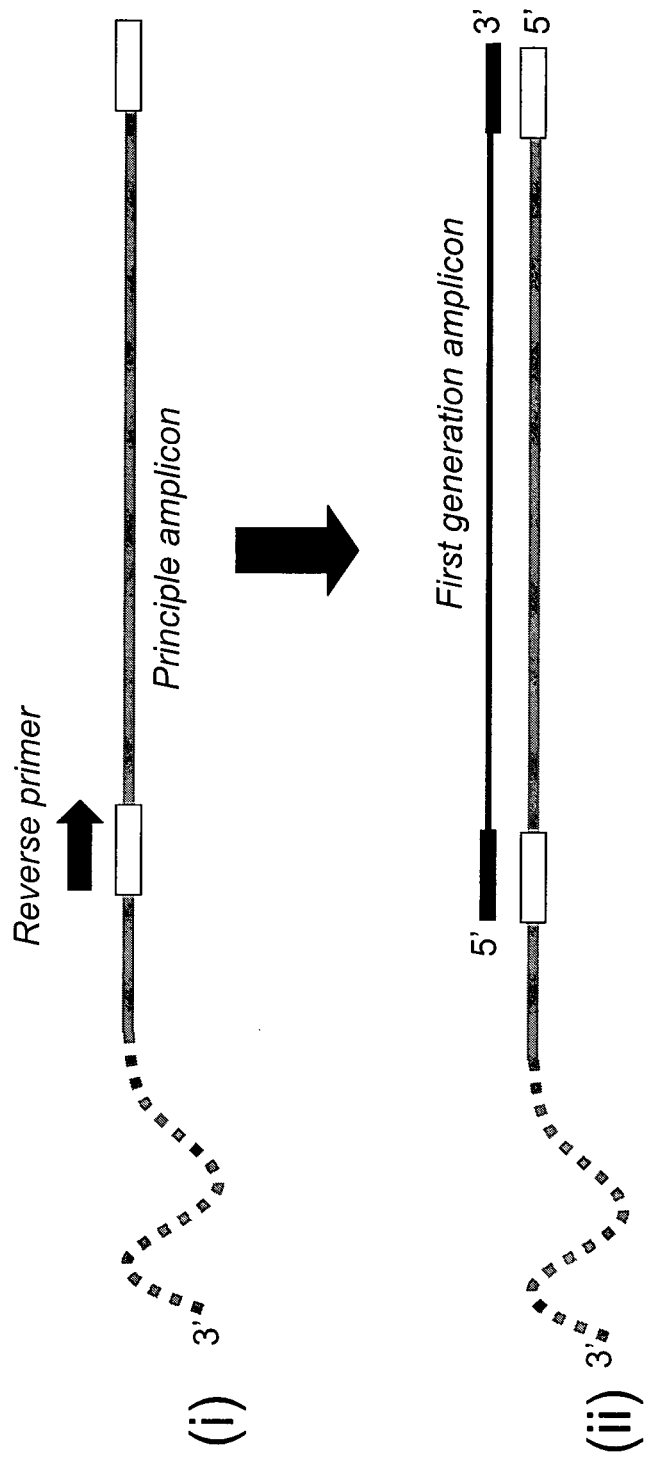
Figure 3C:
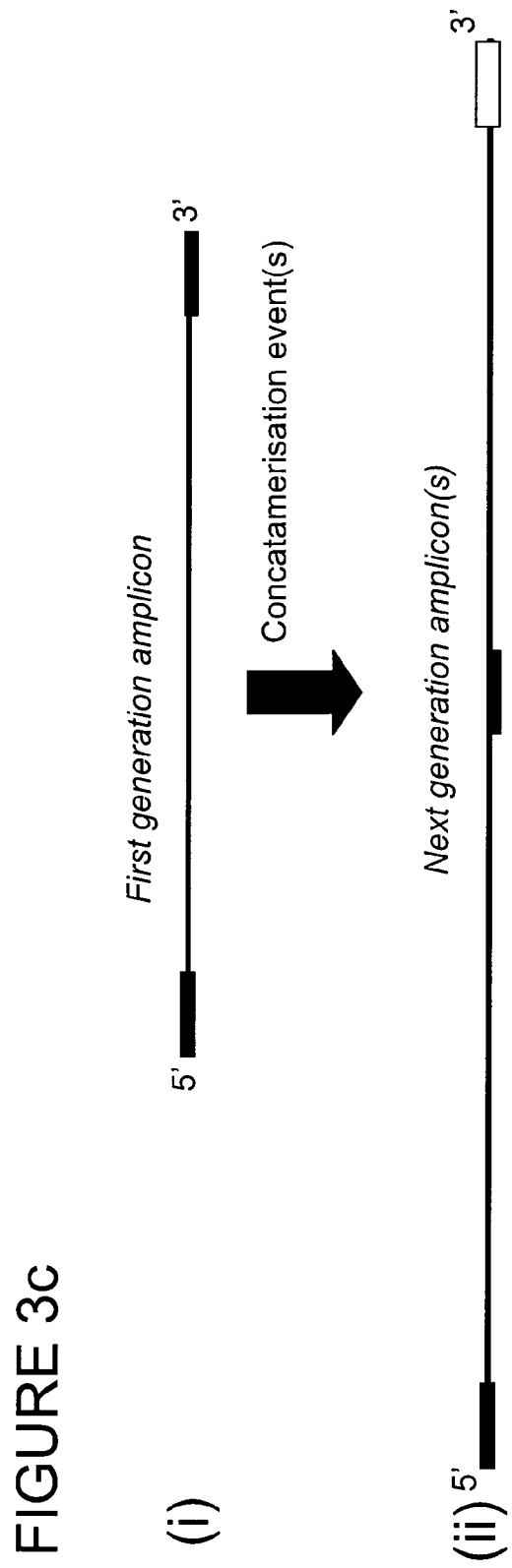

Depicts the generation of various types of amplicon as referred to herein including the generation of principal amplicon (FIG. 3a), first generation amplicon (FIGS. 3b) and next generation amplicon (FIG. 3c).

FIG. 4

Depicts the process by which LFPs can form concatameric structures. In the first instance, a principal amplicon is formed which has an inverted repeat at its 5' end (FIG. 4a), hence inspection of FIG. 4a(ii) shows that from the 5' end of the principal amplicon, there is an F1 region, and further along the amplicon there is now, in the same strand, a complement to this region, F1c (the small c in this and the following figures will denote the complement of a primer binding region). The mechanisms provided by a particular NAAT to make the principal amplicon single stranded and available for copying by another primer are not made explicit in FIG. 4a but are represented by the two black arrows leading to FIG. 4a(iii) where the resultant first generation amplicon is shown.

Figure 4B:
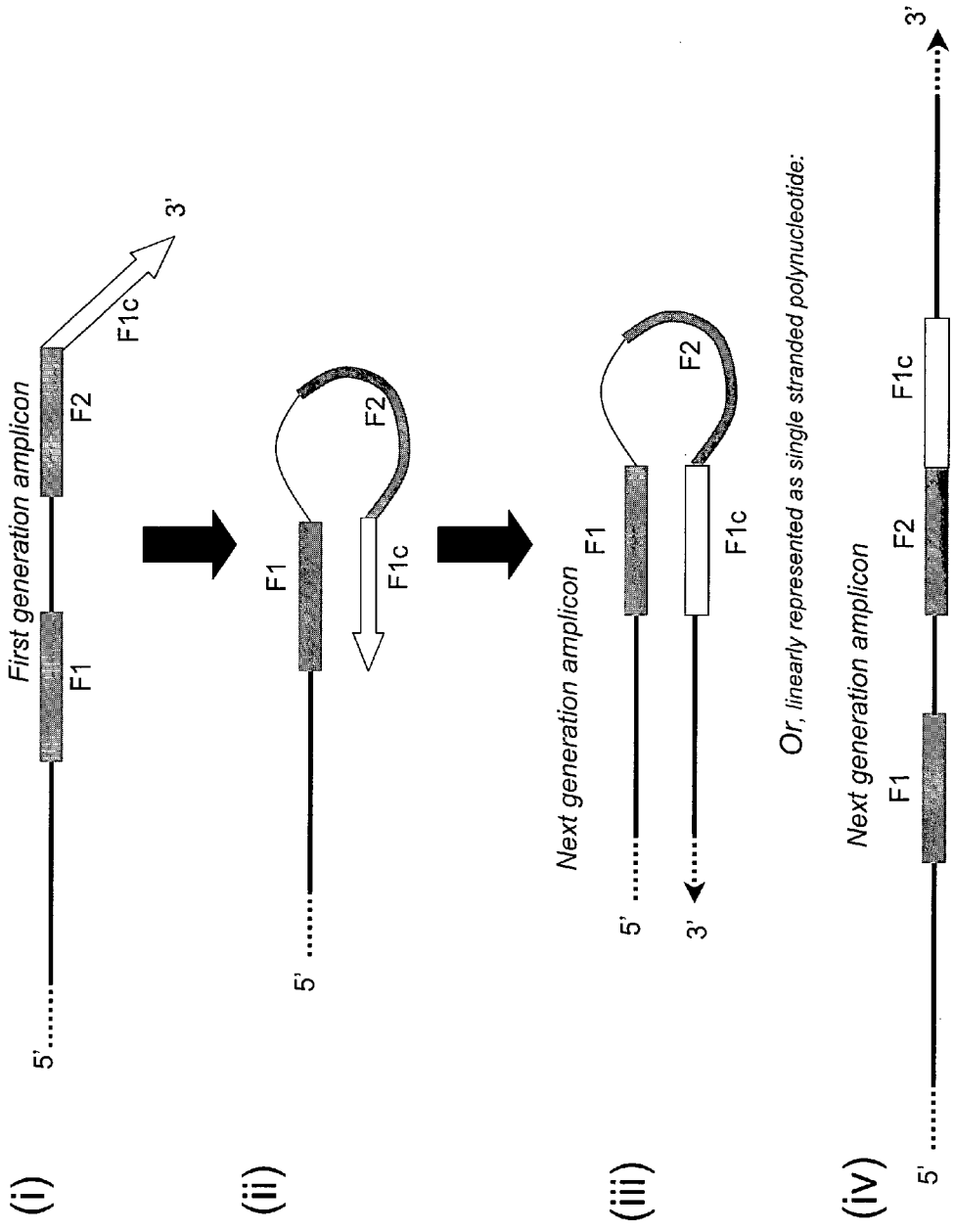

The first generation amplicon formed by LFPs can itself act as a primer to generate further amplicon. In so doing it can form concatameric structures. There are two general mechanisms by which the concatamers can form, one via an intra-molecular event, as shown in FIG. 4b and one an inter-molecular event as shown in FIG. 4c. Note that in both cases, the process generates single stranded regions of amplicon within the concatamer, see region F2 in FIGS. 4b(ii) and (iii) and 4c(ii) and (iii). These can bind further LFPs. See FIG. 8 for the subsequent steps.

FIG. 5

Figure 5A:
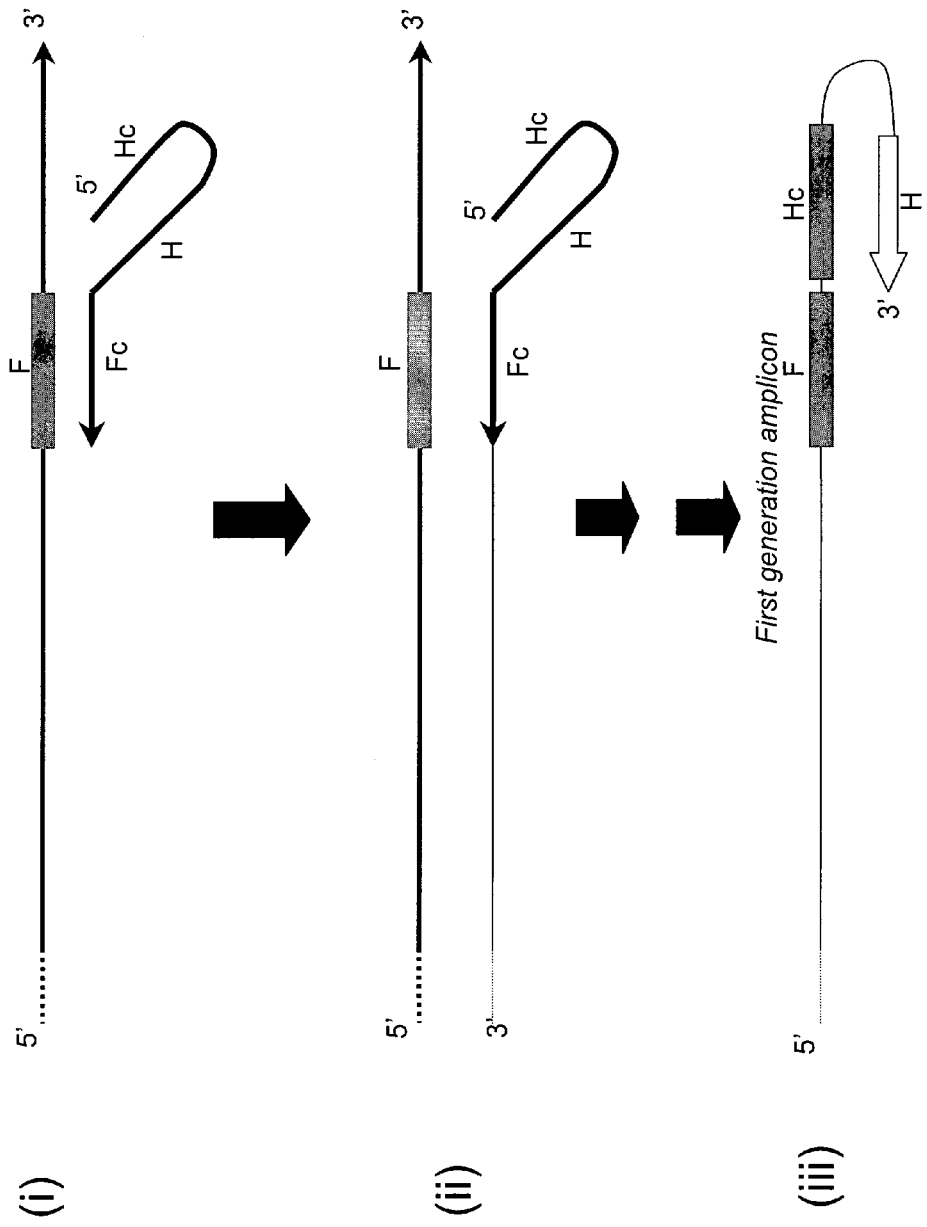
Figure 5B:
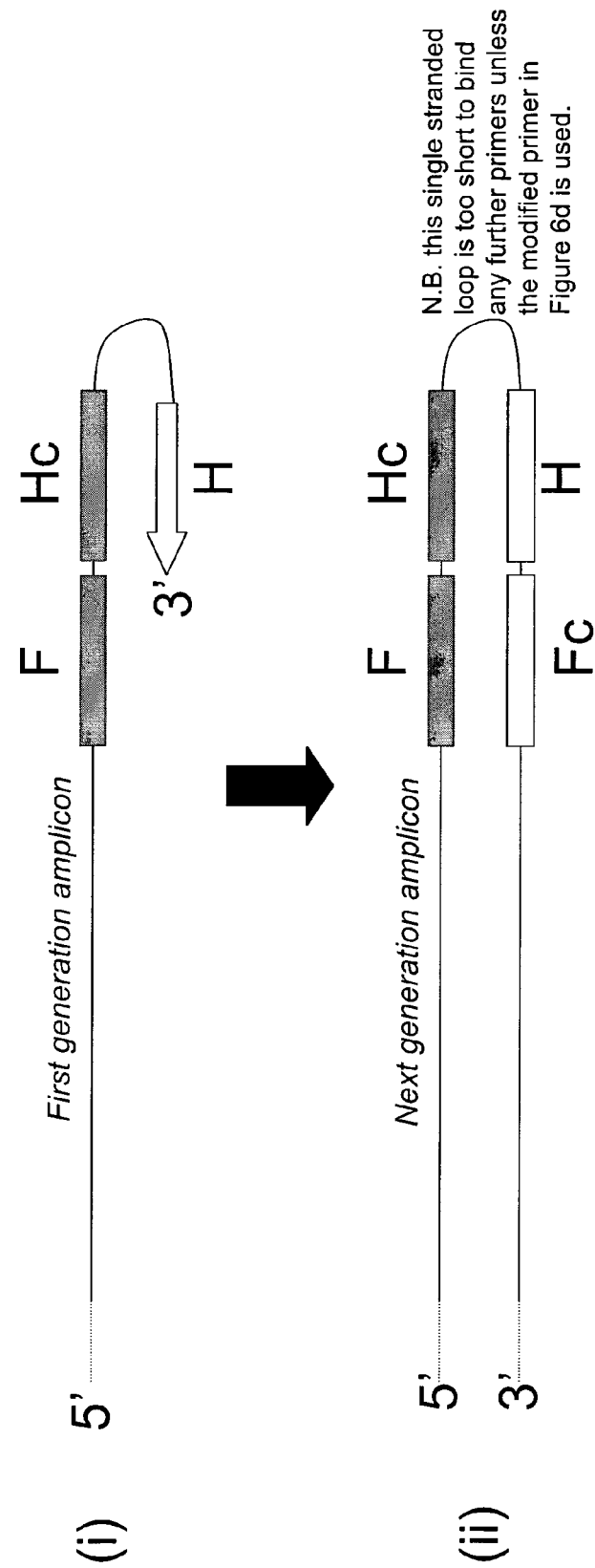
Figure 5C:
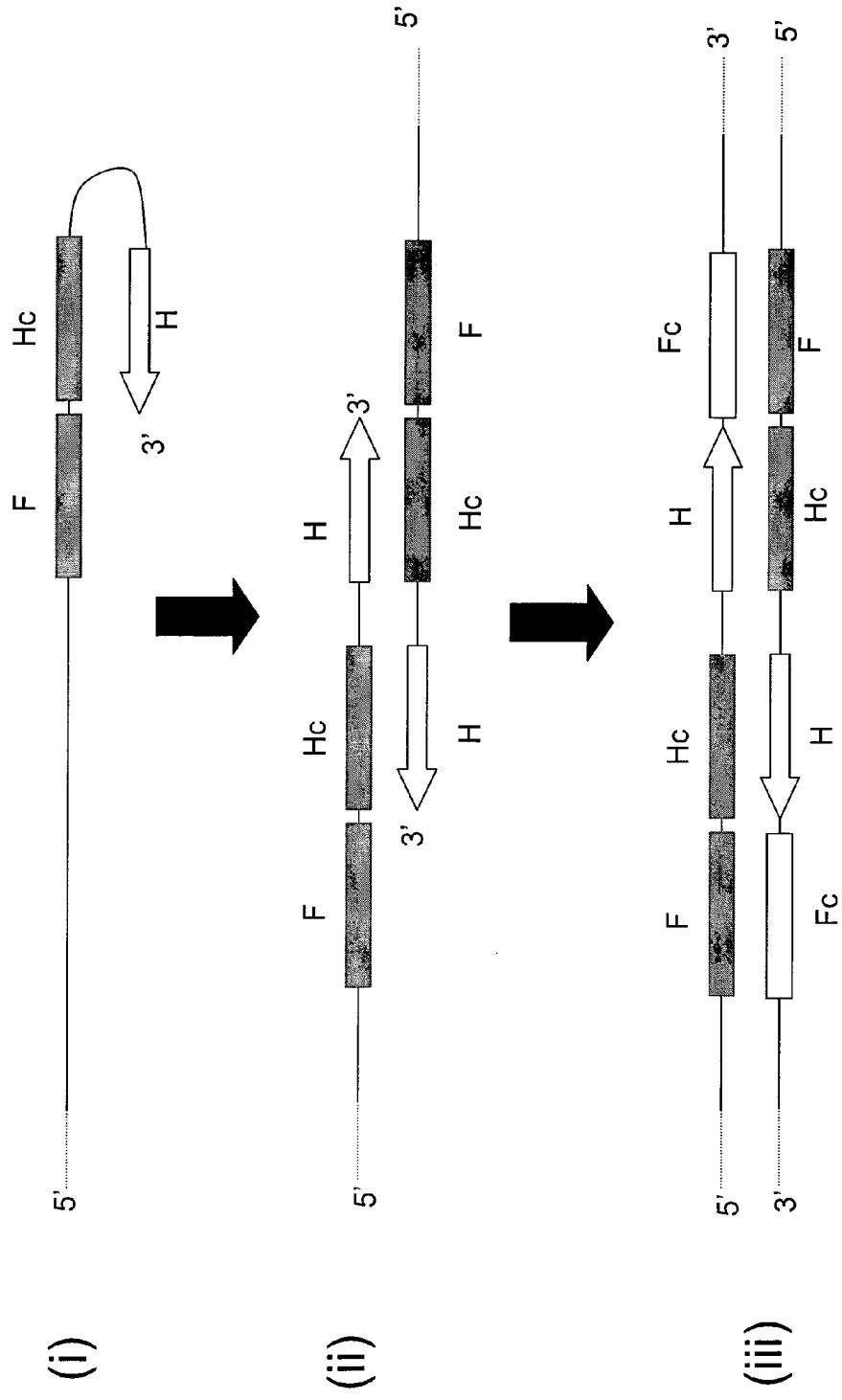

FIG. 5 shows an identical process as for FIG. 4 except that the inverted repeat necessary for concatamer formation is already inherent in the Hairpin Primers and does not require strand extension to form as per LFPs.

FIG. 6

The nature of various primers referred to herein is shown. In FIG. 6a a "Simple Primer" is shown where a substantive majority or all of the primer is involved in Watson-Crick base-pairing with the polynucleotide template. In FIG. 6b it is shown how LFP differ from a simple primer in having an additional 5' region which is substantially identical to a region 3' to the binding site for the 3' end of said primer. A consequence of this is that extension of this primer generates an inverted repeat between the 5' region of the primer and the extension product (See also FIG. 4a(ii)). In FIG. 6c is shown the Hairpin Primers used in SEA. The 5' region of these primers contain an inverted repeat such that the 5' region is expected to fold into a hairpin structure. The hairpin is expected to be a tight hairpin containing very few single-stranded nucleotides and hence this single-stranded region is unlikely to be available to bind another primer. However, if the hairpin is enlarged to form a substantial loop as in FIG. 6d, then binding of a primer to this loop would be possible.

FIG. 7

Showing an agarose gel stained with ethidium bromide where the results of two different amplification technologies are shown run side by side, one is LAMP the other TRA. For LAMP the amplification made use of displacement primers and LFPs (but not Loop Primers) in TRA the amplification made use of the same LFPs as in LAMP but with no other primers present.

It can be readily seen that both LAMP and TRA give concatameric amplicons. Further, the sizes of the amplicons are apparently identical. This suggests that TRA and LAMP share a common mechanism for concatamerisation.

FIG. 8

Figure 8A:
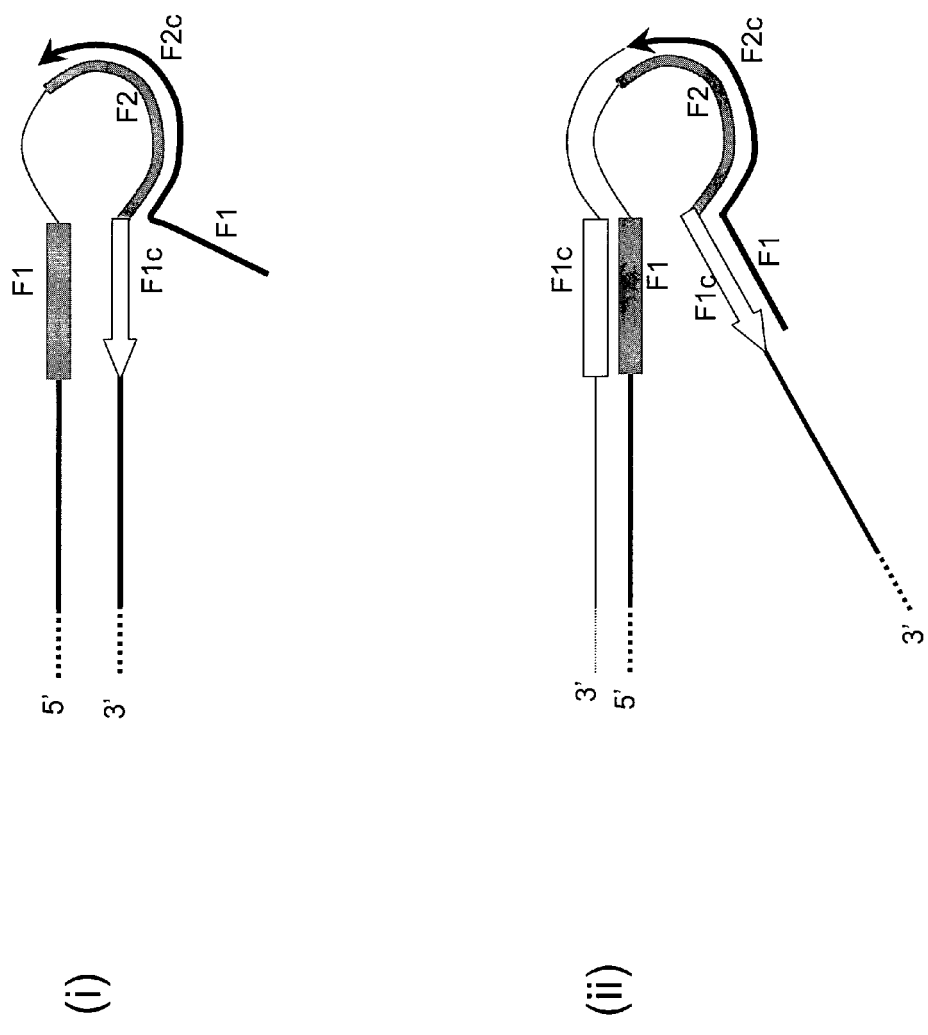
Figure 8B:
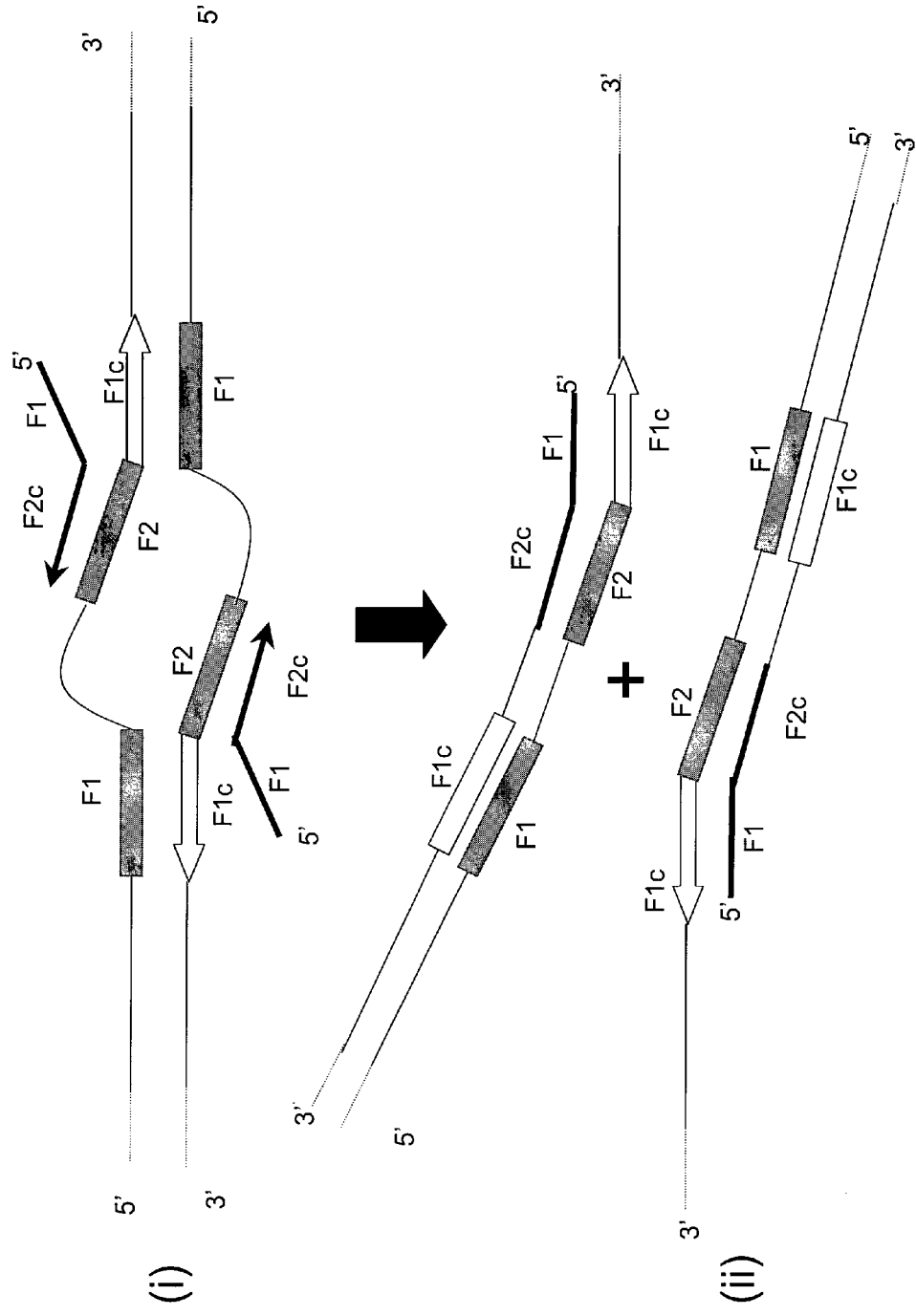
Figure 8C:
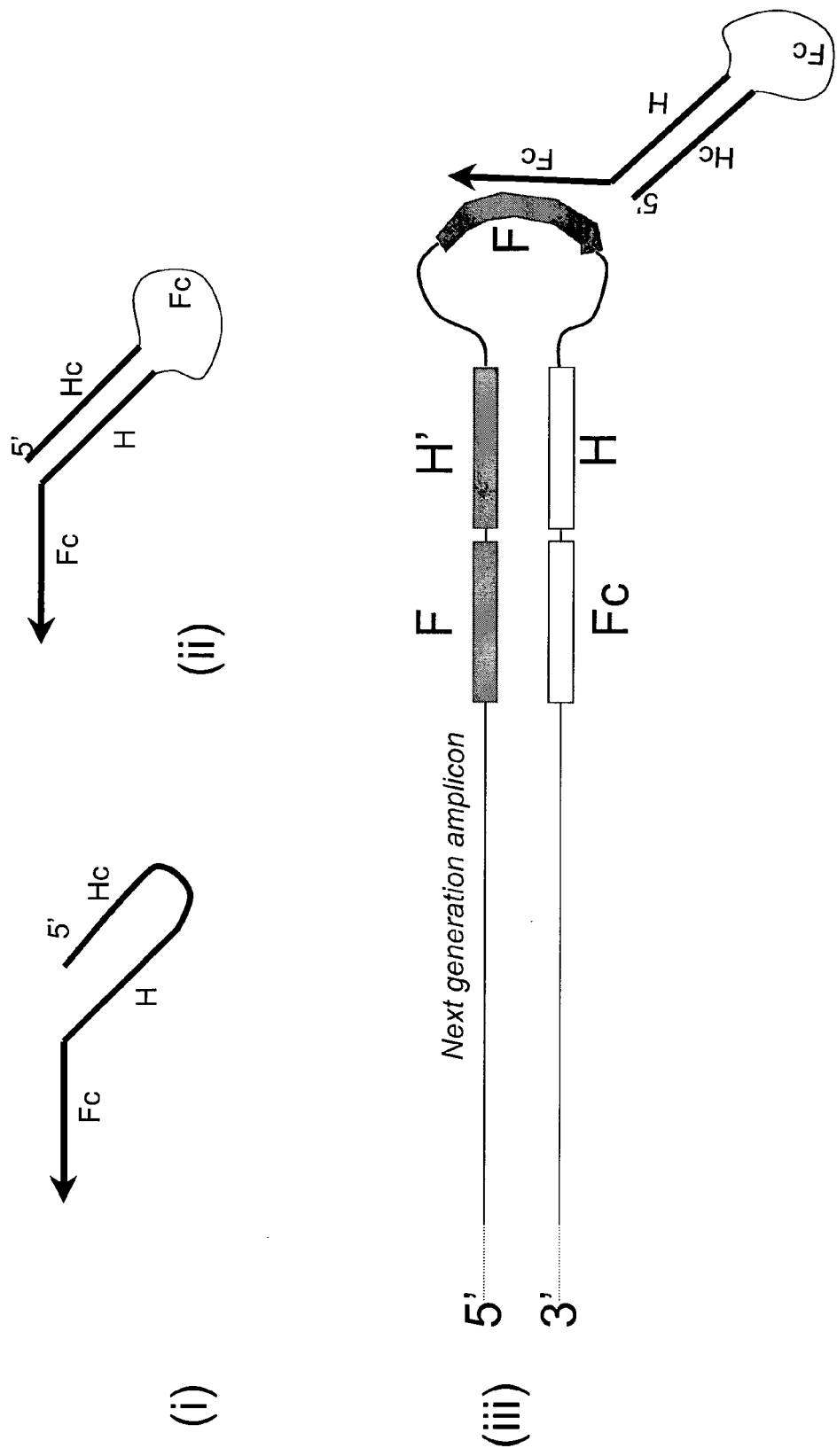

The effect of binding further LFPs to the loops they previously generated is shown in FIG. 8. FIG. 8a shows LFPs binding to loops formed from intra-molecular self-priming of the First Generation Amplicon (or for Next Generation Amplicon), FIG. 8b shows the same for inter-molecular formed loops. In both cases, the extension of the newly bound LFPs causes the opposite strand to become single stranded (FIG. 8a(ii) and FIG. 8b(ii). FIG. 9 will show how stem primers can bind these regions. FIG. 8c emphasises that if a modification of a hairpin primer (FIG. 8c(i)) is made to provide an intrinsic single stranded loop containing the same sequence as the 3' end of the primer (as shown in FIG. 8c(ii)) then the resulting Next Generation Amplicon will provide a single stranded loop for binding a further hairpin primer (FIG. 8c(iii)).

FIG. 9

Figure 9A:
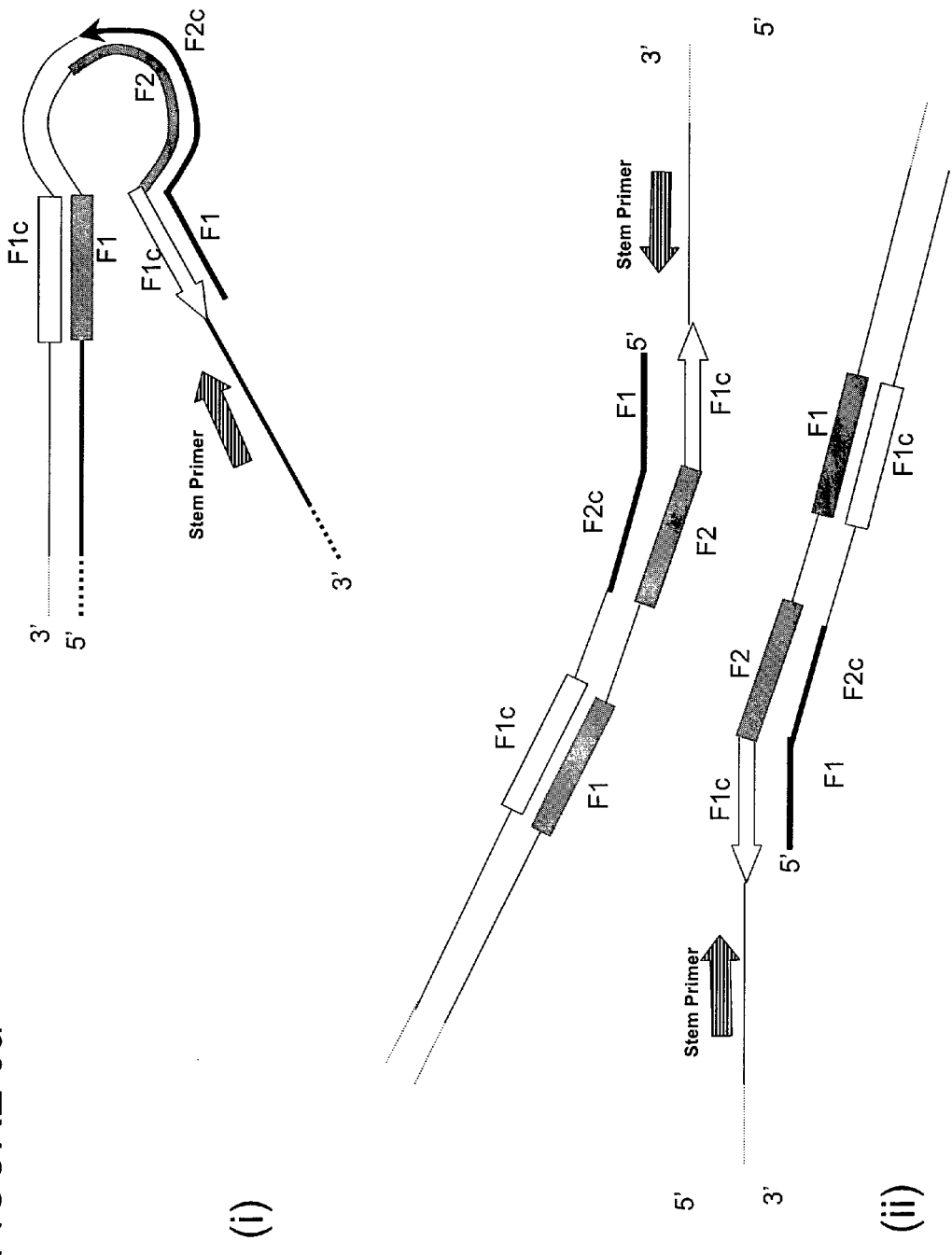
Figure 9B:
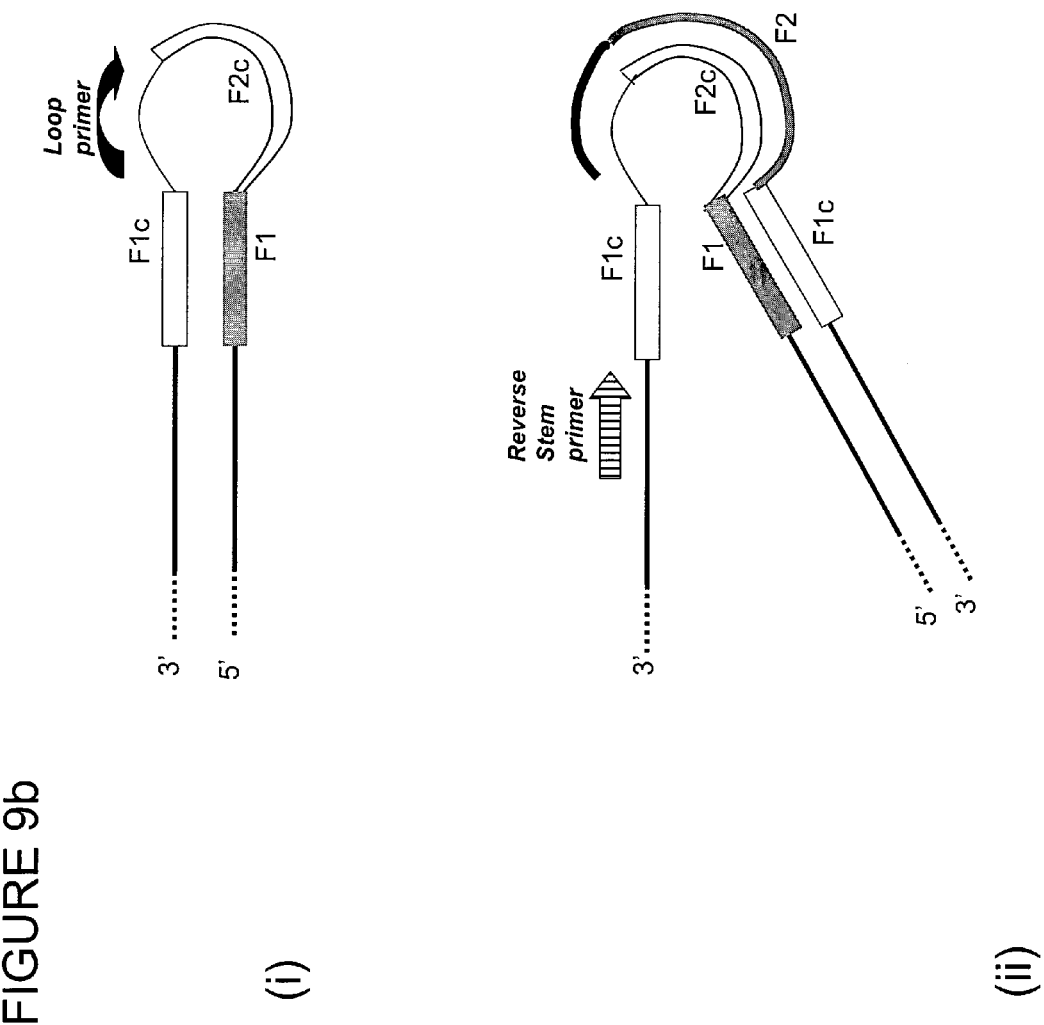
Figure 10:
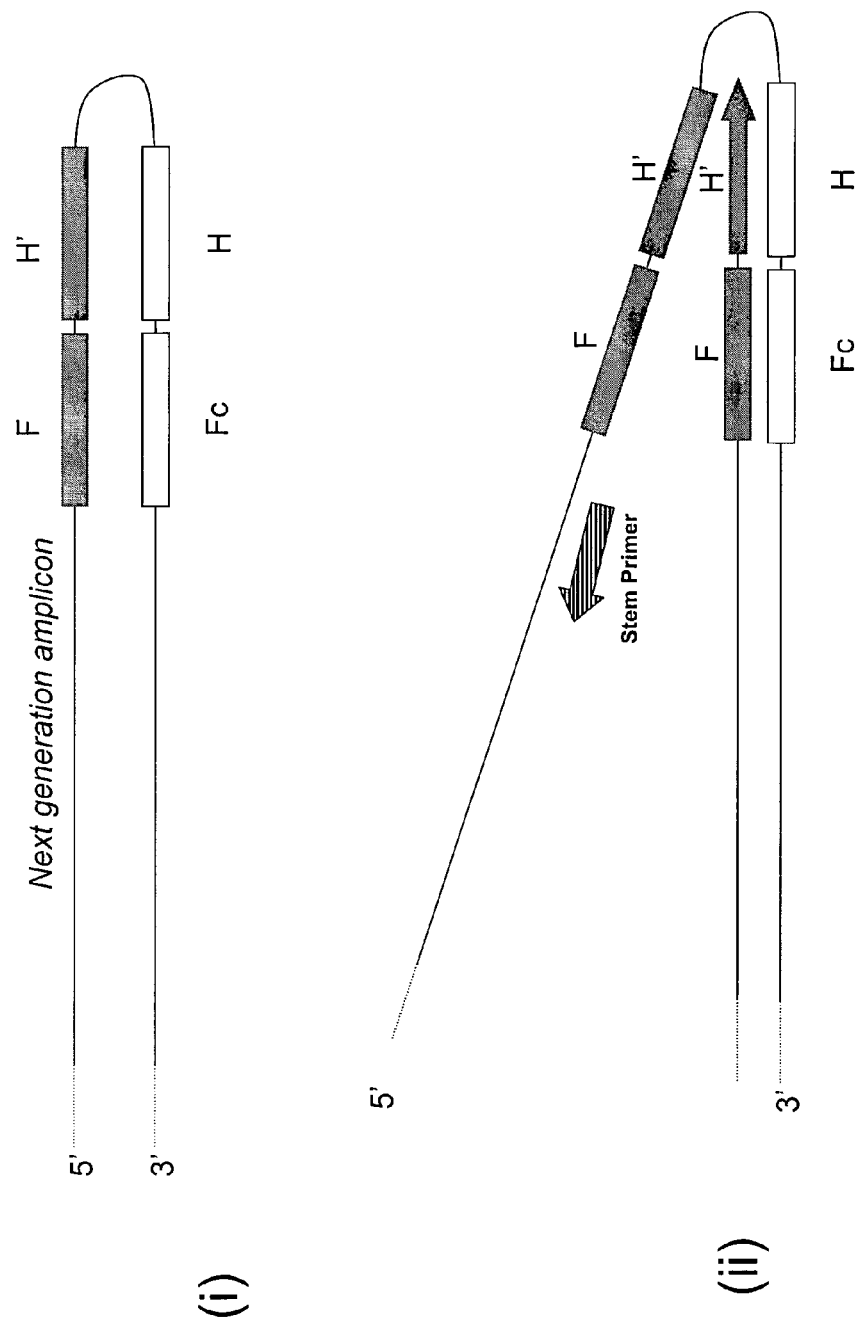

For either intra (FIG. 9a(i)) or inter (FIG. 9a(ii)) molecular Next Generation Amplicon formation, a region of amplicon stem is exposed as single stranded and available for stem primer binding. This is also the case for the reciprocal loop which is formed by LFP (i.e. the reciprocal strand of the loop shown in FIG. 8a which is also generated), this Loop cannot bind a LFP since it is the same sense as the LFPs, but can bind one of the so called 'loop primers' (FIG. 9b(i)) where employed. The extension of the loop primer also makes a region of the amplicon stem single stranded and hence available for binding a stem primer (FIG. 9b(ii)).

FIG. 10

Shows how for SEA, the recopying of Next Generation Amplicon via self-extension of Amplicon, also makes a region of the amplicon stem available for binding by a stem primer.

FIG. 11

Figure 11:
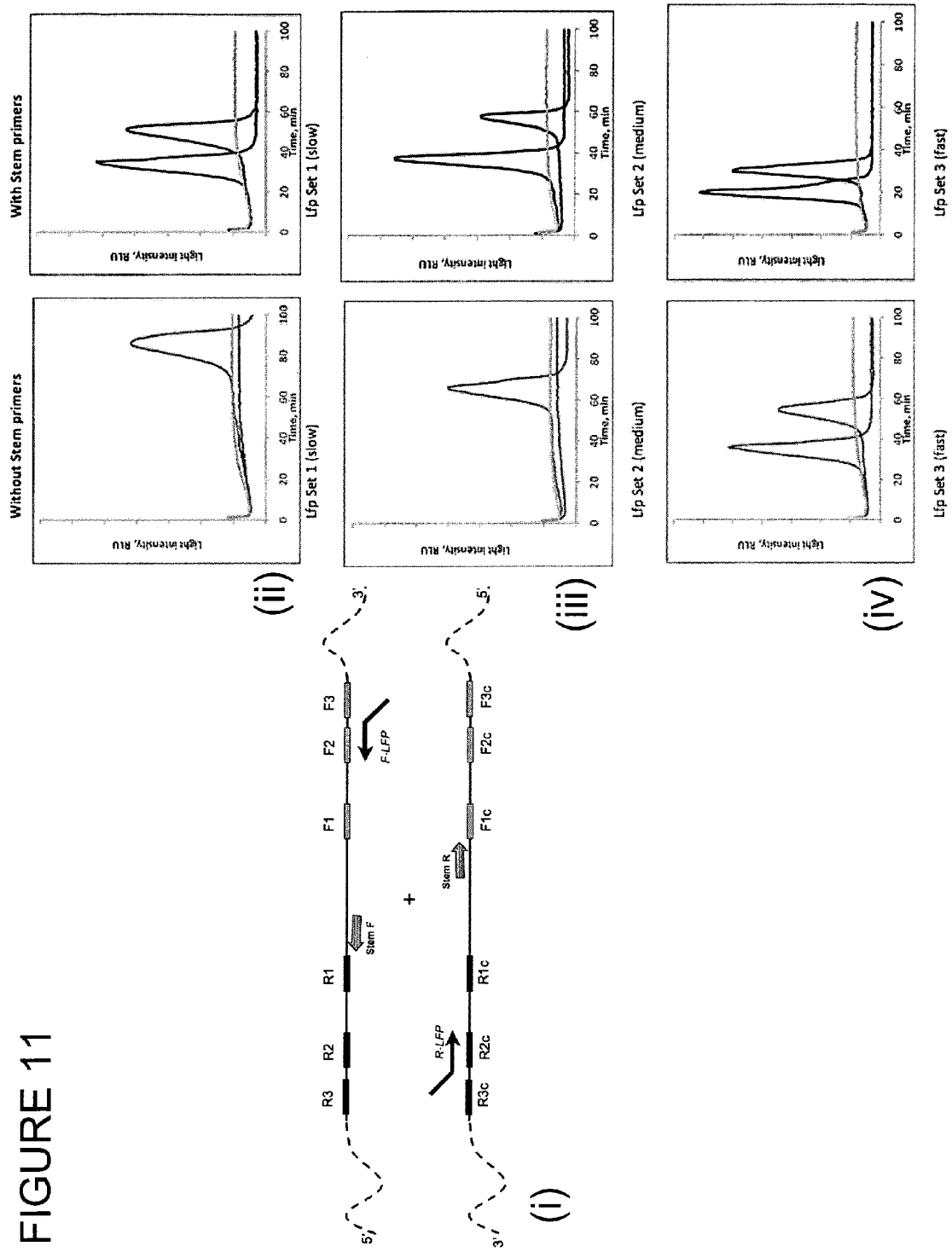

Showing the rate increase using stem primers in TRA followed by BART for three different sets of primers in *Listeria monocytogenes* system. Schematic location of LFP and Stem primers is given in FIG. 11(i). FIGS. 11(ii)-11(iv) show BART comparison of rates in the absence of Stem primers (left-hand panels) with those in the presence of Stem primers (right-hand panels) for slow, medium and fast sets of LFPs, correspondingly. On each graph the earlier peak represents higher copy number ($10^8$) and the later peak, if observed at all, represents $10^4$ copies of the target. No-template controls are shown in light grey.

FIG. 12

Figure 12A:
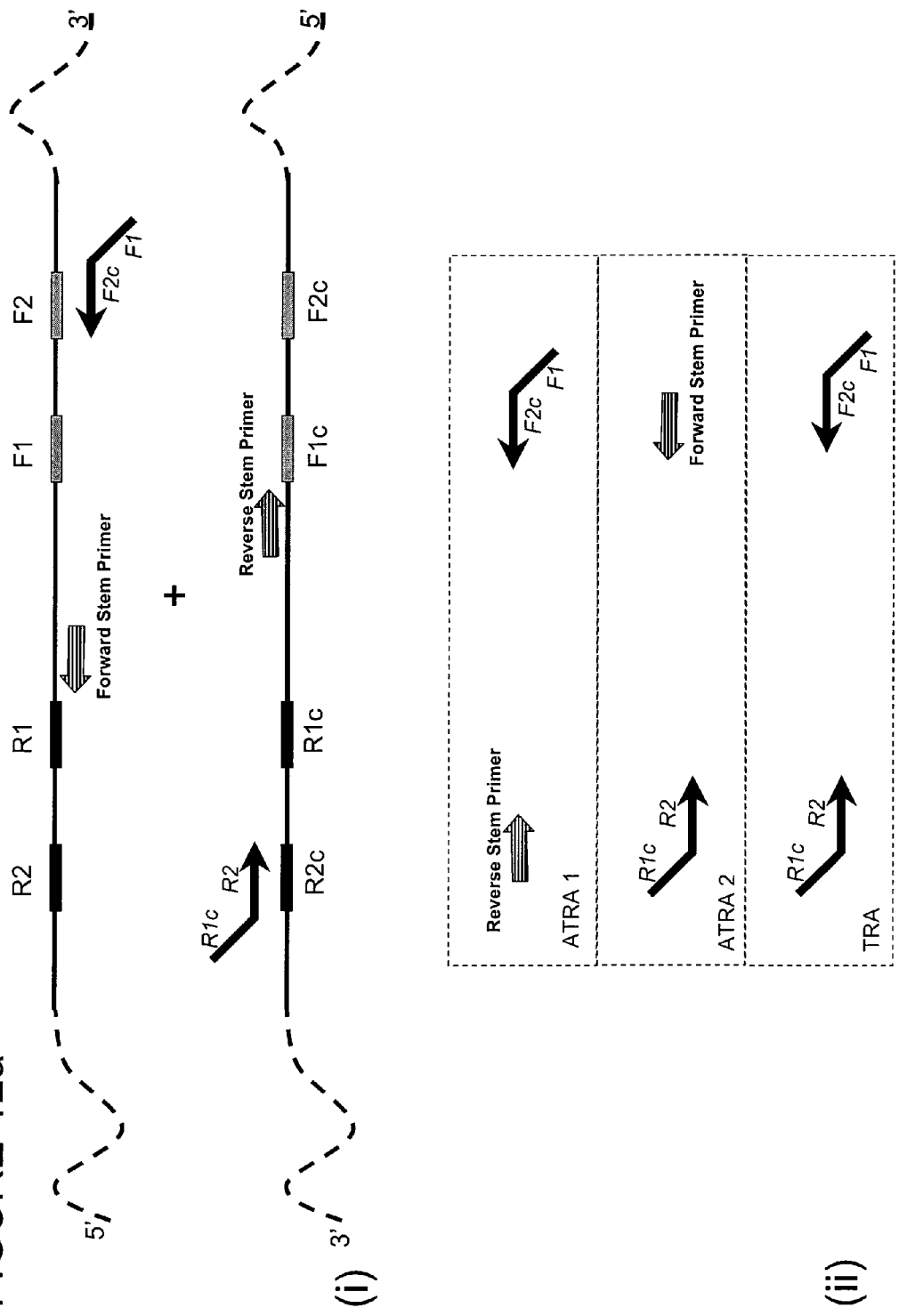
Figure 12B:
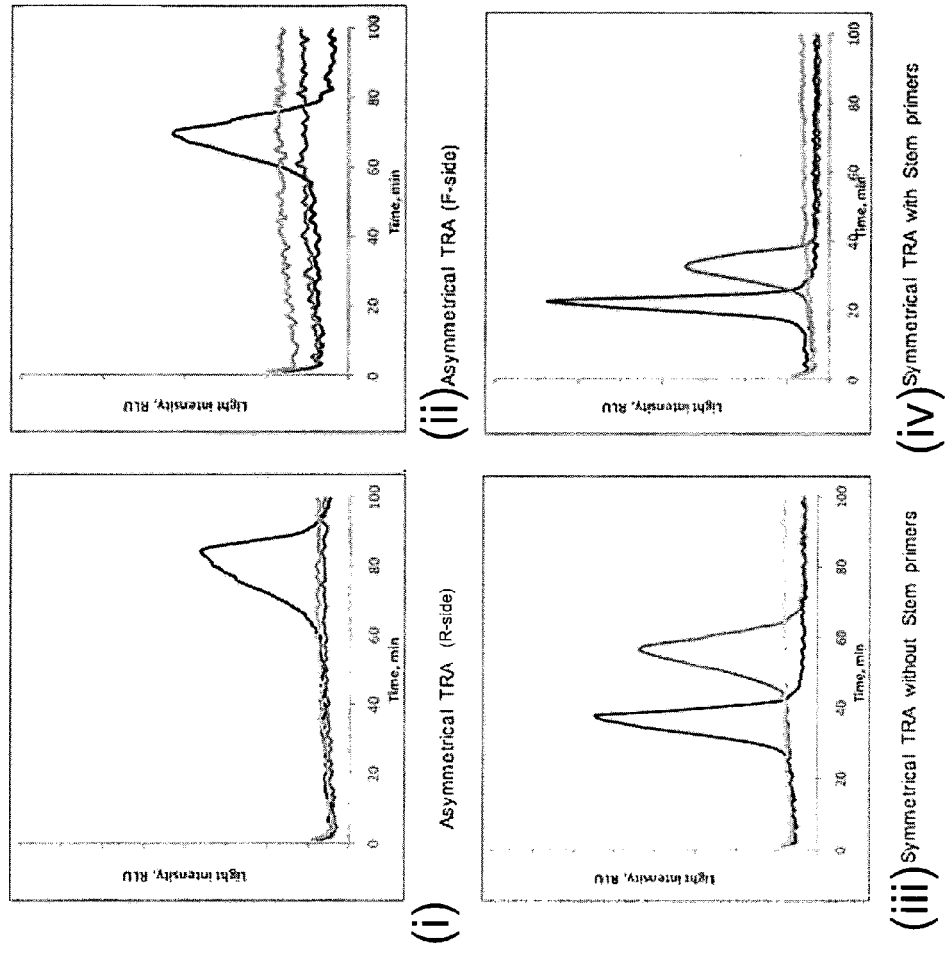

Highlights how the use of Stem primers in TRA in *Listeria monocytogenes* system (FIG. 12a(i)) could be deconstructed into three independent amplification processes, one of which is TRA and the other two are ATRA (FIG. 12a(ii)). BART comparison of rates for both ATRA, TRA and a full combination of primers are shown in FIG. 12b(i)-(iv) correspondingly. On each graph the earlier peak represents higher copy number ($10^8$) and the later peak, if observed at all, represents $10^4$ copies of the target. No-template controls are shown in light grey.

FIG. 13

Figure 13:
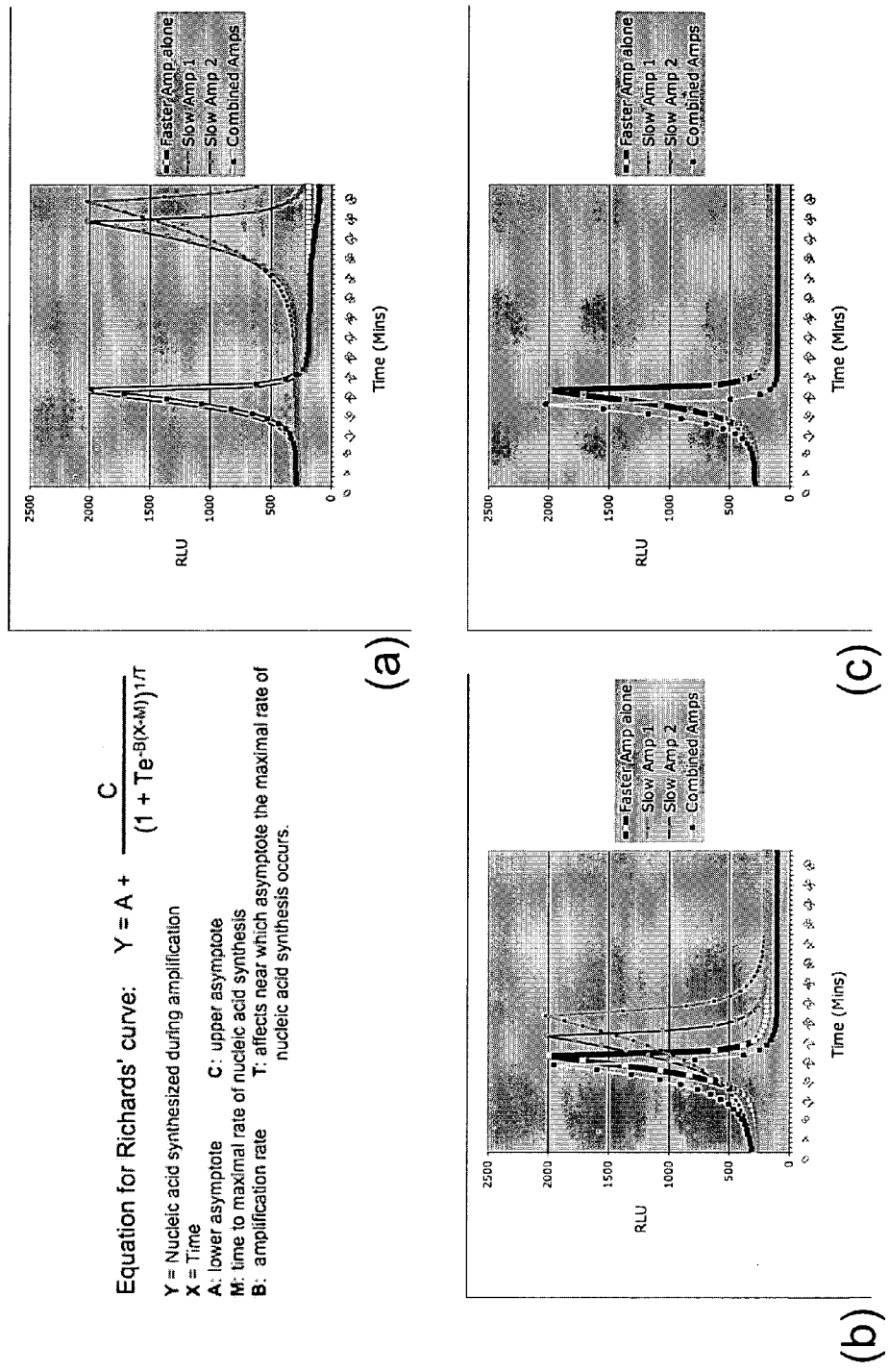

Showing kinetic models of BART where three different amplification reactions are combined. In FIG. 13a, a fast NAAT is combined with two very slow NAATs, it can be seen that the overall rate of amplification (i.e. the sum of the three amplification reactions rates) gives a BART peak identical in timing to the fastest of the three NAATs; FIG. 13b as for 13a except a fast NAAT is combined with two slightly faster NAATs, in this case the overall rate of amplification is only very slightly effected and the BART peak occurs only a few minutes earlier; FIG. 13c as for 13a and b except the so-called slower NAATs are now as fast as the fastest NAAT: the combined overall rate of amplification is still only very slightly effected and the BART peak occurs only a few minutes earlier. FIG. 13 reflects that where a number of different exponential processes occur simultaneously, a significantly earlier BART peak, as seen with the employment of stem primers, is not observed. This underlines that stem primers act to fundamentally and significantly increase the intrinsic rate of amplification when employed with a particular NAAT rather than to add separate slower or similar speed processes.

FIG. 14

For each part (a) to (g) of FIG. 14, part (i) of each figure shows for double-stranded template, the position of the primer binding sites for the primers employed by a variety of NAATs. Primers associated with the forward reciprocal binding region are denoted with an F and those with the reverse reciprocal binding region are denoted with an R. Part (ii) of each figure shows where the various primers employed by a particular NAAT bind on the respective strands; a potential location for the stem primer binding is also shown but the exact position of the stem primer and the number of stem primers employed can be significantly varied as detailed in FIG. 2.

Figure 14A:
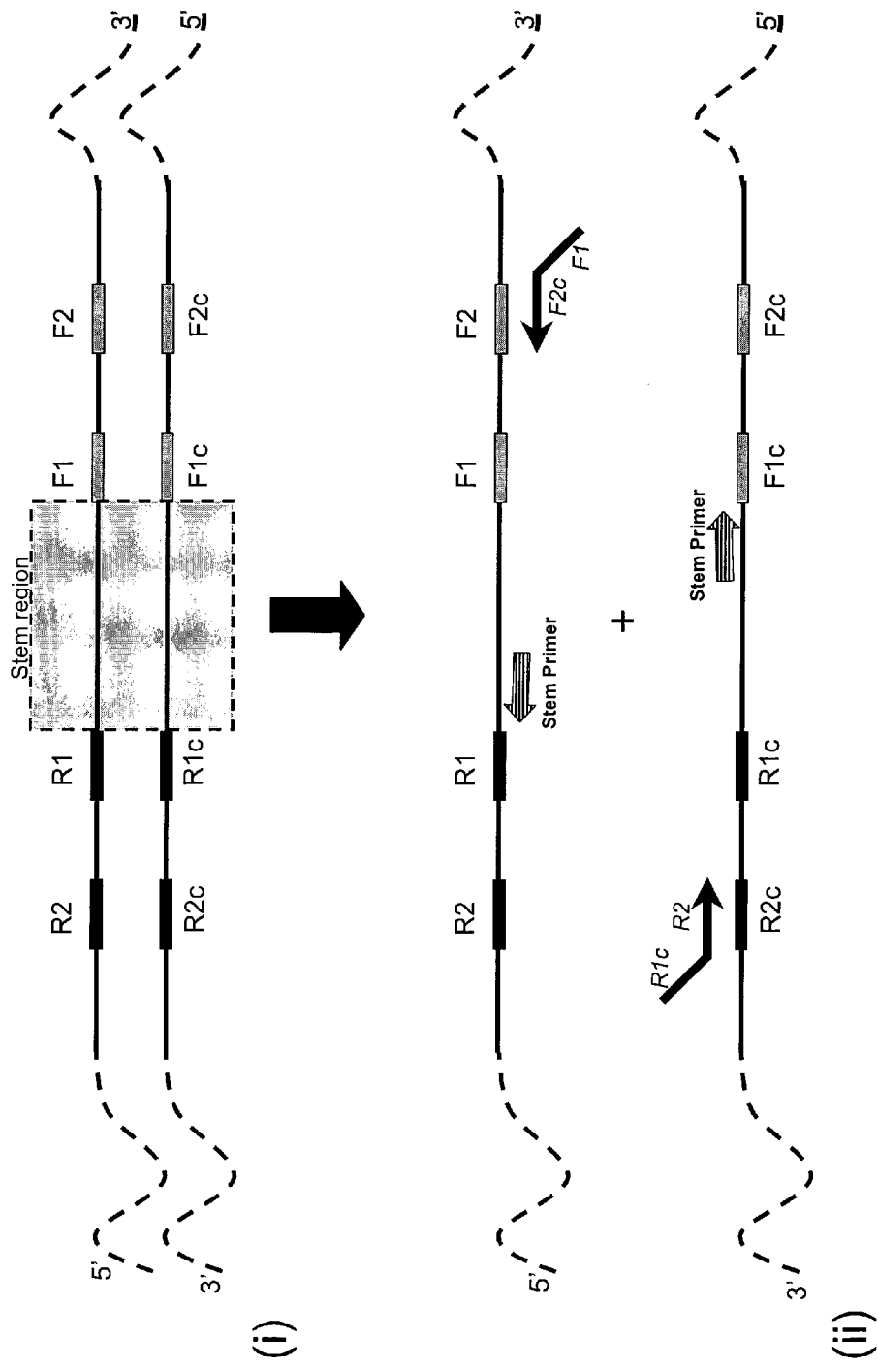
Figure 14B:
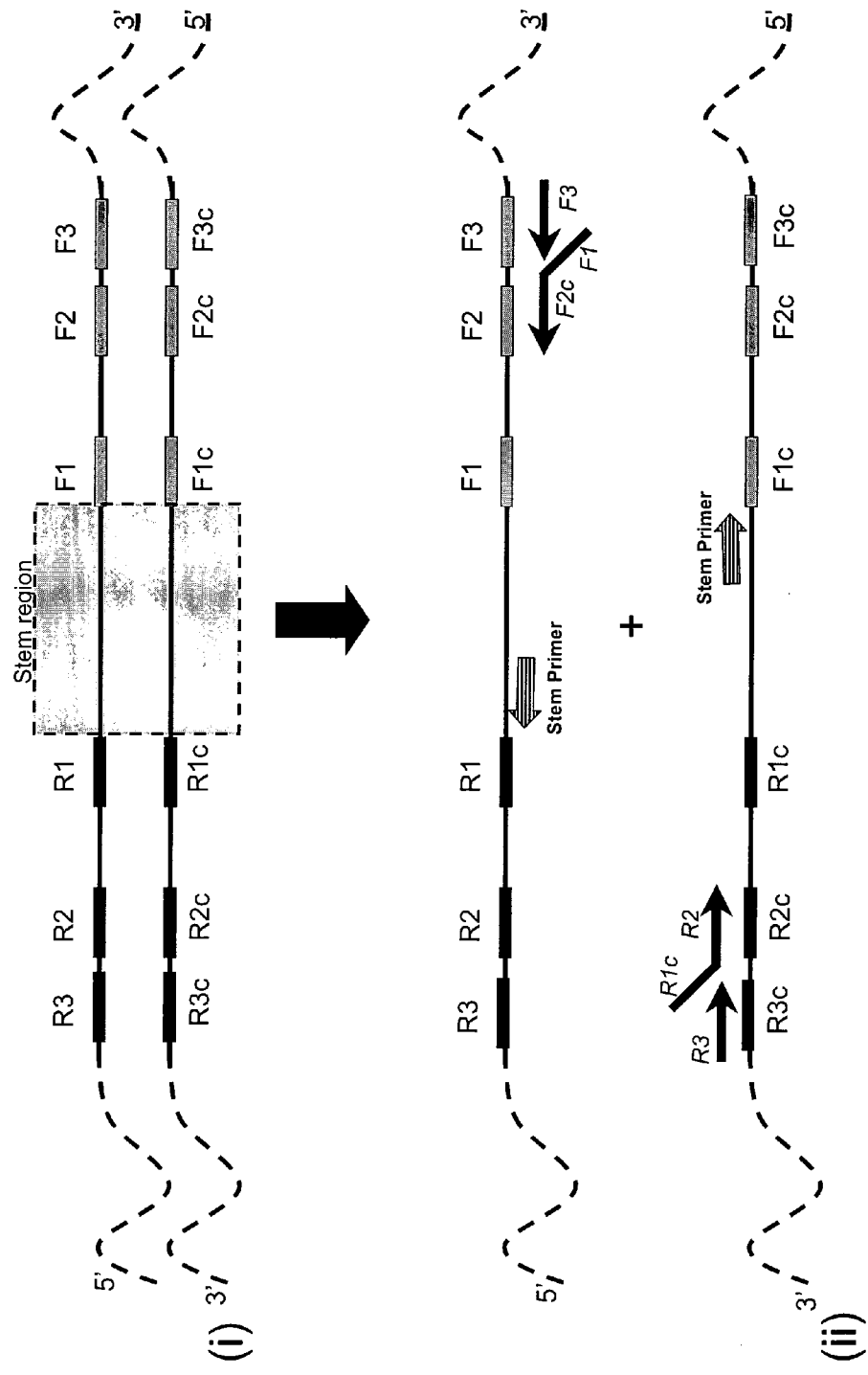
Figure 14C:
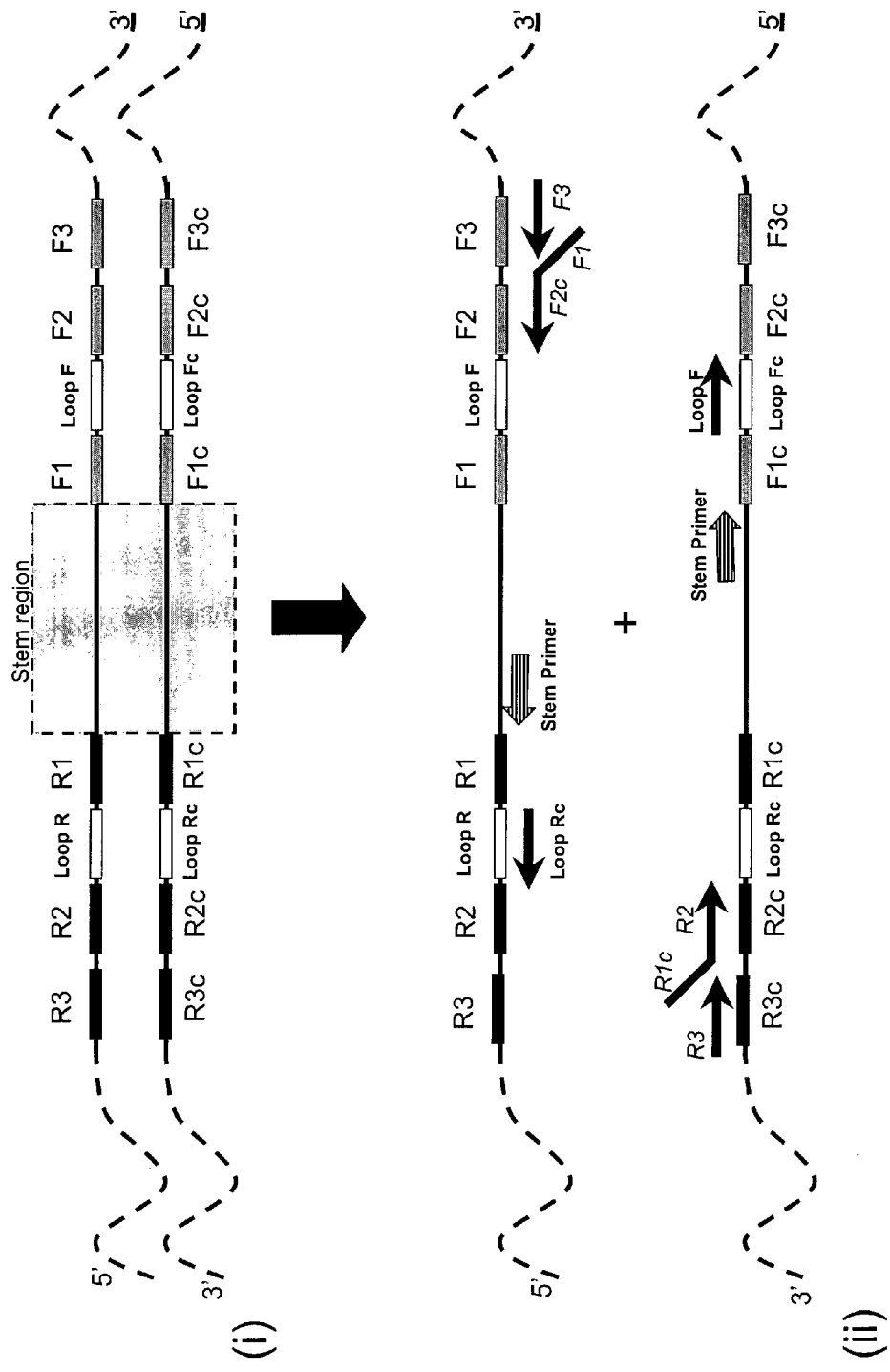
Figure 14D:
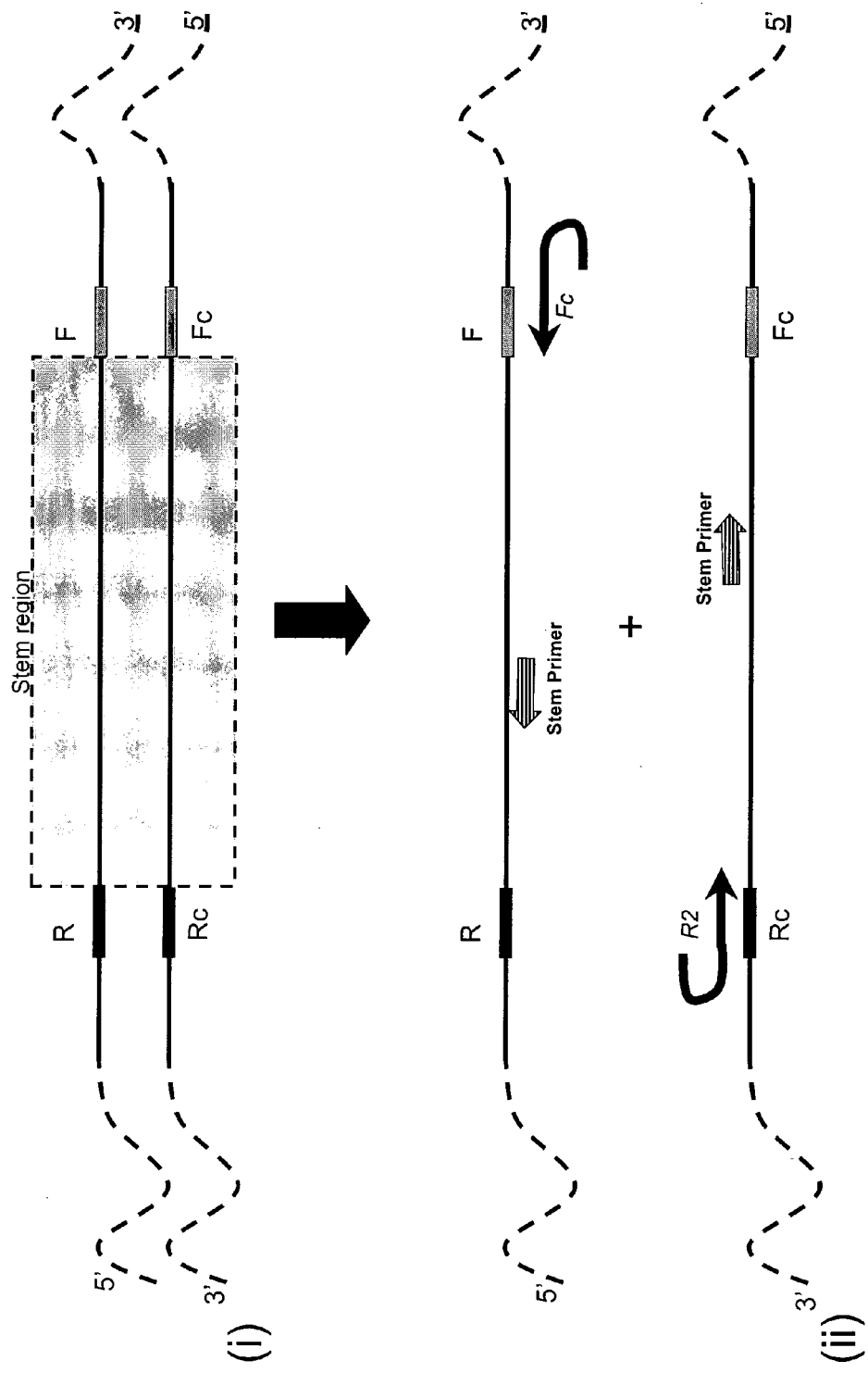
Figure 14E:
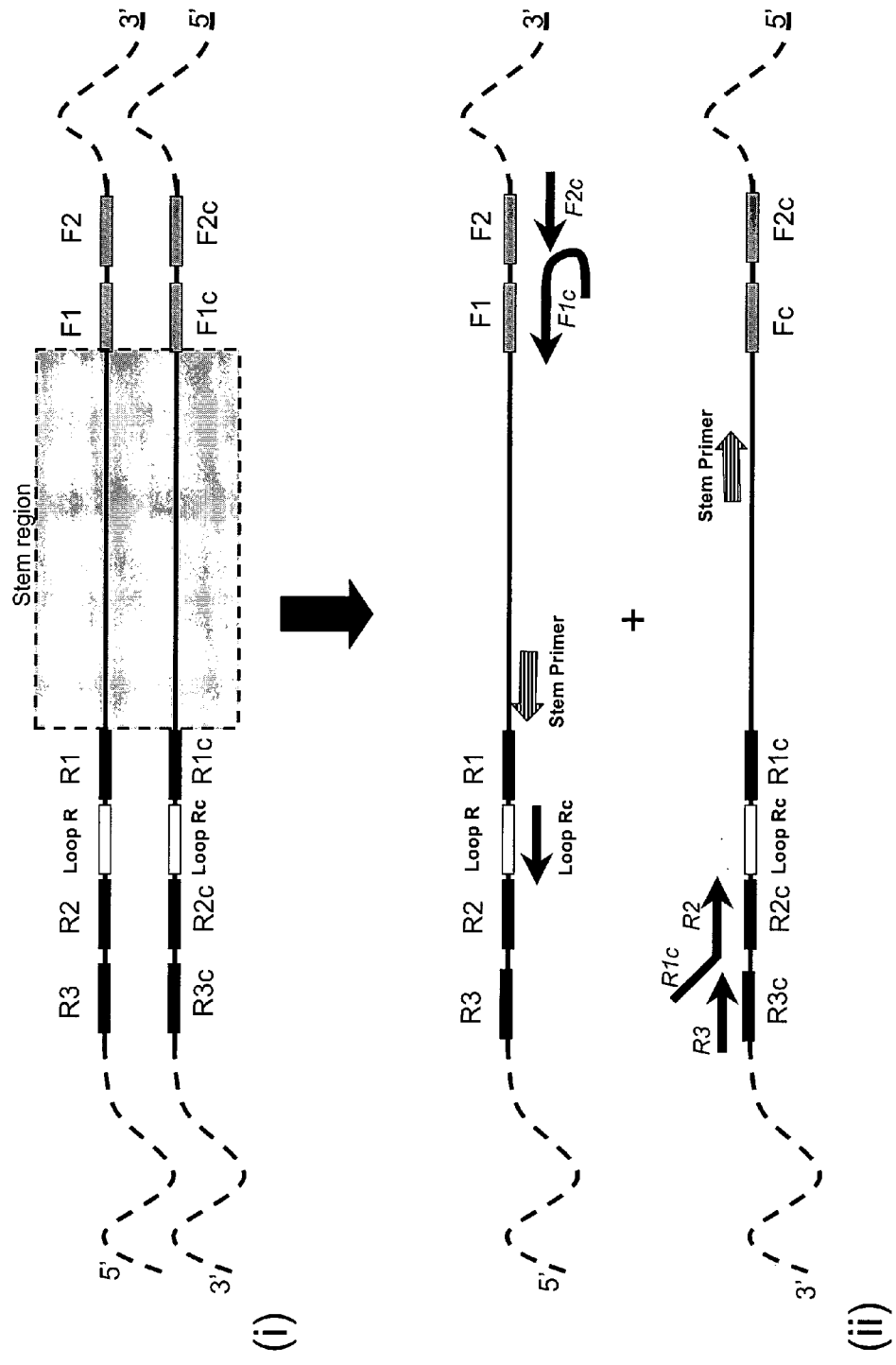
Figure 14F:
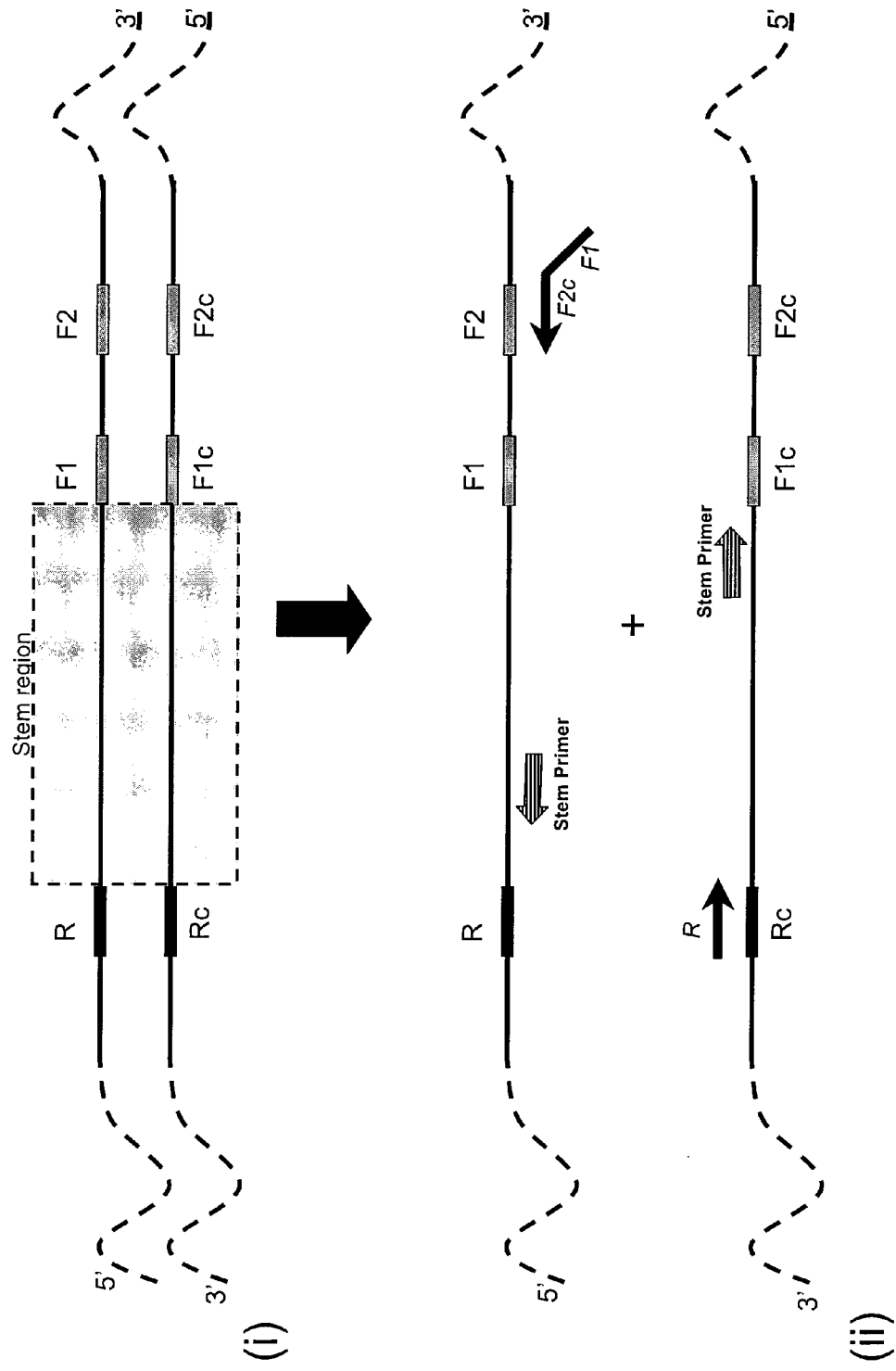
Figure 14G:
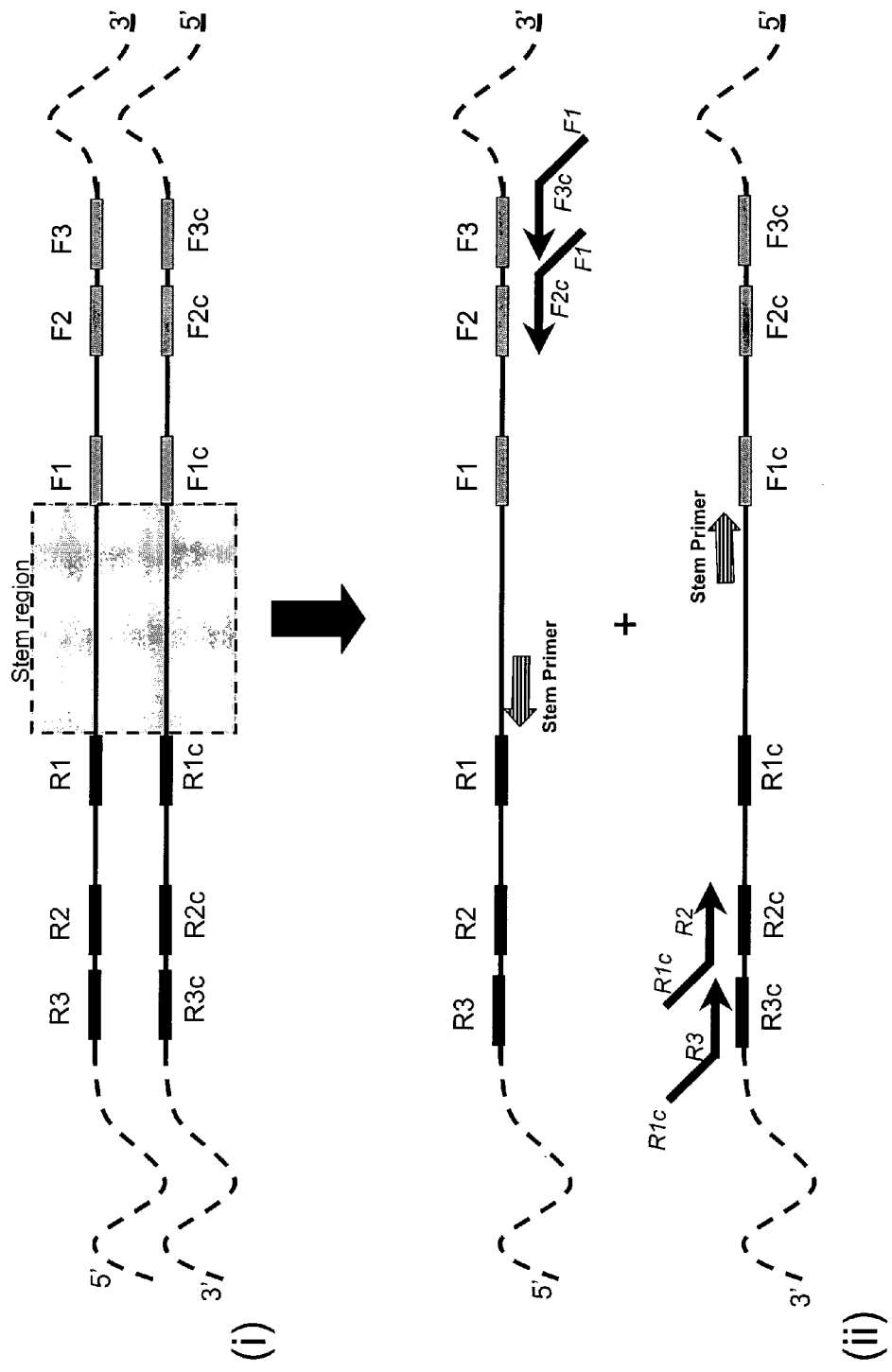

FIG. 14a shows stem primers acting in TRA; FIG. 14b shows stem primers acting in LAMP; FIG. 14c shows stem primers acting in an improved manifestation of LAMP which also uses loop primers; FIG. 14d shows stem primers acting in SEA; FIG. 14e shows stem primers acting in SMAP, FIG. 14f shows stem primers acting in ATRA & FIG. 14g shows stem primers acting in a version of TRA with nested LFPs.

FIG. 15

Showing the effect of nesting LFPs in the presence and absence of Stem primers in TRA in *Salmonella enteritidis* system.

Figure 15A:
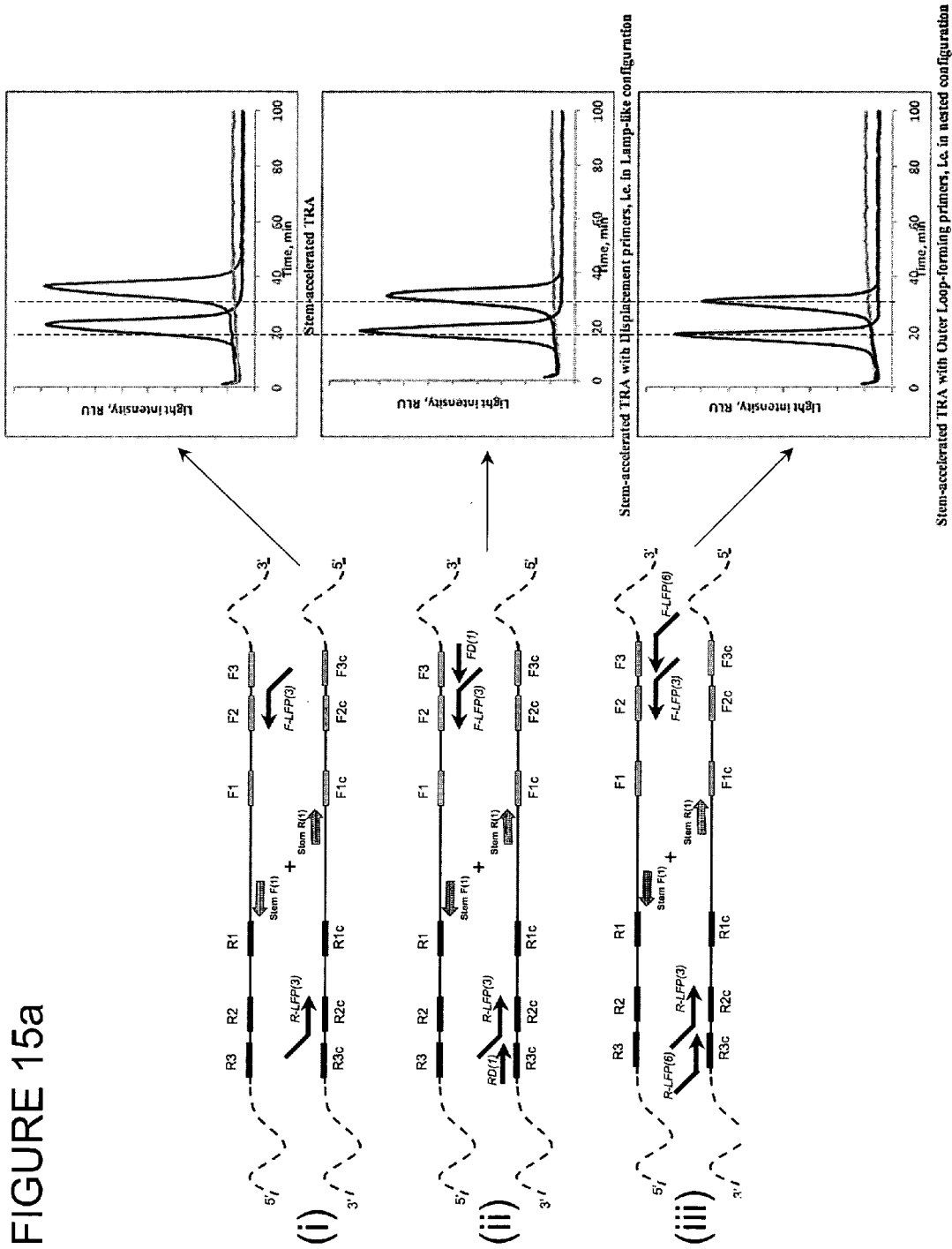

FIG. 15a gives a comparison of Stem-accelerated TRA (FIG. 15a(i)) with Stem-accelerated LAMP (FIG. 15a(ii)) and Stem-accelerated nested TRA (FIG. 15a(iii)). On each graph the earlier peak represents higher copy number ($10^8$) and the later peak, if observed at all, represents $10^4$ copies of the target. No-template controls are shown in light grey.

Figure 15B:
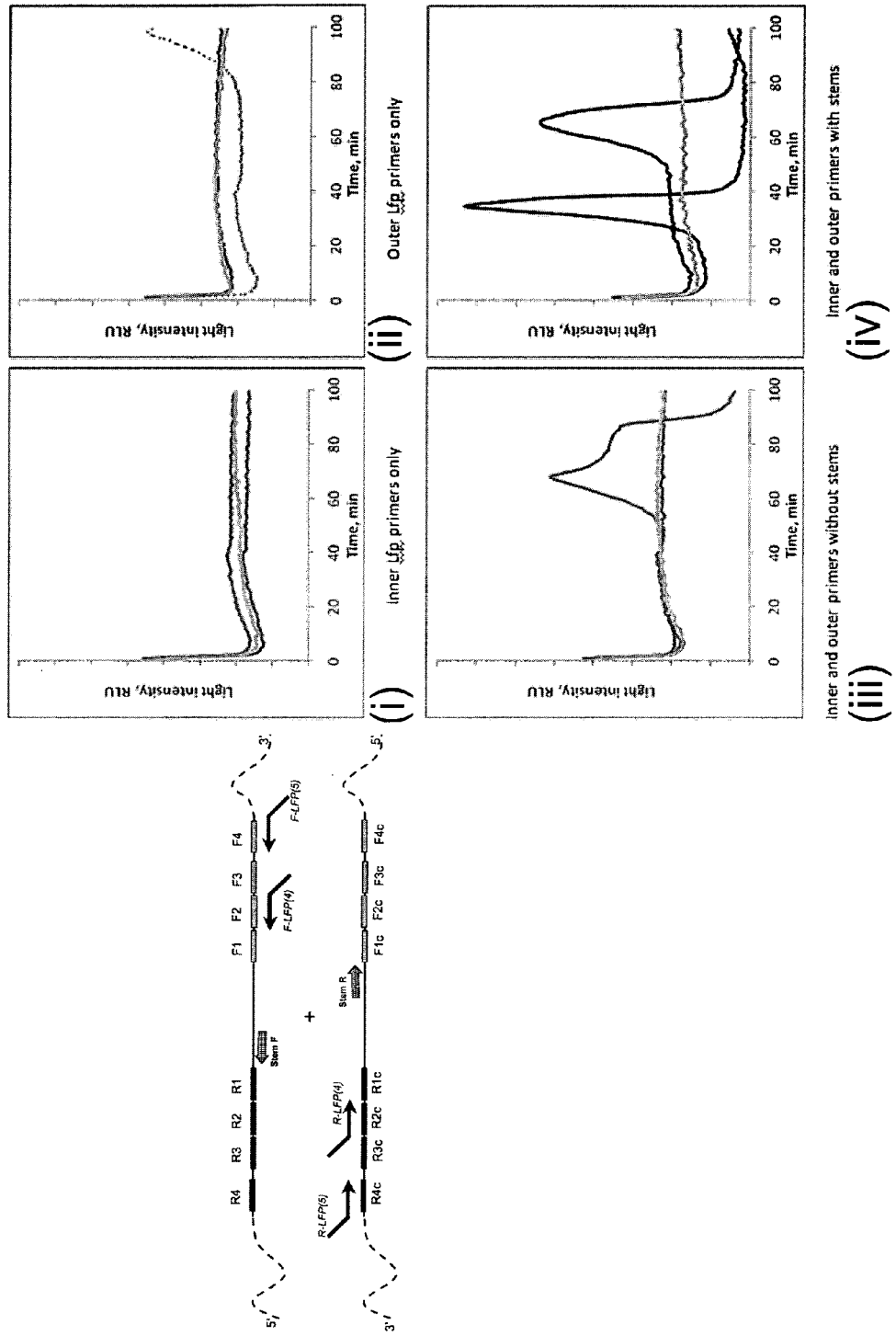

FIG. 15b(i-iv) gives a comparison of BART rates for TRA with inner LFPs, outer LFPs, both inner and outer LFPs in the absence of Stem primers and in the presence of Stem primers, correspondingly. On each graph the earlier peak represents higher copy number ($10^8$) and the later peak, if observed at all, represents $10^4$ copies of the target. No-template controls are shown in light grey.

FIG. 16

Figure 16:
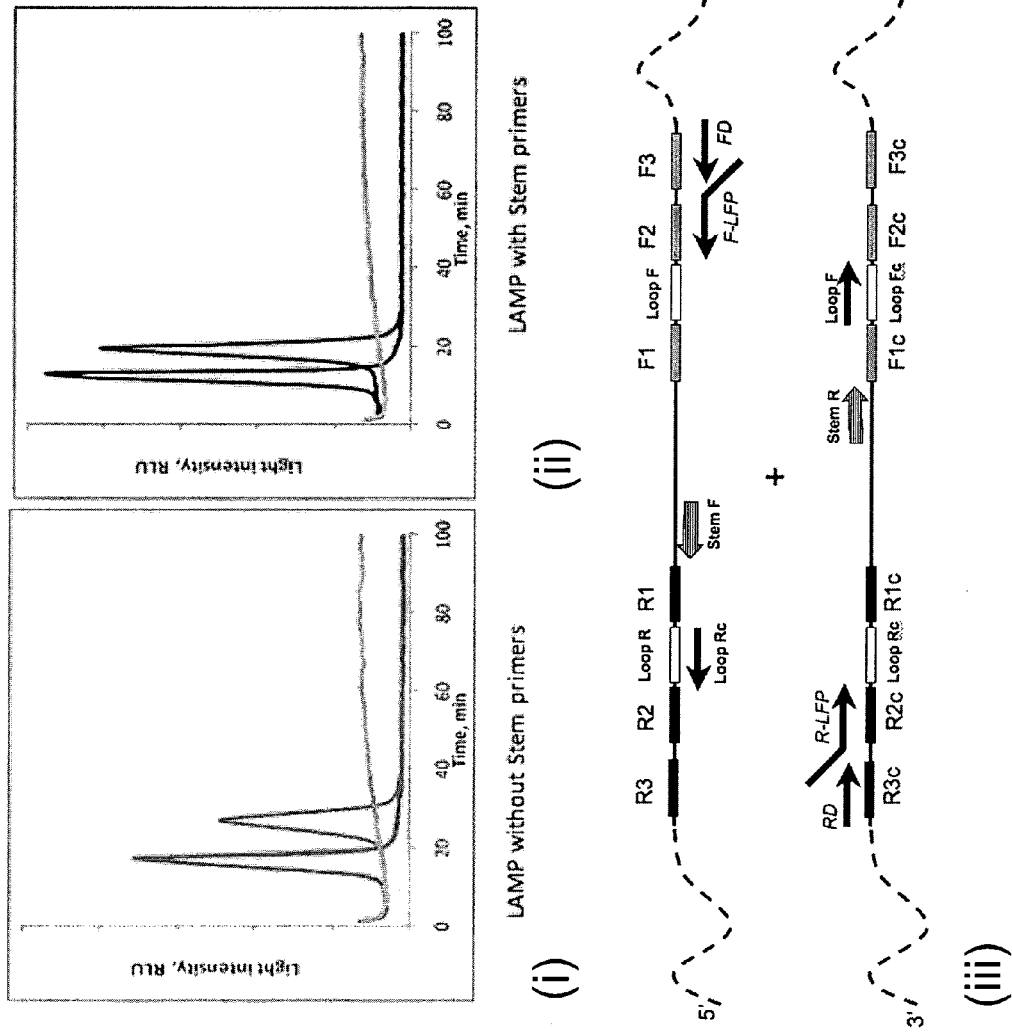

Showing the rate increase using stem primers in LAMP followed by BART in *Listeria monocytogenes* system. Schematic location of all primers is given in FIG. 16(iii) and BART comparison of rates in the absence and in the presence of Stem primers is shown in FIG. 16(i) and FIG. 16(ii), correspondingly. On each graph the earlier peak represents higher copy number ($10^8$) and the later peak represents $10^4$ copies of the target. No-template controls are shown in light grey.

FIG. 17

Figure 17:
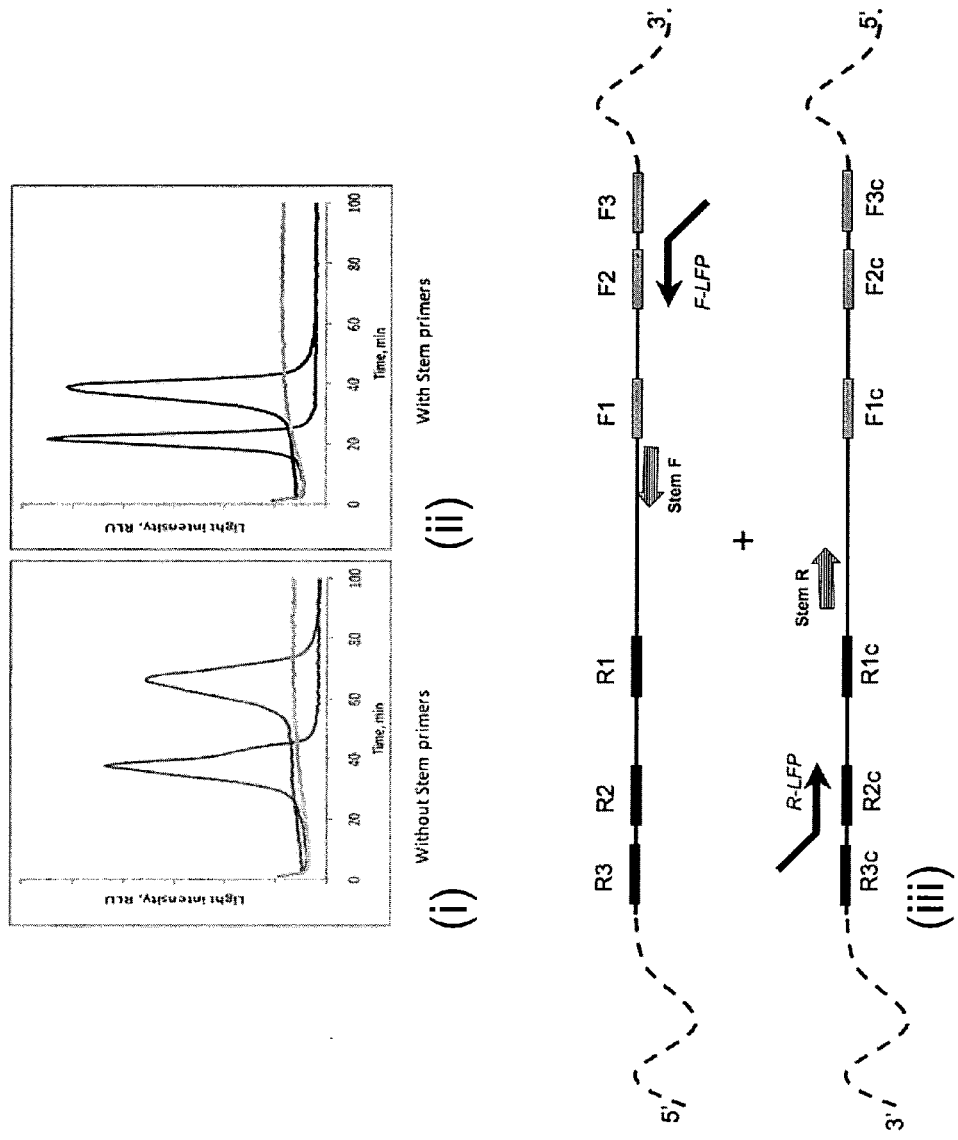

Showing the rate increase using stem primers in TRA followed by BART in *Listeria monocytogenes* system where the stem primers are located in different regions of the stem as compared with the aforementioned examples. Schematic location of all primers is given in FIG. 17(iii) and BART comparison of rates in the absence and in the presence of Stem primers is shown in FIG. 17(i) and FIG. 17(ii), correspondingly. On each graph the earlier peak represents higher copy number ($10^8$) and the later peak represents $10^4$ copies of the target. No-template controls are shown in light grey.

FIG. 18

Showing the greater degrees of freedom for positioning a Stem primer as compared to a Loop primer in LAMP for example. Loop primers are strictly speaking limited to being between either the F1 and F2 sites or the R1 and R2 sites. If the sequence does not allow you to position one or both Loop primers efficiently because the loop is either not long enough or the Loop primer is likely to cause non-specific amplification through primer-dimers you are left with almost no choice for an alternative Loop primer design. Stem primers can be located anywhere on the stem and they can have either orientation allowing you a wide choice of possible designs and optimisation for the highest efficiency while avoiding any non-specific primer-dimerisation.

FIG. 19

Figure 19:
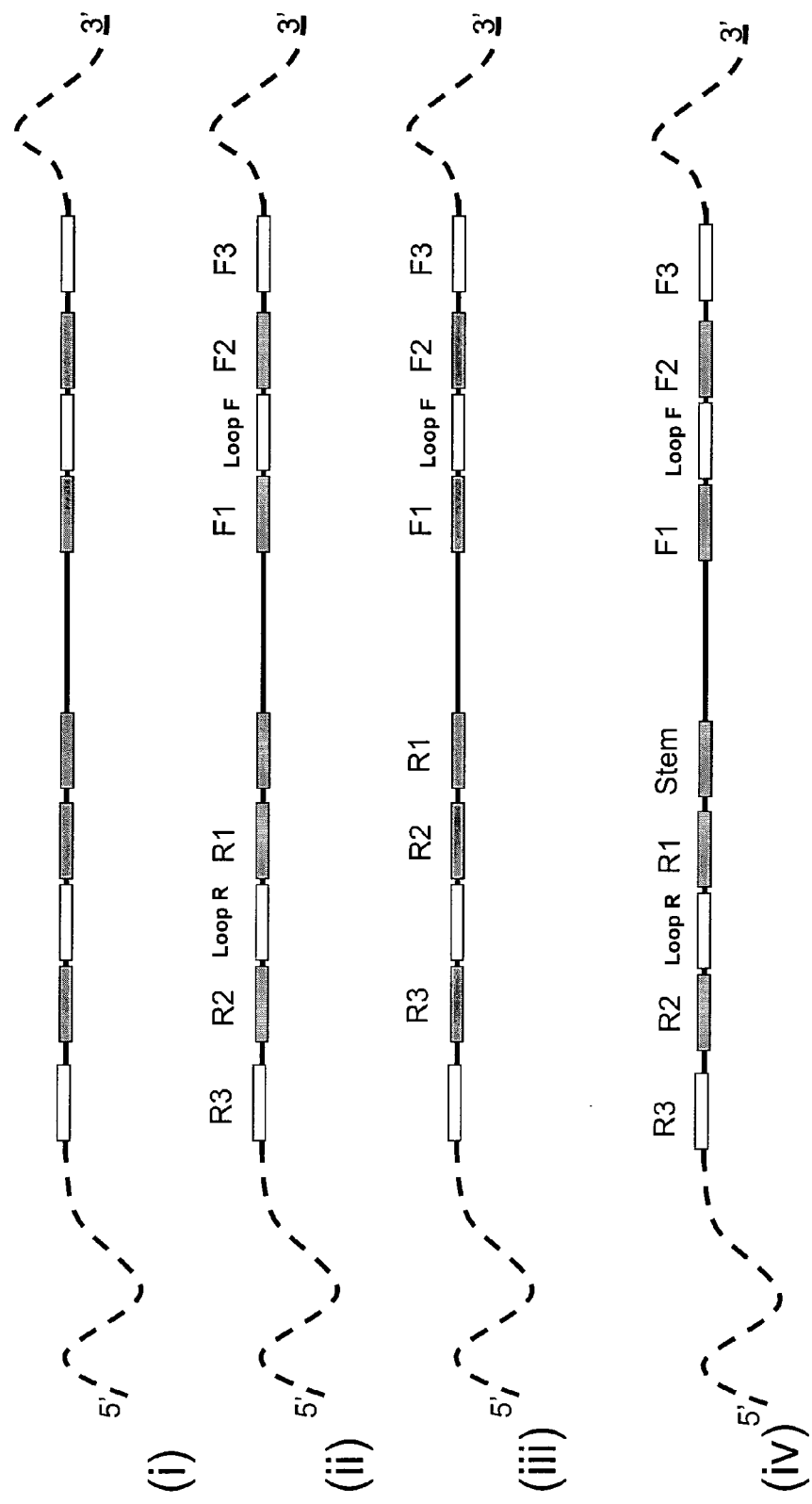

Showing (i) a hypothetical polynucleotide sequences where suitable primer binding sites are shown as boxed regions. However, the regions in grey are substantially preferred binding sites than the regions in white, perhaps due to better sequence conservation at this part of an organism's genome (which has relevance when designing diagnostic tests for e.g. a pathogen which has significant sequence variation between different strains). In FIG. 19(ii), and with respect to LAMP as used with Loop Primers, the different regions are assigned to the primers used in this manifestation of LAMP. Note that four of the primers must be placed in non-optimal binding sites and one optimal binding site is not used at all. This is clearly non-ideal. An alternative would be to position the primers as shown in FIG. 19(iii), where all the optimal sites are now used. However, in this manifestation the R2 and R1 sites are very close together which means loosing a site for the Loop R primer altogether; the Inventors have also seen that where the R1 and R2 sites are very close together (or the reciprocal F1 and F2 sites) non-optimal amplification may occur, perhaps dues to steric hindrance in the formed loop, the Inventors have further observed that loop primers generally increase the rate of amplification more than displacing primers. As such the assignment of primers in FIG. 19(iii) can be expected to be particularly non-ideal. However, in FIG. 19(iv), by employing the use of a stem primer, all the optimal binding sites can be used and all the loop and displacement primer sites can be made use of. Hence stem primers increased flexibility for primer design

FIG. 20

Figure 20:
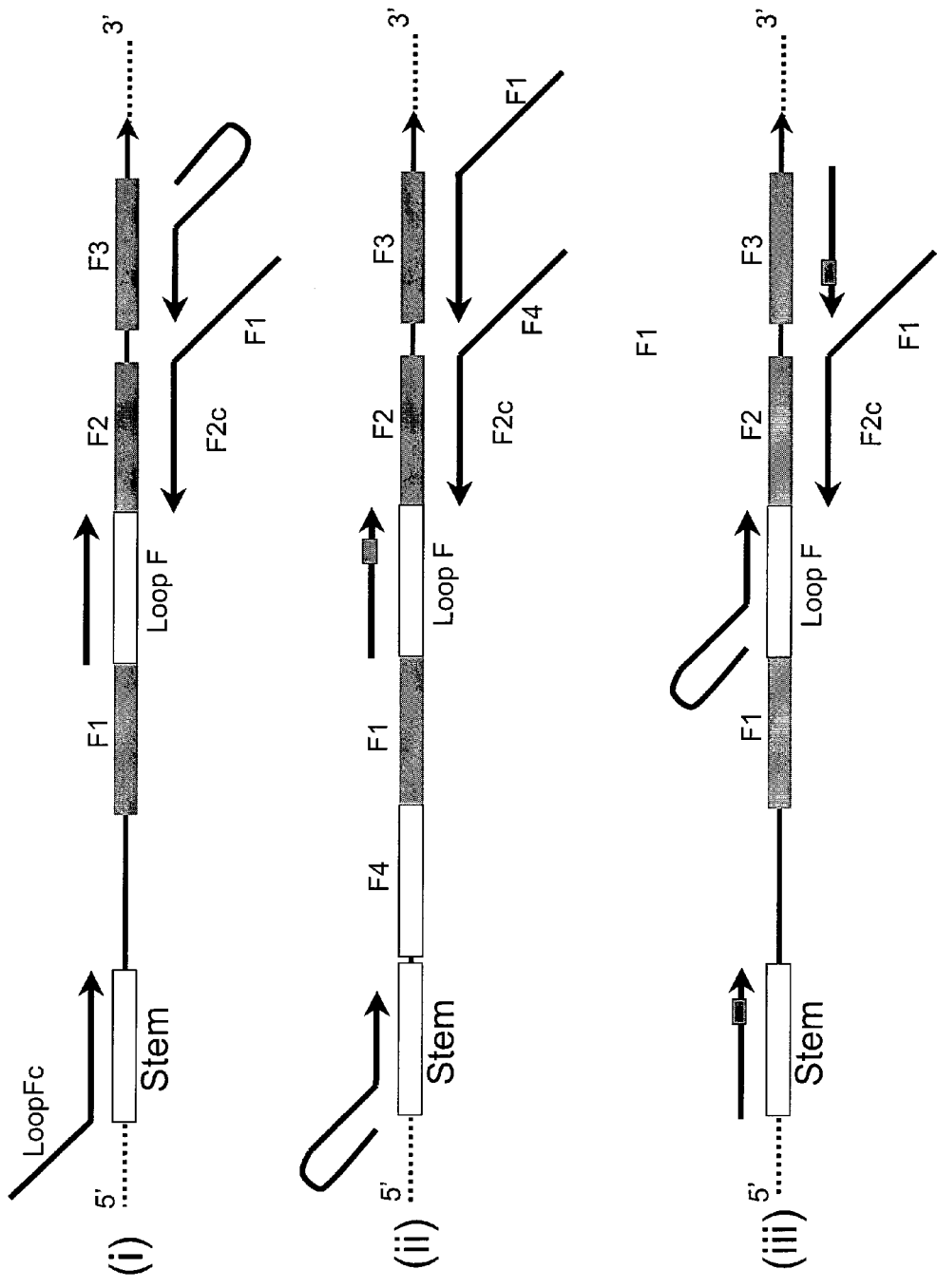

Showing that for both displacer primers, loop primers and stem primers, it is possible to employ various types of primers other than 'simple primers'. Three of many possible combinations are shown in FIG. 20 (i) to (iii) where only the forward reciprocal primer binding region and stem region are shown. In (i) a combination of LFP, hairpin primer and simple primer are employed; in (ii) the loop primer is represented by a modified simple primer which contains either a region of RNA or a cleavage site for a nickase; in (iii) a still further possible combination of LFP, hairpin primer and cleavable simple primers are shown. Many other possible combinations are clearly evident.

FIG. 21

Figure 21:
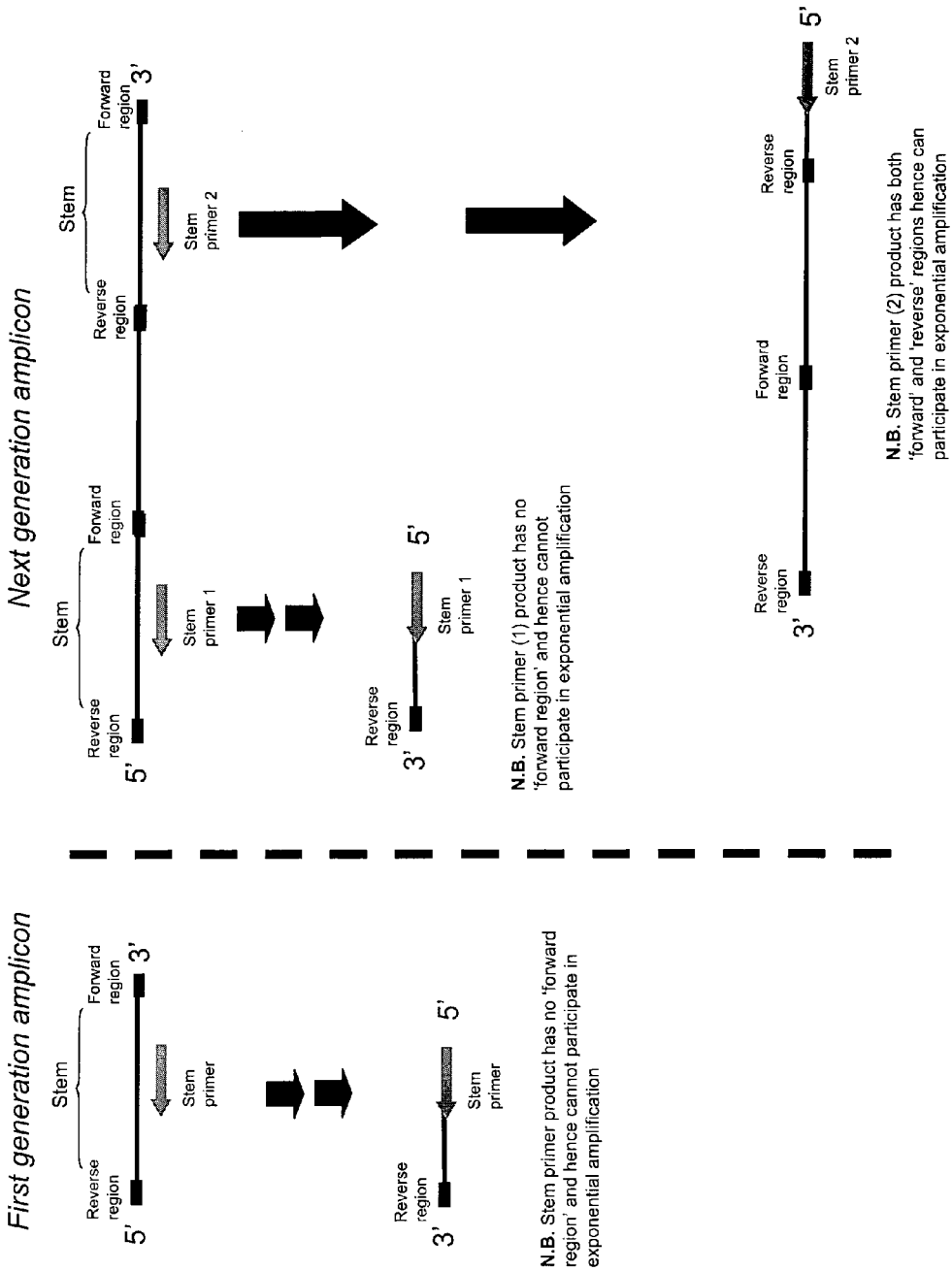
Figure 22:
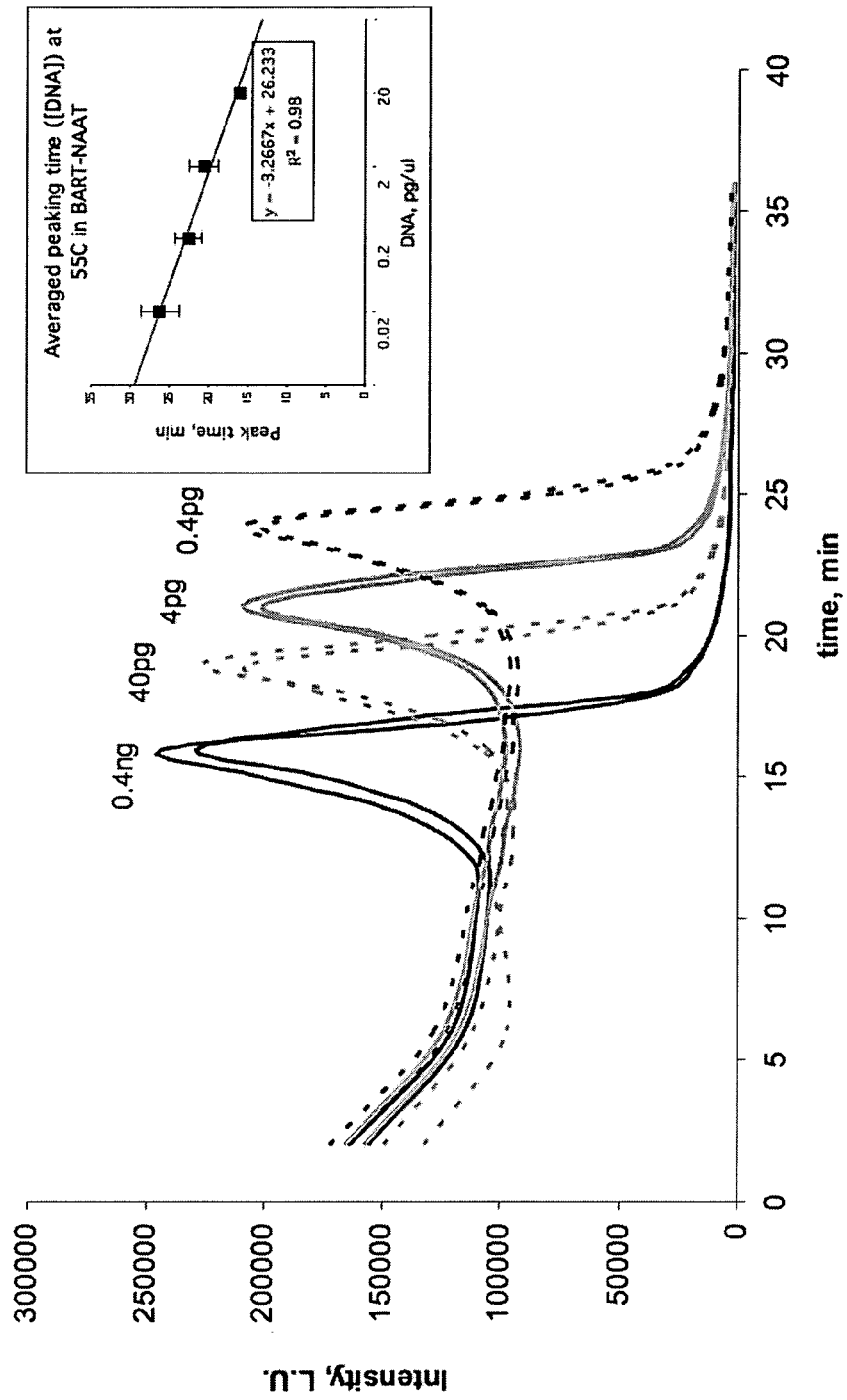
Figure 23:
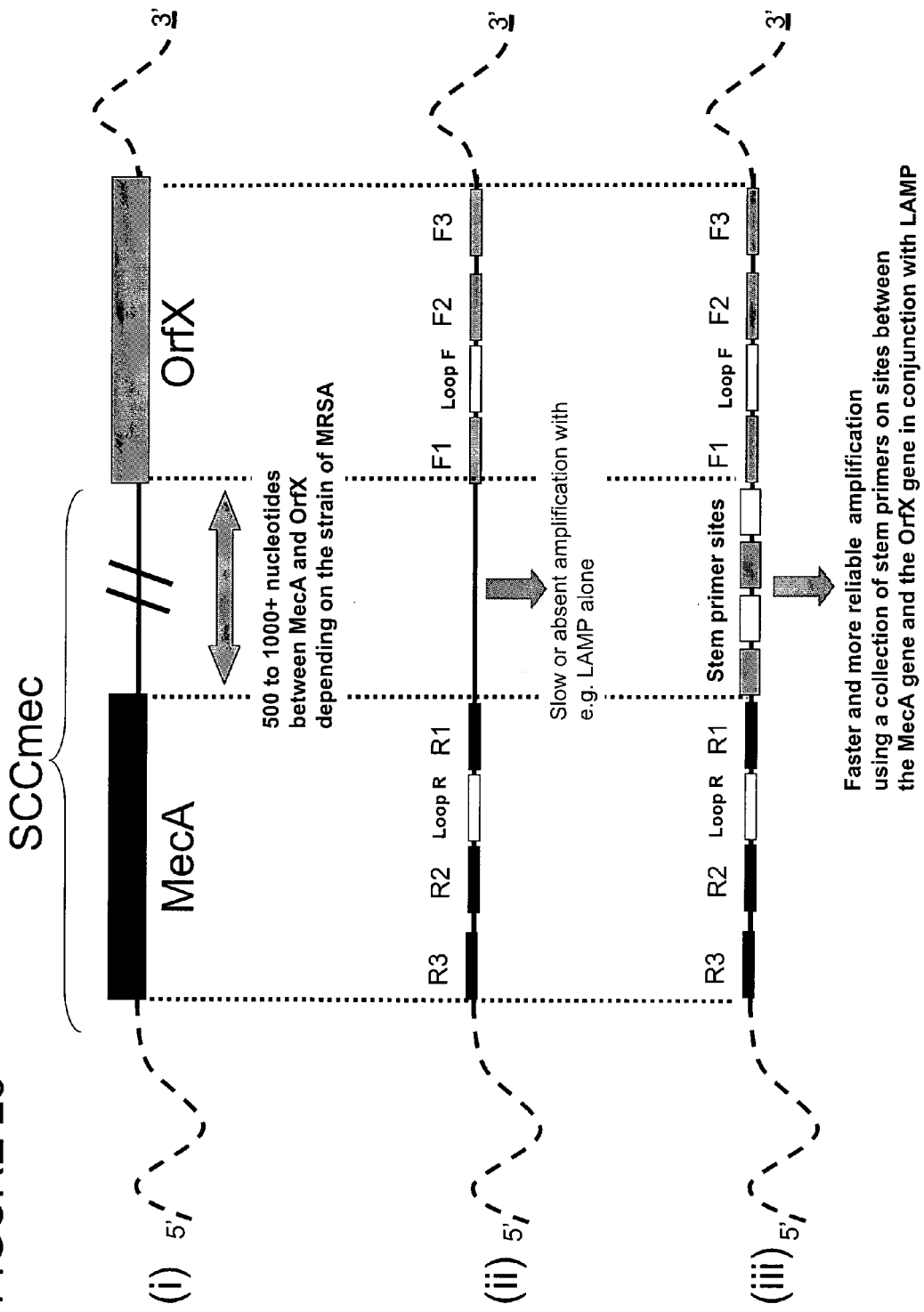

Showing that the action of stem primers only generates exponentially amplifiable amplicon if it acts on a concatamer. To the left of FIG. 21 the action of stem primer on First Generation Amplicon is shown: it can be seen that the resultant amplicon contains only the reverse and not the forward reciprocal primer binding regions required for exponential amplification. To the right of FIG. 21, in contrast, one sees that when the stem primer can extend through a concatamer, as is true for the shown stem primer 2 but not stem primer 1, the resulting amplicon has both forward and reverse reciprocal primer binding regions and hence is a substrate for exponential amplification.

FIG. 22

An example of BART-NAAT is shown highlighting the quantitative nature of the technique. The BART technology represents an effective means to follow the rate of amplification in a NAAT since the bioluminescent output reflects the instantaneous rate of amplification.

FIG. 23

Showing (i) a representation of part of the SCCmec cassette associated with MRSA. The SCCmec mobile genetic element integrates into a conserved region in the OrfX gene of Staphylococcus aureus conveying resistance to the antibiotic Methicillin via the MecA gene. The MecA gene and the OrfX gene are therefore on the same DNA strand however the distance, in sequence, between the MecA gene and the OrfX gene can be highly variable between different versions of SCCmec (and hence different strains of MRSA). As such, it has proven technically challenging to use the MecA and OrfX genes as reciprocal primer binding regions for a particular NAAT in a diagnostic assay for MRSA. For example, if the MecA and OrfX gene are greater than 500 base-pairs apart, it is unlikely that LAMP would be able to amplify any product if the MecA and OrfX genes where used as sites for the forward and reverse reciprocal primer binding sites (ii). However, since stem primers dramatically improve the ability of NAATs such as LAMP to amplify targets and since the 'stem' of an amplicon using MecA and OrfX as forward and reverse reciprocal primer binding sites could be targeted by several stem primers and since stem primers have been shown to work in a coupled fashion with the forward and reverse reciprocal primers, stem primers can therefore allow for the direct detection of MRSA using an appropriate NAAT such as LAMP(iii). A variety of stem primers can be employed to address the variations in the region between the MecA gene and OrfX.

The use of stem primers as described above has the benefit over existing techniques which rely only on OrfX and regions of the SCCmec other than MecA to indicate the presence of MRSA. This is because some Staphylococcus aureus contain a SCCmec insert which has no MecA gene and hence are not, actually, MRSA. Since the present method requires both OrfX and MecA to be on the same DNA strand there is no chance of obtaining a false positive from strains containing SCCmec but no MecA gene.

EXAMPLES

Example 1

Comparison of LAMP and TRA Showing that the Resulting Amplicons are in Both Cases Concatamers and Apparently Identical 2-kb fragment of *Salmonella enteritidis* invasion A gene (copy number varied between $10^8$ and $10^2$ per reaction) was amplified in LAMP-BART and TRA-BART at 60° C. on a Lucy, bespoke imaging hardware system (Lumora) under the conditions identical to those in Example 2 with the exception of using 0.32 U/µl Bst DNA Polymerase (NEB) and 11.2 µg/µl firefly luciferase. The reaction mixture contained R-LFP(6) and F-LFP(6) primers at 0.8 µM each and displacement primers RD(2) and FD(2) at 0.2 µM. Total volume of each reaction was 20 µl. Reactions were run for 100 min.

```
LFP primers set 6 (R-LFP binds R2c and F-LFP binds
F2 on the target sequence)
R-LFP(6)
5'-aac ctt gta gag cat att cgt ggt ttt ccg cca ttg gcg aat tta tg F-LFP(6)
5'-tct ctt ggc gcc cac aat gtt ttt aag cga acg tgt ttc cg Displacement primers set 2 (RD binds R3c and FD
binds F3 on the target sequence)
RD(2)
5'-cat tac tgc tcg taa ttc FD(2)
5'-ata tct gaa gtt ttg cag c
```

Figure 7:
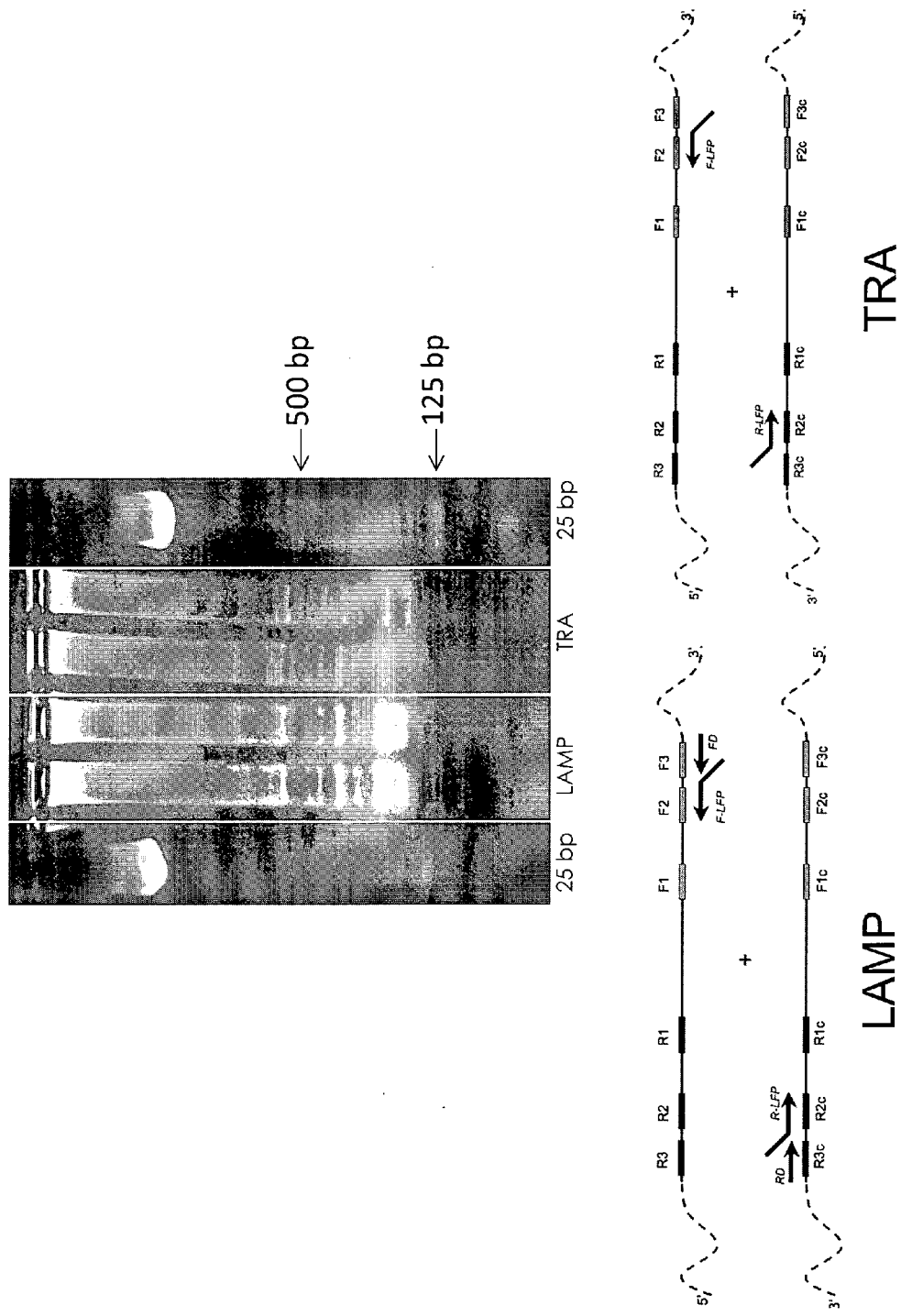

The pattern on the gel does not depend on the presence/absence of Displacement primers RD & FD and is defined by LFPs only (FIG. 7). Both LAMP and TRA amplifications result in ladders of exactly the same pattern strongly indicating that they occur through a similar mechanism. The displacement primers may play a significant role in the initiation stage of LAMP amplification but they do not show any effect on the subsequent amplicon propagation stage.

Example 2

Effect of Stem Primers on *Listeria monocytogenes* TRA with Lamp Primers of Different Efficiency pLS-plasmid containing a fragment of *Listeria monocytogenes* internalin A gene was purified using QIAprep Spin Miniprep Kit (Qiagen) and amplified using TRA-BART at 55° C. on a Lucy, bespoke imaging hardware system (Lumora). The reaction mixture contained: R-LFP 1, 2 or 3 and F-LFP1, 2 or 3 primers at 0.8 µM each (slow, medium or fast), 0.8 µM StemR and 0.8 µM StemF primers (Eurofins MWG), 0.8 mM dNTPs (total) (Invitrogen), 0.16 U/µl Bst DNA Polymerase (NEB), 0.1 mg/ml luciferin (Europa Bioproducts), 0.25 mM adenosine 5'-phosphosulphate (Biolog), 5.6 µg/µl firefly luciferase (UltraGlow, Promega), 0.375 U/ml ATP-sulphurylase (NEB) in 1× Thermopol buffer (NEB) with some stabilisers and additives and high or low amount of plasmid: $10^8$ or $10^4$. Total volume of each reaction was 20 µl.

Tests were run for 100 min. The relative orientation of the primers on the target template are depicted in FIG. 11(i) however, as can be seen from the sequence listing below, the primers actually used differ significantly in the sequence of the B2c and F2 binding regions.

(R-LFPs binds R2c and F-LFPs binds F2 on the
target sequence)
Slow LFPs set 1
R-LFP(1)
5'-cct tct ttt aca ggc tta gct ggt ttt tca aag aaa caa cca aag aag tgg F-LFP(1)
5'-gga att tca gta cgg ata aaa tgc cgt ttt att atc aaa cgt tgc tgt gta gc Medium LFPs set 2
R-LFP(2)
5'-cct tct ttt aca ggc tta gct ggt ttt atg cta agt ttc atg tgg acg F-LFP(2)
5'-gga att tca gta cgg ata aaa tgc cgt ttt gtt tga gat gtt gtt aca ccg tc Fast LFPs set 3
R-LFP(3)
5'-cct tct ttt aca ggc tta gct ggt ttt gga agc tgg gaa ttt att gag tg F-LFP(3)
5'-gga att tca gta cgg ata aaa tgc cgt ttt gcg cat ata aat cga tgt cat ttg Stem primers set 1
StemF(1)
5'-tca aac cac cca aca aat g StemR(1)
5'-aac cgg cgg aac taa at In the presence of stem primers the amplification occurred much faster for any set of LFP primers or amount of target present. For the slow and medium LFP primer sets (FIG. 11 (ii) and (iii) respectively) only $10^8$ copies of the target were detectable in the absence of stem primers peaking at 92 and 73 min correspondingly, while in their presence $10^8$ copies peaked at 39 and 41 min and $10^4$ was detectable as well within the time of the assay with peaks at 55 and 62 min. In case of the fast primers set 3 (FIG. 11(iv)) both low and high copy number peaked at 39 and 60 min, while in the presence of stem primers they were detected much earlier with peaks at 22 and 34 min. The example demonstrates that essential acceleration of amplification can be achieved by the addition of stem primers to sets of LFP primers of different efficiencies, length, location, Tms, GC-richness, size of the forming loop and other parameters.

Example 3

Comparison of Symmetrical, Asymmetrical and Stem-Accelerated Symmetrical *Listeria monocytogenes* TRA pLS-plasmid containing a fragment of *Listeria monocytogenes* internalin A (IlnA) gene was amplified at 55° C. on a Lucy, bespoke imaging hardware system (Lumora) under the conditions identical to those in Example 2 with high or low amount of plasmid: $10^8$ or $10^4$ using different combinations of R-LFP(3), F-LFP(3), StemB(1) and StemF(1) primers at 0.8 μM each.

```
LFP primers set 3
(R-LFPs binds R2c and F-LFPs binds F2 on the
target sequence)
R-LFP(3)
5'-cct tct ttt aca ggc tta gct ggt ttt gga agc tgg gaa ttt att gag tg F-LFP(3)
5'-gga att tca gta cgg ata aaa tgc cgt ttt gcg cat ata aat cga tgt cat ttg Stem primers set 1
StemF(1)
5'-tca aac cac cca aca aat g StemR(1)
5'-aac cgg cgg aac taa at
```

Both asymmetrical amplifications were very slow and detected only high copy number of the Listeria In1A target with peaks at 84 and 75 minutes, respectively. Symmetrical TRA involving the same set of LFPs showed much higher rates of amplification with peaks at 38 min for $10^8$ copies and 56 min for $10^4$ copies. When stem primers were added to the symmetrical manifestation of TRA high copy number peaked at 23 min and low copy number peaked at 34 min, therefore demonstrating a significant increase in comparison with the rates observed in their absence (FIG. 12*b*). The simple addition of three slower rates would not be sufficient to explain such a significant increase in the amplification rate as has been demonstrated also by mathematic modelling (example 4).

Example 4

Simulated BART kinetic curves were generated on Microsoft Excel using the standard Richard's curve formulae for modelling exponential processes (FIG. 13). Amplification kinetics were modelled for separate amplification processes with different kinetics. The effect of combining separate amplification processes of differing, similar or identical kinetics is also shown in FIG. 13. It can be seen from a comparison of FIGS. 13*a,b* and *c*, that the overall effect of combining separate distinct amplification processes on the overall rate of amplification is surprisingly small, even when three fast amplification processes are combined (FIG. 13*c*). This emphasises that the effect of stem primers is to fundamentally increase the rate of amplification rather than to simply add additional amplification processes.

Example 5

(A) Comparison of the Effect of Displacement Primers and Outer Loop-Forming Primers on *Listeria monocytogenes* Stem-Accelerated TRA pLS-plasmid containing a fragment of *Listeria monocytogenes* In1A gene was amplified in LAMP-BART at 55° C. on a Lucy, bespoke imaging hardware system (Lumora) under the conditions identical to those in Example 2 with high or low amount of plasmid: $10^8$ or $10^4$. Total volume of each reaction was 20 μA Tests were run for 100 min. A comparison was made between the reactions containing R-LFP(3), F-LFP (3), StemF(1) and StemR(1) at 0.8 μM each and an addition of OuterR(1) and OuterF(1) or Outer R-LFP(7) and Outer F-LFP(7) at 0.8 μM each.

LFP primers set 3
R-LFP(3)
5'-cct tct ttt aca ggc tta gct ggt ttt gga agc tgg gaa ttt att gag tg F-LFP(3)
5'-gga att tca gta cgg ata aaa tgc cgt ttt gcg cat ata aat cga tgt cat ttg Stem primers set 1
StemF(1)
5'-tca aac cac cca aca aat g StemR(1)
5'-aac cgg cgg aac taa at Displacement primers set1
RD(1)
5'-taa tgc taa gtt tca tgt g FD(1)
5'-ata atc tac tgt ttg aga tg Outer LFP primers set 7
R-LFP(7)
5'-ctt ctt tgg ttg ttt ctt tgc ctt ttt gct aag ttt cat gtg gac F-LFP(7)
5'-gta tta aca gct aca cag caa cgt ttt gag atg ttg tta cac cgt c Stem-accelerated TRA in this example results in fast amplification of the In1A gene at both $10^8$ and $10^4$ copy number peaking at 23 and 35 min, respectively. Addition of two different sets of Outer primers reduced the peaking times for high and low copy number down to 18 and 31 mM, correspondingly (FIG. 15a). When displacement primers are replaced by LFPs, the amplification reaction proceeds faster (FIG. 15a(iii)).

(B) Stem-Accelerated *Salmonella enteritidis* Nested TRA pLS-plasmid containing a fragment of *Salmonella enteritidis* invasion A (InvA) gene was purified using QIAprep Spin Miniprep Kit (Qiagen) and amplified in TRA-BART at 55° C. using the Lucy bespoke imaging hardware system (Lumora). The reaction mixture contained: inner and/or outer reverse and forward LFPs as indicated below at 0.8 µM each, 0.8 µM StemB and 0.8 µM StemF primers (Eurofins MWG), 1.6 mM dNTPs (total) (Invitrogen), 0.16 U/µl Bst DNA Polymerase (NEB), 0.1 mg/ml luciferin (Europa Bioproducts), 0.25 mM adenosine 5'-phosphosulphate (Biolog), 5.6 µl/µl firefly luciferase (Ultra Glow, Promega), 0.375 U/ml ATP-sulphurylase (NEB) in 1× Thermopol buffer (NEB) with some stabilisers and additives and high or low amount of plasmid: $10^8$ or $10^4$. Total volume of each reaction was 20 µl. Tests were run for 100 min.

Inner LFP primers set 4
R-LFP(4)
5'-gga gca atg gcg cgt tat att tgt ttt cgc cat tgg cga att tat g F-LFP(4)
5'-cac aat gcg agc gct tcc ttt tta agc gaa cgt gtt tcc g Outer LFP primers set 5
R-LFP(5)
5'-cga att acg agc agt aat ggt ttt tca tcc tca act tca gca g F-LFP(5)
5'-caa acg ctg caa aac ttc agt ttt tta aag aag tgc tca gac atg Stem primers set 2
StemF(2)
5'-cct tgt gga gca tat tcg StemB(2)
5'-gac atc ttt ttc tct tgg cg In this *Salmonella enteritidis* InvA TRA system both sets of LFPs used individually were so slow that they failed to detect even the higher $10^8$ target copy number within 100 min of the assay. In the Nested TRA in the absence of stem primers the amplification was fast enough to detect only the high target copy number which peaked at 68 min. When stem primers were added there was an increase in the speed and both high and low target copy became detectable with peak times of 34 and 61 min correspondingly (FIG. 15). This example demonstrates that acceleration of amplification with Stem primers is observed for different targets and different manifestations of LFPs.

Example 6

Stem-Accelerated *Listeria monocytogenes* LAMP pLS-plasmid containing a fragment of *Listeria monocytogenes* internalin A gene was amplified in LAMP-BART at 55° C. on a Lucy, bespoke imaging hardware system (Lumora) under the conditions identical to those in Example 2 with high or low amount of plasmid: $10^8$ or $10^4$. Total volume of each reaction was 20 Tests were run for 100 min. A comparison was made between the reactions containing full LAMP primers mix (0.8 µM each LFP, 0.4 µM each Loop primer, 0.2 µM each Displacing primer) and an addition of 0.8 µM StemR and 0.8 µM StemF primers.

LFP primers set 1
R-LFP(1)
5'-cct tct ttt aca ggc tta gct ggt ttt tca aag aaa caa cca aag aag tgg F-LFP(1)
5'-gga att tca gta cgg ata aaa tgc cgt ttt att atc aaa cgt tgc tgt gta gc Loop primers
LoopRc
5'-cag tca ata aat tcc cag c LoopF
5'-cat cga ttt ata tgc gca at Displacement primers set 1
RD(1)
5'-taa tgc taa gtt tca tgt g FD(1)
5'-ata atc tac tgt ttg aga tg Stem primers set 1
StemF(1)
5'-tca aac cac cca aca aat g StemR(1)
5'-aac cgg cgg aac taa at This is an example of LAMP amplification which very quickly detected high and low copy number of the *Listeria monocytogenes* In1A target. In the absence of stem primers $10^8$ copies peaked at 17 minutes and $10^4$ copies peaked at 26 minutes. Addition of Stem primers accelerated the reaction even further and reduced the peaking time down to 13 min for $10^8$ and 19 min for $10^4$ copies (FIG. 16). In this case the acceleration was achieved in LAMP, which is one of the most efficient isothermal amplification systems developed so far. Reduction of detection time is of huge importance for point-of-use applications in general and for point-of-care tests in medical diagnostics in particular.

Example 7

Accelerated *Listeria monocytogenes* TRA with Different Orientation of Stem Primers pLS-plasmid containing a fragment of *Listeria monocytogenes* internalin A gene was amplified in TRA-BART at 55° C. on a Lucy, bespoke imaging hardware system (Lumora) under the conditions identical to those in Example 2 with high or low amount of plasmid: $10^8$ or $10^4$. The comparison was made between the reactions run with R-LFP(3) and F-LFP(3) primers only in the absence and presence of StemR(3) and StemF(3) primers added at 0.8 µM each.

LFP primers set 3
R-LFP(3)
5'-cct tct ttt aca ggc tta gct ggt ttt gga agc tgg gaa ttt att gag tg F-LFP(3)
5'-gga att tca gta cgg ata aaa tgc cgt ttt gcg cat ata aat cga tgt cat ttg Stem primers set 3
StemF(3)
5'-agt tcc gcc ggt ttg StemR(3)
5'-aca ttt gtt ggg tgg ttt g In this example the accelerating effect of stem primers of different location on the stem of the amplicon as compared to that shown in Example 2 was demonstrated. TRA-BART detected both high and low copy target even in the absence of stem primers with peak times of 39 and 69 min correspondingly. The addition of stem primers significantly accelerated the reaction and reduced the peaking time down to 22 and 39 min. Unlike with Loop primers, when the location is strictly dictated by the loops formed by LFPs and the orientation is fixed, Stem primers can be located anywhere between the inner F1-B1 regions and can face in any direction. Acceleration effect is observed independent of the position or orientation of Stem primers (FIG. 17).

SEQUENCES
Listeria IlnA gene fragment
(SEQ ID NO: 1)
GGCAATTTTTAATGCTAAGTTTCATGTGGACGGCAAAGAAACAACCAAAG

AAGTGGAAGCTGGGAATTTATTGACTGAACCAGCTAAGCCTGTAAAAGAA

GG*T*TATACATTTGTTGGGTGGTTTGATGCCCAAACCGGCGGAACTAAAG

*T*GGAATTTCAGTACGGATAAAATGCCGACAAATGACATCGATTTATAT

GCGCAATTTAGTATTAACAGCTACACAGCAACGTTTGATAATGACGGTGT

AACAACATCTCAAACAGTAGATTATCA

Salmonella InvA gene fragment
(SEQ ID NO: 2)
TTTGCGAATAACATCCTCAACTTCAGCAGATACCATTACTGCTCGTAATT

CGCCGCCATTGGCGAATTTATGACAAATATAACGCGCCATTGCTCCACGA

ATATGCTCCACAAGGTTAATGACATCTTTTTCTCTTGGCGCCCACAATGC

GAGCGCTTCCATAATTAACTTCATATTACGCACGGAAACACGTTCGCTTA

ACAAACGCTGCAAAACTTCAGATATACGTTGTACCGTGGCATGTCTGAGC

ACTTCTTTAAGTAAATCAGGAAATTTCGCTTCCAGTTGGTCCAGCATATG

TTTTGTTTCCTGAATACC

---

The invention claimed is:

1. A method of synthesizing a polynucleic acid wherein said method comprises the steps of
   a) providing a target template which comprises at least a first and a second reciprocal primer binding region;
   b) providing a first primer comprising a first and a second segment, wherein the first segment is substantially complementary to the first reciprocal primer binding region on the template and the second segment comprises a sequence that is substantially complementary to another region in the first primer or a region in the amplicon generated from the first segment of the first primer such that the second segment is able to form a loop, wherein, when the first primer comprises a second segment that is substantially complementary to a region in the amplicon generated from the first segment of the first primer, the first reciprocal primer binding region also encompasses a region on the template which is substantially identical to the second segment of the first primer;
   c) providing a second primer comprising a first and optionally a second segment, wherein the first segment is substantially complementary to the second reciprocal primer binding region on the template and the optional second segment comprises a sequence that it substantially complementary to another region in the second primer or a region in the amplicon generated from the first segment of the second primer such that the second region is able to form a loop, wherein, when the second primer comprises a second segment that is substantially complementary to a region in the amplicon generated from the first segment of the second primer, the second reciprocal primer binding region also encompasses a region on the template which is substantially identical to the second segment of the second primer;
   d) providing at least one stem primer which is capable of binding to the region between the first and second reciprocal primer binding regions, wherein the at least one stem primer is
   (i) a simple primer, which is a primer that is complementary to a primer binding site on a polynucleic acid and which contains fewer than 5 nucleotides 3' or 5' of the primer region which is substantially complementary to the primer binding site;
   (ii) a loop-forming primer, which is a primer that comprises a first and a second segment, wherein the first segment is substantially complementary to a primer binding region on the template and the second segment comprises a sequence that is substantially complementary to a region in the amplicon generated from the first segment of the first primer such that the second segment is able to form a loop;
   (iii) a hairpin primer, which is a primer comprising a first and a second segment, wherein the first segment is substantially complementary to a primer binding region on a template and the second segment comprises a sequence that is substantially complementary to another region in the primer;

(iv) a loop-providing primer; which is a hairpin primer in which the inverted repeats are separated by a linker region; or (v) a chimeric primer;

e) providing the necessary reagents and conditions to perform synthesis of the polynucleic acid;

f) performing synthesis of the polynucleic acid.

2. The method of claim 1, wherein synthesis is performed using a nucleic acid amplification technique selected from the group consisting of Loop-mediated Isothermal Amplification (LAMP), Template Re-priming Amplification (TRA), Self Extending Amplification (SEA) and SMart Amplification Process (SMAP).

3. The method of claim 1 wherein the first and/or second reciprocal primer binding regions comprise binding sites for two or more primers.

4. The method of claim 3 wherein the two or more primers binding to the first and/or second reciprocal primer binding regions are of the same kind, wherein the kind of primer is selected from (i) through (v).

5. The method of claim 1 wherein the primers binding to the first and/or second reciprocal primer binding regions are loop-providing primers (LPPs).

6. The method of claim 4 wherein the two or more primers are loop-forming primers.

7. The method of claim 3 wherein the two or more primers binding to the first and/or second reciprocal primer binding regions are of a different kind, wherein the kind of primer is selected from (i) through (v).

8. The method of claim 3 wherein the two or more binding sites are all situated on the same strand of the target template and/or amplicon.

9. The method of claim 3 wherein the two or more binding sites are situated on different strands of the target template and/or amplicon.

10. The method of claim 1 wherein the first and second reciprocal primer binding sites are located at a distance such that synthesis of a polynucleic acid can occur only in the presence of the stem primer(s).

11. The method of claim 10, wherein the method is used to detect Methicillin-resistant *Staphylococcus aureus* (MRSA) in a sample.

12. The method of claim 11, wherein MRSA is detected using the mecA gene and the orfX sequence.

13. The method of claim 1, wherein in step (d) a single stem primer is used.

14. The method of claim 1, wherein in step (d) two or more stem primers are used.

15. The method of claim 14 wherein the two or more stem primers used in step (d) are of the same kind, wherein the kind of primer is selected from (i) through (v).

16. The method of claim 14 wherein the two or more stem primers used in step (d) are of a different kind, wherein the kind of primer is selected from (i) through (v).

17. The method of claim 14 wherein the two or more stem primers used in step (d) bind to reciprocal strands of the amplicon.

18. The method of claim 14 wherein the two or more stem primers used in step (d) bind to the same strand of the amplicon.

19. The method of claim 1 wherein the stem primer(s) contain(s) modified bases.

20. The method of claim 19 wherein the modified bases are selected from the group consisting of N4-methylcytosine, inosine, ribocleotides, fluorescent bases, photolysable bases and universal bases.

21. The method of claim 1 wherein the stem primer(s) contain(s) nucleic acids that have been labelled with a detectable moiety.

22. The method of claim 21 wherein the detectable moiety is a fluorescent label, a chemiluminescent label or an electrochemical label.

23. The method of claim 22, wherein the labelled stem primers are used as probes in a fluorescent, chemiluminescent or electrochemical reporter system.

24. The method of claim 1 further comprising detecting amplification of the polynucleic acid by a method selected from the group consisting of gene arrays, lateral flow strips, electrophoresis, mass spectroscopy and acoustic detection.

25. The method of claim 1 wherein the stem primer(s) contain(s) nucleic acids that have been labelled with a capture moiety.

26. The method of claim 25 wherein the capture moiety is biotin.

27. The method of claim 1 further comprising detecting synthesis of the nucleic acid using real-time measurements or end-point measurements.

28. The method of claim 27 wherein amplification of the polynucleic acid is detected with a detection system selected from the group consisting of fluorescence, bioluminescence, turbidity and electrochemical measurements.

29. The method of claim 28 wherein the synthesis of the nucleic acid is detected using the Bioluminescent Assay in Real-Time (BART) reporter system.

30. The method of claim 1 wherein the method is performed in a sealed vessel.

31. The method of claim 1 for determining the presence of a particular polynucleic acid sequence in an organism's genetic code, wherein the target template is polynucleic acid from said organism.

32. The method of claim 1 for the detection of single-nucleotide polymorphisms (SNPs), wherein the target template is polynucleic acid that potentially comprises said SNPs.

33. The method of claim 1 for use in diagnostic applications, wherein the target template is polynucleic acid associated with the disease or condition to be diagnosed.

34. The method of claim 1 for use in detecting or quantifying an organism in a sample, wherein the target template is polynucleic acid from said organism.

35. The method of claim 34, wherein the organism is a microorganism.

36. The method of claim 35 wherein the microorganism is selected from the group consisting of viruses, bacteria, mycoplasma and fungi.

37. The method of claim 35 wherein the microorganism is a genetically modified organism (GMO).

38. The method of claim 1 for identifying genetically modified crops, identifying genetically modified animals, detecting a disease state, predicting an adverse reaction from therapy or predicting disease state susceptibility, wherein the target template is polynucleic acid from said genetically modified crops, from said genetically modified animals, associated with said disease state, associated with said adverse reaction from therapy, or associated with said disease state susceptibility, respectively.

39. The method of claim 1, wherein the stem primer contains a nickase site.

* * * * *

SEQUENCE LISTING

<160> NUMBER OF SEQ ID NOS: 44

<210> SEQ ID NO 1
<211> LENGTH: 273
<212> TYPE: DNA
<213> ORGANISM: Listeria monocytogenes

<400> SEQUENCE: 1
ggcaattttt aatgctaagt tcatgtgga cggcaaagaa acaaccaaag aagtggaagc      60
tgggaattta ttgactgaac cagctaagcc tgtaaaagaa ggttatacat tgttgggtg    120 gtttgatgcc caaaccggcg gaactaaatg gaatttcagt acggataaaa tgccgacaaa   180
tgacatcgat ttatatgcgc aatttagtat taacagctac acagcaacgt ttgataatga   240
cggtgtaaca acatctcaaa cagtagatta tca                                273

<210> SEQ ID NO 2
<211> LENGTH: 318
<212> TYPE: DNA

<213> ORGANISM: Salmonella enteritidis

<400> SEQUENCE: 2

```
tttgcgaata acatcctcaa cttcagcaga taccattact gctcgtaatt cgccgccatt    60
ggcgaattta tgacaaatat aacgcgccat tgctccacga atatgctcca caaggttaat   120
gacatctttt tctcttggcg cccacaatgc gagcgcttcc ataattaact tcatattacg   180
cacggaaaca cgttcgctta acaaacgctg caaaacttca gatatacgtt gtaccgtggc   240
atgtctgagc acttctttaa gtaaatcagg aaatttcgct tccagttggt ccagcatatg   300
ttttgttttcc tgaatacc                                                318
```

<210> SEQ ID NO 3
<211> LENGTH: 47
<212> TYPE: DNA
<213> ORGANISM: Artificial Sequence
<220> FEATURE:
<223> OTHER INFORMATION: Primer sequence

<400> SEQUENCE: 3

```
aaccttgtag agcatattcg tggttttccg ccattggcga atttatg                  47
```

<210> SEQ ID NO 4
<211> LENGTH: 41
<212> TYPE: DNA
<213> ORGANISM: Artificial Sequence
<220> FEATURE:
<223> OTHER INFORMATION: Primer sequence

<400> SEQUENCE: 4

```
tctcttggcg cccacaatgt ttttaagcga acgtgtttcc g                        41
```

<210> SEQ ID NO 5
<211> LENGTH: 18
<212> TYPE: DNA
<213> ORGANISM: Artificial Sequence
<220> FEATURE:
<223> OTHER INFORMATION: Primer sequence

<400> SEQUENCE: 5

```
cattactgct cgtaattc                                                  18
```

<210> SEQ ID NO 6
<211> LENGTH: 19
<212> TYPE: DNA
<213> ORGANISM: Artificial Sequence
<220> FEATURE:
<223> OTHER INFORMATION: Primer sequence

<400> SEQUENCE: 6

```
atatctgaag ttttgcagc                                                 19
```

<210> SEQ ID NO 7
<211> LENGTH: 51
<212> TYPE: DNA
<213> ORGANISM: Artificial Sequence
<220> FEATURE:
<223> OTHER INFORMATION: Primer sequence

<400> SEQUENCE: 7

```
ccttcttttta caggcttagc tggtttttca aagaaacaac caaagaagtg g            51
```

<210> SEQ ID NO 8
<211> LENGTH: 53

-continued

<212> TYPE: DNA
<213> ORGANISM: Artificial Sequence
<220> FEATURE:
<223> OTHER INFORMATION: Primer sequence

<400> SEQUENCE: 8
ggaatttcag tacggataaa atgccgtttt attatcaaac gttgctgtgt agc         53

<210> SEQ ID NO 9
<211> LENGTH: 48
<212> TYPE: DNA
<213> ORGANISM: Artificial Sequence
<220> FEATURE:
<223> OTHER INFORMATION: Primer sequence

<400> SEQUENCE: 9
ccttctttta caggcttagc tggttttatg ctaagtttca tgtggacg               48

<210> SEQ ID NO 10
<211> LENGTH: 53
<212> TYPE: DNA
<213> ORGANISM: Artificial Sequence
<220> FEATURE:
<223> OTHER INFORMATION: Primer sequence

<400> SEQUENCE: 10
ggaatttcag tacggataaa atgccgtttt gtttgagatg ttgttacacc gtc         53

<210> SEQ ID NO 11
<211> LENGTH: 50
<212> TYPE: DNA
<213> ORGANISM: Artificial Sequence
<220> FEATURE:
<223> OTHER INFORMATION: Primer sequence

<400> SEQUENCE: 11
ccttctttta caggcttagc tggttttgga agctgggaat ttattgagtg             50

<210> SEQ ID NO 12
<211> LENGTH: 54
<212> TYPE: DNA
<213> ORGANISM: Artificial Sequence
<220> FEATURE:
<223> OTHER INFORMATION: Primer sequence

<400> SEQUENCE: 12
ggaatttcag tacggataaa atgccgtttt gcgcatataa atcgatgtca tttg        54

<210> SEQ ID NO 13
<211> LENGTH: 19
<212> TYPE: DNA
<213> ORGANISM: Artificial Sequence
<220> FEATURE:
<223> OTHER INFORMATION: Primer sequence

<400> SEQUENCE: 13
tcaaaccacc caacaaatg                                              19

<210> SEQ ID NO 14
<211> LENGTH: 17
<212> TYPE: DNA
<213> ORGANISM: Artificial Sequence
<220> FEATURE:
<223> OTHER INFORMATION: Primer sequence

<400> SEQUENCE: 14

-continued aaccggcgga actaaat                                                   17

<210> SEQ ID NO 15
<211> LENGTH: 50
<212> TYPE: DNA
<213> ORGANISM: Artificial Sequence
<220> FEATURE:
<223> OTHER INFORMATION: Primer sequence

<400> SEQUENCE: 15 ccttcttta caggcttagc tggttttgga agctgggaat ttattgagtg               50

<210> SEQ ID NO 16
<211> LENGTH: 54
<212> TYPE: DNA
<213> ORGANISM: Artificial Sequence
<220> FEATURE:
<223> OTHER INFORMATION: Primer sequence

<400> SEQUENCE: 16
ggaatttcag tacggataaa atgccgtttt gcgcatataa atcgatgtca tttg         54

<210> SEQ ID NO 17
<211> LENGTH: 19
<212> TYPE: DNA
<213> ORGANISM: Artificial Sequence
<220> FEATURE:
<223> OTHER INFORMATION: Primer sequence

<400> SEQUENCE: 17
tcaaaccacc caacaaatg                                                 19

<210> SEQ ID NO 18
<211> LENGTH: 17
<212> TYPE: DNA
<213> ORGANISM: Artificial Sequence
<220> FEATURE:
<223> OTHER INFORMATION: Primer sequence

<400> SEQUENCE: 18
aaccggcgga actaaat                                                   17

<210> SEQ ID NO 19
<211> LENGTH: 50
<212> TYPE: DNA
<213> ORGANISM: Artificial Sequence
<220> FEATURE:
<223> OTHER INFORMATION: Primer sequence

<400> SEQUENCE: 19 ccttcttta caggcttagc tggttttgga agctgggaat ttattgagtg               50

<210> SEQ ID NO 20
<211> LENGTH: 54
<212> TYPE: DNA
<213> ORGANISM: Artificial Sequence
<220> FEATURE:
<223> OTHER INFORMATION: Primer sequence

<400> SEQUENCE: 20
ggaatttcag tacggataaa atgccgtttt gcgcatataa atcgatgtca tttg         54

<210> SEQ ID NO 21
<211> LENGTH: 19
<212> TYPE: DNA
<213> ORGANISM: Artificial Sequence

```
<220> FEATURE:
<223> OTHER INFORMATION: Primer sequence

<400> SEQUENCE: 21
tcaaaccacc caacaaatg                                                   19

<210> SEQ ID NO 22
<211> LENGTH: 17
<212> TYPE: DNA
<213> ORGANISM: Primer sequence

<400> SEQUENCE: 22
aaccggcgga actaaat                                                     17

<210> SEQ ID NO 23
<211> LENGTH: 19
<212> TYPE: DNA
<213> ORGANISM: Artificial Sequence
<220> FEATURE:
<223> OTHER INFORMATION: Primer sequence

<400> SEQUENCE: 23
taatgctaag tttcatgtg                                                   19

<210> SEQ ID NO 24
<211> LENGTH: 20
<212> TYPE: DNA
<213> ORGANISM: Artificial Sequence
<220> FEATURE:
<223> OTHER INFORMATION: Primer sequence

<400> SEQUENCE: 24
ataatctact gtttgagatg                                                  20

<210> SEQ ID NO 25
<211> LENGTH: 45
<212> TYPE: DNA
<213> ORGANISM: Artificial Sequence
<220> FEATURE:
<223> OTHER INFORMATION: Primer sequence

<400> SEQUENCE: 25
cttctttggt tgtttctttg ccttttttgct aagtttcatg tggac                     45

<210> SEQ ID NO 26
<211> LENGTH: 46
<212> TYPE: DNA
<213> ORGANISM: Artificial Sequence
<220> FEATURE:
<223> OTHER INFORMATION: Primer sequence

<400> SEQUENCE: 26
gtattaacag ctacacagca acgttttgag atgttgttac accgtc                     46

<210> SEQ ID NO 27
<211> LENGTH: 46
<212> TYPE: DNA
<213> ORGANISM: Artificial Sequence
<220> FEATURE:
<223> OTHER INFORMATION: Primer sequence

<400> SEQUENCE: 27
ggagcaatgg cgcgttatat ttgttttcgc cattggcgaa tttatg                     46

<210> SEQ ID NO 28
```

<211> LENGTH: 40
<212> TYPE: DNA
<213> ORGANISM: Artificial Sequence
<220> FEATURE:
<223> OTHER INFORMATION: Primer sequence

<400> SEQUENCE: 28
cacaatgcga gcgcttcctt tttaagcgaa cgtgtttccg        40

<210> SEQ ID NO 29
<211> LENGTH: 43
<212> TYPE: DNA
<213> ORGANISM: Artificial Sequence
<220> FEATURE:
<223> OTHER INFORMATION: Primer sequence

<400> SEQUENCE: 29
cgaattacga gcagtaatgg tttttcatcc tcaacttcag cag        43

<210> SEQ ID NO 30
<211> LENGTH: 45
<212> TYPE: DNA
<213> ORGANISM: Artificial Sequence
<220> FEATURE:
<223> OTHER INFORMATION: Primer sequence

<400> SEQUENCE: 30
caaacgctgc aaaacttcag ttttttaaag aagtgctcag acatg        45

<210> SEQ ID NO 31
<211> LENGTH: 18
<212> TYPE: DNA
<213> ORGANISM: Artificial Sequence
<220> FEATURE:
<223> OTHER INFORMATION: Primer sequence

<400> SEQUENCE: 31
ccttgtggag catattcg        18

<210> SEQ ID NO 32
<211> LENGTH: 20
<212> TYPE: DNA
<213> ORGANISM: Artificial Sequence
<220> FEATURE:
<223> OTHER INFORMATION: Primer sequence

<400> SEQUENCE: 32
gacatctttt tctcttggcg        20

<210> SEQ ID NO 33
<211> LENGTH: 51
<212> TYPE: DNA
<213> ORGANISM: Artificial Sequence
<220> FEATURE:
<223> OTHER INFORMATION: Primer sequence

<400> SEQUENCE: 33
ccttctttta caggcttagc tggttttca aagaaacaac caaagaagtg g        51

<210> SEQ ID NO 34
<211> LENGTH: 53
<212> TYPE: DNA
<213> ORGANISM: Artificial Sequence
<220> FEATURE:
<223> OTHER INFORMATION: Primer sequence

<400> SEQUENCE: 34

```
ggaatttcag tacggataaa atgccgtttt attatcaaac gttgctgtgt agc    53
```

```
<210> SEQ ID NO 35
<211> LENGTH: 19
<212> TYPE: DNA
<213> ORGANISM: Artificial Sequence
<220> FEATURE:
<223> OTHER INFORMATION: Primer sequence

<400> SEQUENCE: 35
cagtcaataa attcccagc                                          19

<210> SEQ ID NO 36
<211> LENGTH: 20
<212> TYPE: DNA
<213> ORGANISM: Artificial Sequence
<220> FEATURE:
<223> OTHER INFORMATION: Primer sequence

<400> SEQUENCE: 36
catcgattta tatgcgcaat                                         20

<210> SEQ ID NO 37
<211> LENGTH: 19
<212> TYPE: DNA
<213> ORGANISM: Artificial Sequence
<220> FEATURE:
<223> OTHER INFORMATION: Primer sequence

<400> SEQUENCE: 37
taatgctaag tttcatgtg                                          19

<210> SEQ ID NO 38
<211> LENGTH: 20
<212> TYPE: DNA
<213> ORGANISM: Artificial Sequence
<220> FEATURE:
<223> OTHER INFORMATION: Primer sequence

<400> SEQUENCE: 38
ataatctact gtttgagatg                                         20

<210> SEQ ID NO 39
<211> LENGTH: 19
<212> TYPE: DNA
<213> ORGANISM: Artificial Sequence
<220> FEATURE:
<223> OTHER INFORMATION: Primer sequence

<400> SEQUENCE: 39
tcaaaccacc caacaaatg                                          19

<210> SEQ ID NO 40
<211> LENGTH: 17
<212> TYPE: DNA
<213> ORGANISM: Artificial Sequence
<220> FEATURE:
<223> OTHER INFORMATION: Primer sequence

<400> SEQUENCE: 40
aaccggcgga actaaat                                            17

<210> SEQ ID NO 41
<211> LENGTH: 50
<212> TYPE: DNA
```

```
<213> ORGANISM: Artificial Sequence
<220> FEATURE:
<223> OTHER INFORMATION: Primer sequence

<400> SEQUENCE: 41 ccttcttta caggcttagc tggttttgga agctgggaat ttattgagtg        50

<210> SEQ ID NO 42
<211> LENGTH: 54
<212> TYPE: DNA
<213> ORGANISM: Artificial Sequence
<220> FEATURE:
<223> OTHER INFORMATION: Primer sequence

<400> SEQUENCE: 42
ggaatttcag tacggataaa atgccgtttt gcgcatataa atcgatgtca tttg   54

<210> SEQ ID NO 43
<211> LENGTH: 15
<212> TYPE: DNA
<213> ORGANISM: Artificial Sequence
<220> FEATURE:
<223> OTHER INFORMATION: Primer sequence

<400> SEQUENCE: 43
agttccgccg gtttg                                             15

<210> SEQ ID NO 44
<211> LENGTH: 19
<212> TYPE: DNA
<213> ORGANISM: Artificial Sequence
<220> FEATURE:
<223> OTHER INFORMATION: Primer sequence

<400> SEQUENCE: 44
acatttgttg ggtggtttg                                         19
```